United States Patent
Mandell et al.

(10) Patent No.: US 10,532,205 B2
(45) Date of Patent: Jan. 14, 2020

(54) LEAD FIXATION ACCESSORY, LEAD STABILIZATION TOOL, AND RELATED PROCEDURES

(71) Applicant: NeuroPace, Inc., Mountain View, CA (US)

(72) Inventors: Jacob A. Mandell, Mountain View, CA (US); Emily A. Mirro, Pacifica, CA (US)

(73) Assignee: NeuroPace, Inc., Mountain View, CA (US)

( * ) Notice: Subject to any disclaimer, the term of this patent is extended or adjusted under 35 U.S.C. 154(b) by 211 days.

(21) Appl. No.: 15/721,574

(22) Filed: Sep. 29, 2017

(65) Prior Publication Data

US 2019/0099597 A1    Apr. 4, 2019

(51) Int. Cl.
| | | |
|---|---|---|
| A61N 1/05 | (2006.01) | |
| A61B 17/34 | (2006.01) | |
| A61B 17/70 | (2006.01) | |
| A61B 17/88 | (2006.01) | |
| A61B 17/00 | (2006.01) | |

(52) U.S. Cl.
CPC ........ *A61N 1/0534* (2013.01); *A61B 17/3468* (2013.01); *A61B 17/7055* (2013.01); *A61B 17/7065* (2013.01); *A61B 17/88* (2013.01); *A61B 2017/0046* (2013.01)

(58) Field of Classification Search
CPC ... A61N 1/0534; A61B 90/11; A61B 17/3468; A61B 17/7055; A61B 17/7065; A61B 17/221; A61B 17/88; A61B 2090/103; A61B 2017/0046; A61B 2017/22035
See application file for complete search history.

(56) References Cited

U.S. PATENT DOCUMENTS

| | | |
|---|---|---|
| 5,666,970 A | 9/1997 | Smith |
| 5,681,280 A | 10/1997 | Rusk et al. |
| 5,741,320 A | 4/1998 | Thornton et al. |
| 5,857,997 A | 1/1999 | Cimino et al. |
| 6,585,718 B2 | 7/2003 | Hayzelden et al. |
| 6,605,086 B2 | 8/2003 | Hayzelden et al. |
| 6,648,875 B2 | 11/2003 | Simpson |

(Continued)

OTHER PUBLICATIONS

Agilis EPI Steerable Introducer. Dual-Reach 40 cm Sheath. Product Highlights (2013).

*Primary Examiner* — Amanda K Hulbert
*Assistant Examiner* — Roland Dinga
(74) *Attorney, Agent, or Firm* — Loza & Loza, LLP; David S. Sarisky

(57) ABSTRACT

A lead fixation accessory configured to be positioned over a skull hole and to transition between an opened state and a closed state during a lead implant procedure protects against lead migration by providing a mechanism for securing the lead in place at the skull hole while a stylet is removed from the lead. The lead fixation accessory remains in place after the implant procedure to provide chronic lead stability. A lead stabilization tool configured to access and grip a lead through a slotted cannula during the lead implant procedure also protects against lead migration by providing a mechanism for securing the lead in place at a point where the lead exits the skull hole while the slotted cannula is removed from the skull hole and peeled away from the lead.

10 Claims, 36 Drawing Sheets

(56) References Cited

U.S. PATENT DOCUMENTS

| | | | |
|---|---|---|---|
| 2010/0042110 A1* | 2/2010 | Kelley | A61B 17/12 |
| | | | 606/129 |
| 2013/0116704 A1* | 5/2013 | Geistert | A61B 17/0642 |
| | | | 606/129 |
| 2014/0025082 A1* | 1/2014 | Sack | A61B 17/844 |
| | | | 606/104 |
| 2016/0158530 A1* | 6/2016 | Drake | A61B 17/3468 |
| | | | 606/129 |
| 2018/0104481 A1* | 4/2018 | Boggs | A61N 1/0551 |

* cited by examiner

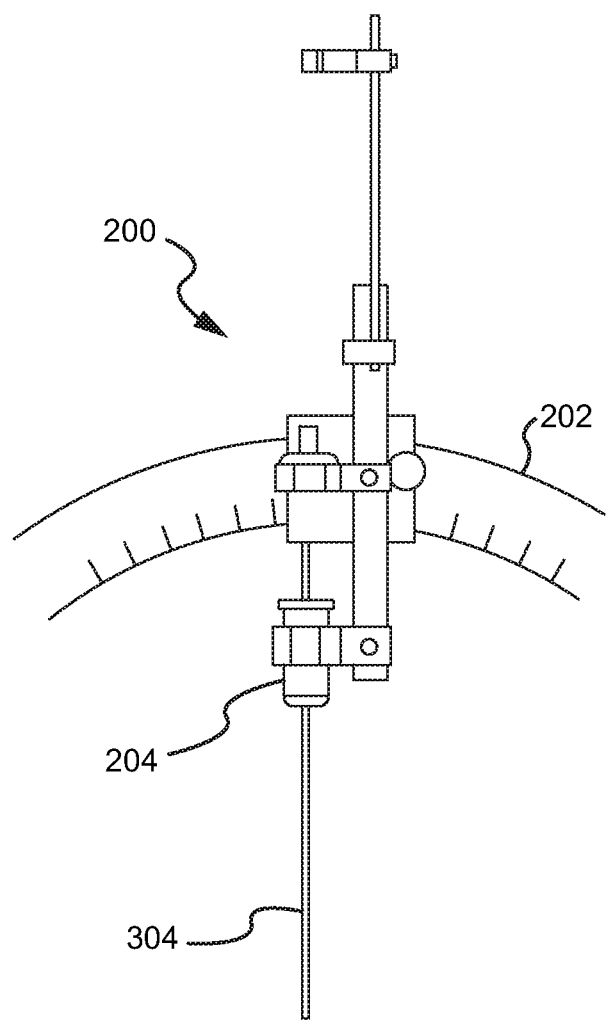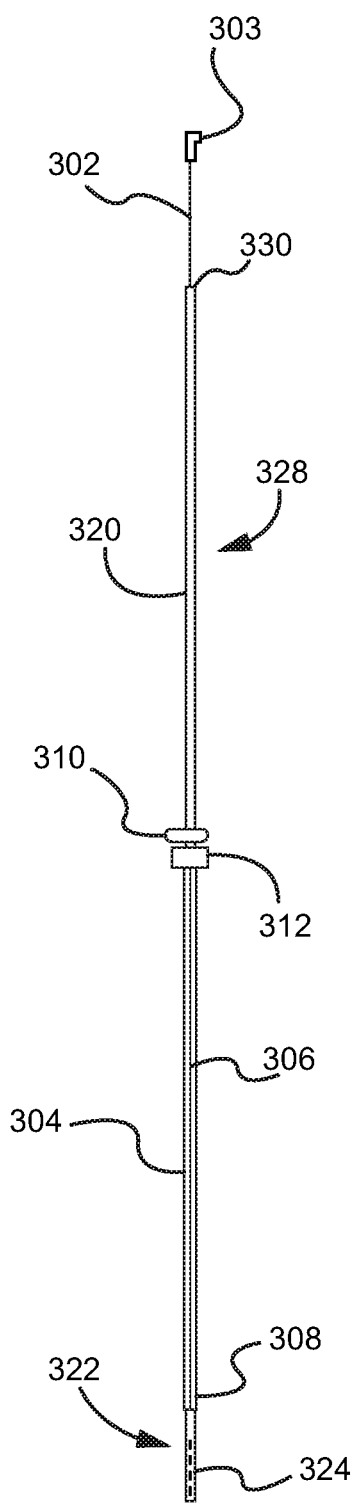
FIG. 2
FIG. 3

LEAD FIXATION ACCESSORY, LEAD STABILIZATION TOOL, AND RELATED PROCEDURES

BACKGROUND

Field

The present disclosure relates generally to apparatuses and methods used when implanting a medical device in a patient, and more particularly, to accessories, tools, and methods for using the same that minimize the degree to which the distal end of an implanted brain lead will be dislodged from its target in or on brain tissue once it has been located there, due to manipulation of the lead in subsequent steps in the implantation procedure.

Background

Some diagnostic or interventional medical procedures require implanting one or more leads through a hole in a patient's cranium. Once the surgeon places a lead so that the distal end is at a desired location, the surgeon wants the lead to stay there for whatever ultimate medical purpose the lead has, for example, to monitor physiological parameters from a patient or to deliver a therapy to the patient. Usually, however, there are steps subsequent to placing the lead that are necessary to complete the surgical procedure, and some of these may cause inadvertent displacement of the lead away from the desired location, which may not be corrected easily or efficiently.

Generally, leads may be provided with electrodes configured to sense information from the brain or to deliver a form of stimulation to the brain intended to modulate neural activity, such as electrical stimulation. The sensing and/or stimulation may occur at a distal end of the lead, for example, through electrodes exposed to brain tissue at a distal end, wherein the signals are communicated through conductors disposed in the lead body extending to a lead proximal end. Connections available at the lead proximal end allow the lead to be connected to another medical device, implanted or external, that processes the sensed signals and/or generates the form of stimulation.

For example, in the responsive neurostimulation system manufactured under the tradename RNS SYSTEM by NeuroPace, Inc., the proximal ends of one or more implanted brain leads can be connected to another implanted medical device, namely a neurostimulator that is seated in a tray or ferrule in a craniectomy in the patient's skull. In another example, the leads may be implanted in a patient so that an intracranial monitoring procedure can be undertaken for a period (e.g., several days or a couple of weeks), with the proximal ends of the implanted leads being connected to external equipment monitoring the patient's brain activity, such as to identify a focus or the foci of epileptiform activity in the patient.

There are multiple types of brain leads currently available. In applications where the leads are being used to sense or stimulate brain tissue at or near the focus of undesirable epileptiform activity, there is a depth lead (also sometimes referred to as a "deep brain lead" or as a "stereotactic depth lead", because this lead type is often implanted using stereotaxy, a three-dimensional localization and placement procedure) and a cortical strip lead (also known simply as a "cortical lead" or as a "subdural lead", because this lead type is usually implanted underneath the dura mater).

A depth lead is implanted so that the distal end is located in the brain tissue, in or adjacent a structure that is deemed to be associated with the generation of the undesirable activity. A cortical strip lead is implanted so that the distal end lays on a surface of the brain at or adjacent brain tissue that is believed to comprise an epileptic focus. The intended location of the distal end of the brain lead in or on the brain is referred to hereinafter as the "target".

A lead manufacturer may make different lead types in one or more standard lengths, rather than in lengths customized for a particular application in a particular patient. In addition, the depth lead type may be intended to be implanted using stereotactic equipment or some other tool that requires some length in excess of that which is needed to extend from the cranium and the connection to another medical device and the target (e.g., so that the lead is long enough to extend through the distance required when using a stereotactic frame mounted to the patient). For at least the reason that a lead may be manufactured to have more length than is necessary to traverse the distance between the proximal connection to another implant or external equipment and the target, brain leads are often manufactured to be quite flexible. That is, if the lead is flexible, excess length can be coiled or folded at the surface of the skull before the scalp is replaced. Further, flexibility may be considered a better alternative than a stiff lead when the lead is to remain in place in or on a surface of the brain chronically, as opposed to acutely, such as to minimize tissue damage and to optimize the integrity or resolution of signals. Brain leads manufactured and sold with the RNS SYSTEM, for example, have a flexibility on par with that of a piece of cooked spaghetti.

When implanting a lead in the brain tissue, though, its relative flexibility can present challenges when delivering the distal end to the target. Accordingly, a brain lead is often provided with an inner lumen through which a removable stiffener, such as a stylet, can be disposed. The stylet lends stability to the lead while the distal end is routed to the target, and is then removed when the lead has been positioned where it is intended to remain, either acutely or chronically. It is undesirable, however, if the act of withdrawing the stylet causes the distal end to move away from the target.

Equipment or tools used in implanting a brain lead can also unintentionally cause the distal end of a brain lead to move away from the target in procedural steps undertaken subsequent to placing the lead. For example, a slotted cannula is often employed in implanting leads stereotactically, in which a hole is formed in the patient's skull at a location calculated to allow an appropriate trajectory of a lead to deep brain target. In one example of such a procedure, a frame is attached to the patient, and a guide tube is oriented to achieve the desired trajectory relative to the skull hole. A cannula is inserted through the guide tube, such that its range of motion is constrained by the guide tube. The cannula may be provided with a removable rod disposed in an inner lumen thereof. The cannula is advanced through the skull hole towards the target. The inner rod in the cannula prevents tissue from backing up into the cannula while it is advanced.

When the cannula has been advanced to or approximate the target, the inner rod is removed and a depth lead inserted into the cannula lumen. The surgeon then advances the depth lead to the target. (Sometimes the depth lead is marked in advance at a proximal location, for example, with a stop gauge, to provide feedback to the surgeon when the target has been reached.) Once the distal end of the lead reaches the target, the cannula must be withdrawn from the brain and the lead must be extracted from the cannula, so the stereotactic equipment can be removed. A cannula is often provided with a longitudinally-extending slot with a width wide enough to accommodate the diameter of the lead body for this purpose, i.e., so that the lead can be stripped away from the cannula using the slot, rather than having to retract the cannula over the lead body. This allows the lead to be manufactured with somewhat less excess lead length than if the lead had to be long enough to retract the cannula over the very proximal end of the lead. As is the case with withdrawing a stylet, it is undesirable if the act of disengaging the lead body from a cannula (or other apparatus used for stereotaxy) causes the distal end of the brain lead to move away from the target.

A hole in the skull is often formed with some standard diameter, owing to the drills typically available in the operating room to create it. When an air drill is used to create a hole in the skull with a diameter of 5 mm or greater, the skull hole is often referred to as a "burr hole." Surgeons create standard-sized burr holes, because there are surgical accessories intended for use with burr holes that are intended for use with certain burr hole diameters, such as 14 mm. However, the diameter of a brain lead may be much smaller than that of a burr hole, because 14 mm is on the order of ten times greater than the diameter of the lead to be implanted. For example, some brain leads manufactured by NeuroPace, Inc. have a diameter of only 1.27 mm. Therefore, in some cases a surgeon may choose to use a smaller diameter hole through which to implant a lead. For example, a surgeon may choose to use a hand-held twist drill to create a hole with a diameter on the order of less than 5 mm (depending on the diameter of the twist drill bit: a common one results in a 3.2 mm diameter hole). A skull hole formed using a twist drill is sometimes referred to as a "twist drill hole".

In view of the foregoing, it would be beneficial to provide accessories and tools that reduce the likelihood that the distal end of a brain lead will be dislodged after it has been implanted at a target, as a consequence either of surgical steps or post-surgical factors, such as a patient fiddling with the lead or the skull hole through the scalp. Embodiments of a lead fixation accessory, a lead stabilization tool, and method of using them disclosed herein address these needs and others.

SUMMARY

Disclosed herein are apparatuses and methods for discouraging movement of a lead implanted through a skull hole once the surgeon has placed the distal end of the lead at a desired target. A versatile lead fixation accessory can be used with a variety of diameters of skull hole, and can be affixed to the skull before or after a lead has been implanted through a skull hole. The simple but effective design allows the lead body to be chronically secured at or near the skull hole, even while any stiffening member (such as a stylet) remains in place in the lead in the implanted lead, so that manipulating the lead to remove the stylet is less likely to dislodge the lead distal end from the target.

A lead fixation accessory according to embodiments includes a first arm having opposed ends separated by a middle region and a second arm having opposed ends separated by a middle region. A coupling mechanism couples respective first ends of the first arm and the second arm together so that the lead fixation accessory can transition between an open state or position and a closed state or position. While in an open position, the respective second ends of the first and second arms are displaced from each other. In a closed position, the respective second ends of the first and second arms are engaged, and the respective middle regions of the first and second arms form at least one opening sized to secure a lead in place near a hole formed in a skull.

In one configuration, the arms are separate components that are coupled together during placement of the lead fixation accessory. To this end, the coupling mechanism is an attachment mechanism, e.g., a bone screw, that couples the first and second arms together by attaching the first ends of the arms to a surface of the skull in a way that allows for rotational movement of the arms relative to each other. In other configurations, the lead fixation accessory is a fully assembled device. In this case, the coupling mechanism may be a hinge assembly that couples the first and second arms together in a way that allows for rotational movement of the first arm and the second arm prior to placement on the skull. The hinge assembly may include an opening that receives an attachment mechanism for attaching the lead fixation accessory to the skull. Alternatively, an opening through one or more of the arms may receive an attachment mechanism. In either configuration, once the lead fixation accessory is secured to the skull, the accessory may then be closed by rotating one of the arms until the second ends of the arms engage, after which the lead fixation accessory may be further secured to the skull using an additional attachment mechanism.

The one or more openings of the lead fixation accessory that secure a lead are characterized by a geometry or cutout shape formed by the middle regions of the first and second arms. For example, if the edges of the middle regions that face each other when the accessory is closed are linear, the geometry of the opening defined by facing edges would be a rectangle. If one of the facing edges includes a semicircular cutout and the other is linear, the geometry of the opening would be a semicircle. Numerous other opening shapes are possible. Furthermore, several separate openings—each for securing a separate lead—may be formed by an edge that includes multiple cutouts and a linear edge. In all cases, the cutout shape is characterized by a dimension that ensures that the middle regions of the accessory apply a force to the lead sufficient to hold the lead in place. For example, a circular opening would have a diameter slightly less than the diameter of the lead body, so that when the accessory is closed around the lead body and secured to the skull, the lead body is affixed to the accessory.

A lead stabilization tool according to embodiments is configured to hold a lead in place near a hole in a skull during a lead implant procedure. The lead stabilization tool includes a housing, an extension member at least partially located in the housing, a grip structure, and an operating mechanism configured to transition the lead stabilization tool between an extended state and an at least partially retracted state. In an extended state, the grip structure is located distal a nose of the housing so that it can be positioned through a slotted wall of a cannula and manipulated to at least partially encircle the lead. In a partially retracted state, the grip structure is located relative to the nose to apply a force to the lead to thereby hold the lead in place.

Transitioning of the tool between an extended state and a retracted state may be implemented through displacement of the extension member along a longitudinal axis of the housing. To this end, the operating mechanism may include a push button coupled to the extension member through a biasing mechanism that translates a force applied to the push button in a direction perpendicular to the longitudinal axis to a force applied to the extension member in the direction of the longitudinal axis. In another variation, the operating mechanism may include a rotational thumb wheel coupled to the extension member by a threaded engagement that translates rotational force applied to the thumb wheel to a force applied to the extension member in the direction of the longitudinal axis. IN yet another variation, the operating mechanism may include a slide button coupled to the extension member by a fixed mechanical engagement that transfers force applied to the slide button to the extension member in the direction of the longitudinal axis.

It is understood that other aspects of accessories, tools, and methods for using the same will become readily apparent to those skilled in the art from the following detailed description, wherein various aspects of apparatuses and methods are shown and described by way of illustration. As will be realized, these aspects may be implemented in other and different forms. Accordingly, the drawings and detailed description are to be regarded as illustrative in nature and not as restrictive.

BRIEF DESCRIPTION OF THE DRAWINGS

Various aspects of apparatuses and methods will now be presented in the detailed description by way of example, and not by way of limitation, with reference to the accompanying drawings, wherein:

FIG. 2 is an illustration of some components of stereotactic equipment that may be used in a standard stereotactic procedure with a frame to implant a depth lead in a patient's brain.

FIG. 3 is an illustration of a cannula (with a depth lead inserted therein) that may be used during a procedure for implanting a depth lead.

DETAILED DESCRIPTION

Disclosed herein in detail are embodiments of a lead fixation accessory that allow the body of a brain lead to be secured at the surface of a patient's skull while a stiffening element, such as a stylet, remains in place in a lumen of the lead body. The stiffening element thus can be withdrawn from the lead after the lead fixation accessory is in place, reducing the likelihood that the act of pulling out the stylet will displace the distal end of the implanted lead away from the target.

Also disclosed herein in detail are embodiments of a lead stabilization tool for use in a procedure to implant a brain lead using a slotted cannula that allow the lead body to be stabilized near the surface of the patient's skull while the slotted cannula and the lead body are separated from each other, which makes it less likely that the act of separating the cannula and the lead will cause the lead to pull away from the target than if the lead body had to be stabilized proximally of the skull surface, such as at or above the top of the cannula.

The embodiments are described primarily with reference to the medical device being an electrode-bearing lead, as might be used in an application for deep brain stimulation or direct brain stimulation such as the responsive stimulations applications by NeuroPace, Inc. of Mountain View, Calif. It should be appreciated, however, that the lead fixation accessory and the lead stabilization tool may be used with good results to secure a segment of a different type of medical device, such as a catheter or other medical instrument (with a diameter compatible with the accessory), relative to a surface of the skull prior to and/or during use of the medical device in its intended application. Similarly, it should be appreciated that, in some circumstances, embodiments of a lead fixation accessory described herein may be used to secure more than one medical device simultaneously (e.g., two leads) for some applications.

Overview of Procedures to Implant Brain Leads, Tools, and Devices

For purposes of illustration, procedures to implant a depth lead and a cortical strip lead will be described with reference to a responsive neurostimulation system, in which a surgeon commonly uses both lead types.

Figure 1A:
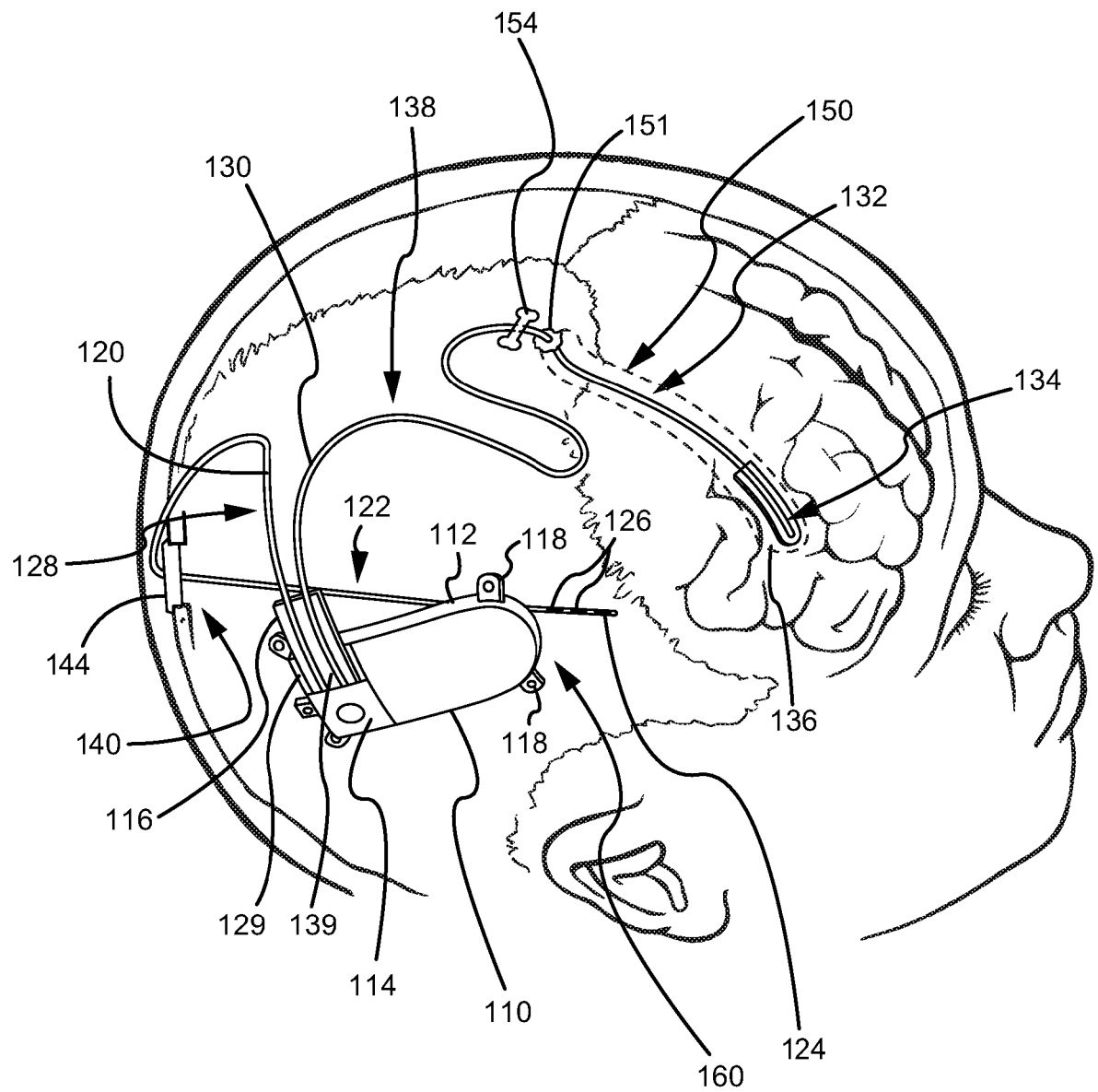
FIG. 1A is a schematic of a patient's cranium showing implanted components of a neurostimulation system, including leads and a neurostimulator, and related surgical accessories, including a burr hole cover and a lead fixation plate.

With reference to FIG. 1A, a neurostimulator 110 and leads 120, 130 of a responsive neurostimulation system are shown schematically, implanted in a patient. To implant a lead, the surgeon needs access to the brain. A surgeon may gain access to the brain for purposes of implanting a lead by creating an opening through the skull. A opening may be created by drilling a hole through the skull, by performing a craniotomy (temporarily removing a bone flap from the skull and replacing the flap after access to the brain is no longer needed) or by performing a craniectomy (permanently removing a bone flap from the skull). Such opening may be used exclusively for lead implant purposes, or may be used for another/additional purpose (for example, the surgeon can first deliver a lead to a target through an opening formed as part of a craniectomy, then use the same opening to implant another medical device, such as a neurostimulator). The term "skull hole" is used herein to refer to any category of opening formed in a patient's skull to gain access to the subdural spaces and to the brain.

In FIG. 1A, three skull holes have been formed: a burr hole 140 for purposes of implanting a depth lead 120, a craniotomy 150 for purposes of implanting a cortical strip lead 130, and a craniectomy 160 in which a tray or ferrule 112 and a neurostimulator 110 are ultimately implanted. More particularly, the surgeon may use an air-powered drill to form an annular burr hole 140 of a diameter between 5-30 mm, with 14 mm being a commonly-used diameter, for purposes of implanting a depth lead 120. Using appropriate tools, the surgeon may also perform a craniotomy 150 for purposes of implanting a cortical strip lead 130, and additionally a craniectomy 160 in which to ultimately situate a neurostimulator at the patient's skull.

In FIG. 1A, a distal portion 122 of the depth lead 120 extends into the patient's brain tissue from a 14-mm burr hole 140, and a proximal portion 128 extends proximally from the burr hole where it is plugged in at a proximal end 129 to a connector 114 of an implanted neurostimulator 110. A distal portion 132 of a cortical strip lead 130 extends from a fissure like opening or hole 151 at an edge of the craniotomy 150 onto a surface of the patient's brain, between the brain and the dura mater (not shown), and a proximal portion 138 extends proximally from the hole where it is plugged in at a proximal end 139 to the connector 114. The neurostimulator 110 has a strain relief 116 in the location where the proximal ends 129, 139 of the leads connect, to discourage the leads from unintentional disconnection.

A distal end 124 of the depth lead 120 includes a plurality of electrodes 126 (three are shown in FIG. 1A), that can be used either for sensing electrographic activity from the brain or for delivering a therapy of electrical stimulation to it in an effort to modulate neural activity (e.g., lessen the severity of a seizure). Conductors extending the length of the lead body (not shown) and connected at the connector 114 to the neurostimulator 110 allow the neurostimulator to process the sensed signals and to generate the stimulation signals. A distal end 134 of the cortical strip lead 130 ends in a paddle 136 that, on a brain-facing surface thereof (not shown in FIG. 1A), exposes another plurality of electrodes (e.g., four) to the brain surface underneath the dura mater. These electrodes are also in electrical communication with the neurostimulator 110 via conductors in the cortical strip lead 130 and the connection at the connector 114.

In addition to the burr hole 140 or the craniotomy 150 opening 151, a lead, especially of the cortical strip lead type, may be implanted using another opening in the cranium. More specifically, to implant the neurostimulator 110, the surgeon cuts a craniectomy 160 hole using a template that approximates the shape of the neurostimulator. The surgeon fits a tray or "ferrule" 112 into the hole and attaches or otherwise secures it to the cranium, for example, using bone screws and/or folding tabs 118 providing on the tray. The surgeon then situates the neurostimulator 110 into the tray 112. However, before placing the tray 112, the surgeon can use the craniectomy 160 hole to implant a cortical strip lead, such as the cortical strip lead 130, and then connect the proximal end thereof to the neurostimulator connector. (FIG. 1A does not show any lead implanted using the craniectomy 160 in which the tray 112 and neurostimulator 110 are situated.)

Figure 1B:
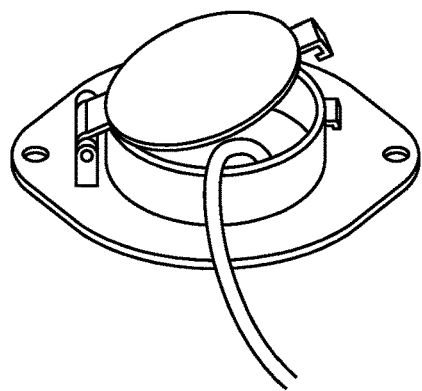
FIGS. 1B and 1C are illustrations of known burr hole covers.
Figure 1C:
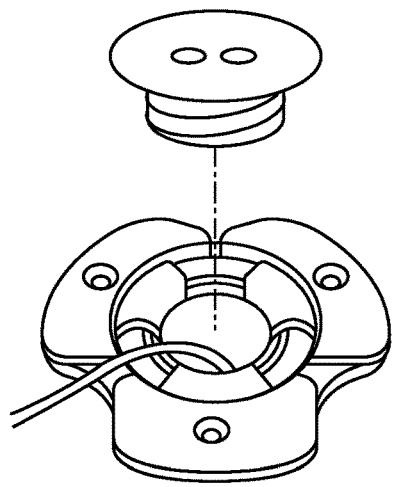

Both of the implanted leads 120, 130 in FIG. 1A are shown secured with known lead fixation accessories. The depth lead 120 implanted through the burr hole 140 is shown secured with a burr hole cover 144 which substantially fills the 14-mm diameter burr hole except for an aperture therethrough that permits passage of the lead body. Examples of lead fixation accessories designed for burr holes are illustrated in FIGS. 1B and 1C.

Some burr hole lead fixation devices are designed for use with mechanical parts that need to be actuated in order to achieve fixation of the lead body, and others rely on friction fit or compression to limit movement of the lead relative to the device. Some require at least one element of the accessory to be put in place before a procedure to implant a lead is begun. Some allow fixation only after any stiffening element used in implanting the lead has been removed. With reference to FIG. 1B, a burr hole lead fixation accessory manufactured by Medtronic, Inc. under the tradename "STIMLOC" uses several interlocking parts to secure a lead body. With reference to FIG. 1C, a two-piece burr hole cover manufactured by NeuroPace, Inc. relies in part on fitting a portion of the lead body into a groove in base element to reduce the likelihood that further manipulation of the lead portion extending proximally of the skull hole (e.g., to connect the lead to an implanted neurostimulator) will translate to movement of the distal end away from the target.

Figure 1D:
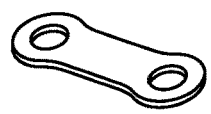
FIG. 1D is an illustration of a known lead fixation plate.

In FIG. 1A, the cortical strip lead 130 implanted through the craniotomy 150, and having a proximal portion 138 extending from the opening 151 at an edge of the craniotomy 150 onto the surface of the skull is secured at a point on the lead body just proximal of where the lead body extends out of the hole, with a cranial plate 154. The cranial plate 154 is situated over the lead body and then secured to the surface of the skull on either side of the lead body with bone screws. Because of its shape, the type of cranial plate 154 shown in FIG. 1A is commonly referred to as a "dog bone". One such plate is shown in FIG. 1D and is manufactured under the tradename "MATRIXNEURO" by Synthes CMF. The cranial plate 154 compresses the lead body to prevent lateral movement of the lead at the point of fixation to the skull. If the compression is inadvertently excessive (e.g., by over-tightening of the screws or by a patient pressing down on the plate), the integrity of the lead may be compromised (e.g., the conductors between the electrodes at the lead distal end and the connector at the lead proximal end may be shorted).

The target for a depth lead 120 is usually more precise than the target for a cortical strip lead 130, at least in an application where the condition is epilepsy. That is, the target for a depth lead 130 is usually a particular structure in the brain, such as the subthalamic nucleus (STN) or the cingulate gyrus. The target for a cortical strip lead 130 may be somewhat more forgiving of imprecision, that is, the electrodes on the distal end 124 of the strip lead 120 may be destined to cover the general area on the surface of the brain where epileptic activity is believed to be focused. Thus, it may be especially beneficial to limit movement of the distal end of a depth lead once it has been placed at the target.

In part because of the need for precision and in part because the lead is being implanted into brain tissue as opposed to on a surface of it, a depth lead 120 is most often implanted using some form of stereotaxy (e.g., with a frame affixed to the patient's skull or a "frameless" version of it). Stereotactic procedures are well known and will not be described herein to any great degree. Briefly, however, one common method uses frame-based stereotaxis to approach a target or targets through a skull hole. The patient is given a local anesthetic and a rigid frame or fixation device is attached to the patient's head, and the brain is imaged (e.g., with a CT scan). The location of the target(s) is calculated based on a 'co-registration' of the images and the frame, fiducials or other registered points on the head. Then, the patient is sedated for surgery, the scalp is incised, and one or more skull holes are formed (e.g., a burr hole or a twist drill hole) in the patient's cranium, each at a location that will allow an appropriate trajectory to the deep brain target(s). (Depending on the size of a skull hole, it may be possible to implant more than one lead using the same hole. For example, a 14-mm diameter burr hole is large enough to accommodate more than one 1.27 mm diameter lead.)

Referring now to FIGS. 2 and 3, part of the stereotactic equipment 200 is secured to the patient's skull using a frame, a portion of which is shown as a graduated element 202 in FIG. 2, and a guide tube 204 is oriented to provide the desired trajectory. The guide tube 204 has an inner lumen of sufficient diameter to receive a cannula 304. The cannula 304 is also formed as a cylinder, typically made of a metal, such as stainless steel, and has an inner lumen with a diameter sufficient to slidably receive first an inner rod (not shown) and thereafter a depth lead (the distal end 124 of a depth lead 320 is shown in FIG. 3).

The cannula 304 may be provided with a slot 306 running along its entire length so that the cannula can be extracted from the lead body without having to retract the cannula over the proximal end 330 of the lead. Thus, if the cannula 304 is slotted, the slot 306 must be dimensioned so as to allow the proximal portion of the depth lead 320 that extends proximally of the skull hole to be separated from the cannula through the slot. The depth lead 320 also has an inner lumen running through most of the length of the lead in which a stiffening element, such as a stylet, is removably disposed. (In FIG. 3, a stylet 302 is shown extending proximally of the depth lead 320). The stylet 302 may have a plastic member or stylet handle 303 at its proximal end that the surgeon can grab to more easily extract the stylet from the lead inner lumen.

One or more stop gauges may be configured so that they can encircle the proximal portion of either or both of the cannula 304 or the depth lead 320 to guard against advancing the distal end of the cannula or the depth lead beyond the target (not shown in FIG. 2 or 3). For example, the depth lead 320 may be measured in the operating room to identify a location on a proximal portion that, once the lead is being routed to the target, the surgeon can use to gauge when the lead has been advanced far enough (or to some not-to-exceed distance) into the tissue. This location on the proximal portion can be demarcated by fitting a stop gauge 310 around the lead body.

Manipulating the appropriate controls on the stereotactic equipment, the cannula 304 with the inner rod ((not shown) in place is advanced into the brain. The inner rod discourages brain tissue from backing up into the cannula lumen as the cannula creates a path to the target for the lead. When the cannula 304 is advanced as far as intended, the surgeon withdraws the inner rod, and replaces it with the depth lead 320, by inserting the distal end 324 of the depth lead (with the stylet 302 in place) into the proximal end 312 (or top) of the cannula.

FIG. 3 shows a cannula 304 with a depth lead 320 inserted within the cannula inner lumen. A proximal portion 328 of the depth lead 320 extends proximally of a proximal end 312 of the cannula 304, and a distal portion 322 of the depth lead extends distally of a distal end 308 of the cannula 304. The stylet 302 is disposed in an inner lumen of the depth lead 320 and traverses substantially the full length of the depth lead 320, except for the very distal end 324 thereof. The stylet 302 is shown extending proximally of the proximal end 129 of the depth lead 320, with a stylet handle 303 at the proximal tip. The stylet 302 lends sufficient stiffness to the lead 320 while it is being manipulated during the implant procedure (e.g., to insert it into the cannula lumen, or in the case of a cortical strip lead, while it is being routed to the target by manipulating it under the skull and under the dura mater). The stylet handle 303 makes it easier to remove the stylet 302 from the lead 320 before the procedure is over. It will be appreciated that in a typical stereotactic procedure, even when the depth lead 320 is inserted into the cannula 304 and after the lead distal end 324 has been delivered to the target, there is enough excess lead length so that a portion of the lead body will extend proximally of the proximal end 312 of the cannula, so that the lead at a point on the proximal portion 328 thereof can be grasped above the proximal end 312 of the cannula 304.

After the step of the procedure where the surgeon has the distal end of the lead where he or she wants it, it is undesirable for subsequent steps to move the distal end away from the target. But preventing that from happening can be challenging.

First, the cannula has to be withdrawn from the brain and extracted from around the lead in order to complete the procedure. When a stereotactic frame is being used, the lead body extending above the proximal end of the cannula may be held against the inner lumen of the guide tube with the lead oriented so that, while the cannula is slowly retracted from the patient, the lead can be separated from the cannula through the slot. At this point, the lead cannot be stabilized any closer to the surface of the skull, because the cannula is in the way. During the step of retracting the cannula, as soon as enough room is created between the distal end of the cannula and the skull hole for the surgeon to grasp the lead body, the surgeon can use fingers, or forceps or another tool to stabilize the lead there, until the cannula is completely separated from the lead. However, until the cannula clears the skull, when the lead is only being stabilized at a point in the inner lumen of the guide tube, there is a greater likelihood that the distal end of the lead will be dislodged from the target than if the lead could be secured at or near the skull hole.

Second, after the cannula is removed, the stylet in the inner lumen of the lead still has to be extracted from the lead body before the procedure is complete. The force applied in pulling out the stylet may tend to retract the distal end of the lead along with it, so removing the stylet is another step which may result in dislodging the lead away from the target.

Third, some form of lead fixation accessory typically is used to secure a proximal portion of the implanted lead at or near the skull hole or otherwise somewhere on the surface of the skull, to discourage relative movement between the implanted distal portion of the lead and the proximal portion of the lead after the procedure is complete. The step is another opportunity for unwanted displacement of the distal end of the lead from the target.

With reference to FIGS. 4A-4F, and FIGS. 9A-9G, described are embodiments of a lead fixation accessory 402 that allows a lead body to be secured in a skull hole or on a surface of the skull proximal of a skull hole while a stiffening member (e.g., a stylet) is still in the lead.

Figure 5A:
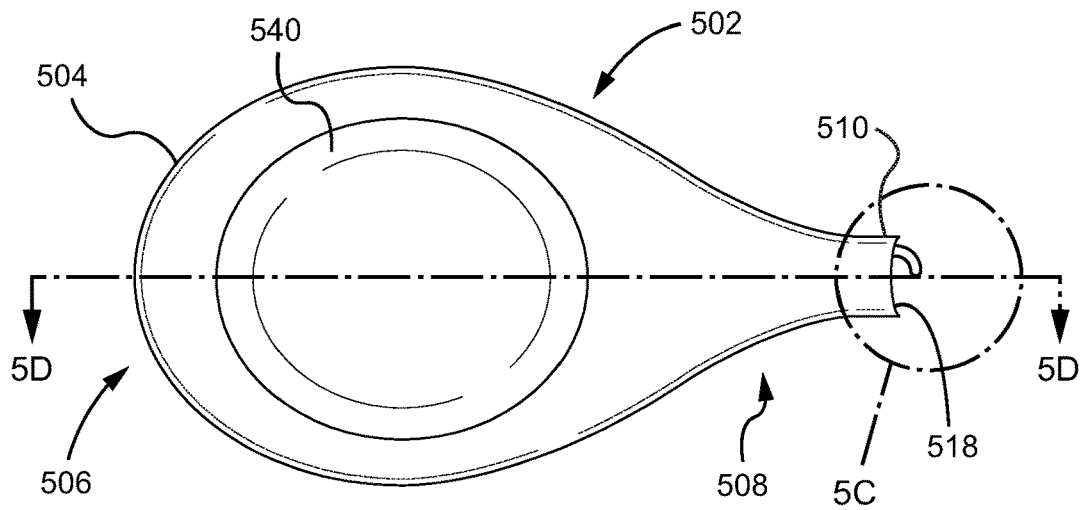
FIG. 5A is a top view illustration of a lead stabilization tool in a deactivated or resting state and having an operating mechanism that includes a push button.
Figure 5B:
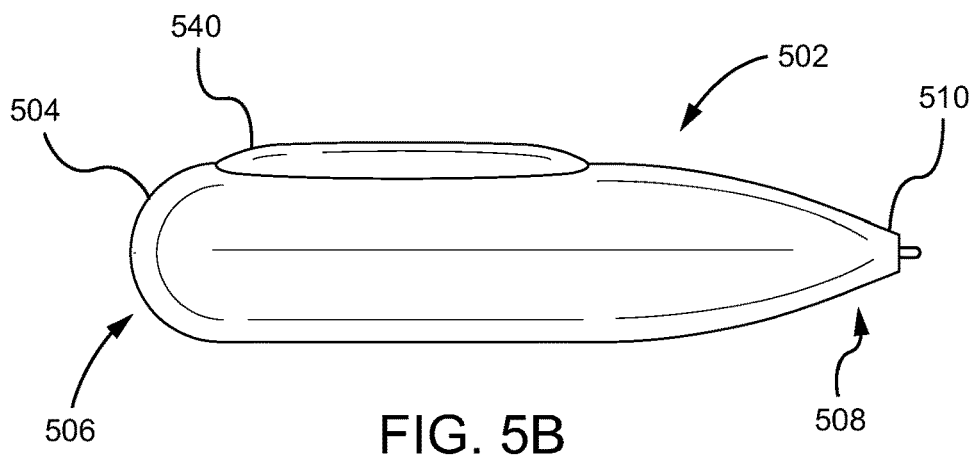
FIG. 5B is a side view of the lead stabilization tool of FIG. 5A.
Figure 5C:
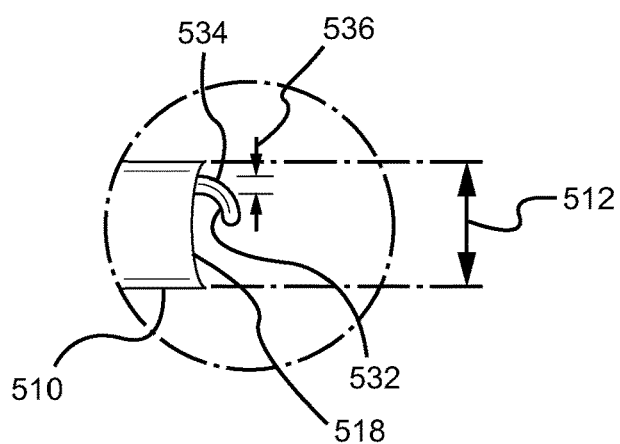
FIG. 5C is a detail view of the distal end of the lead stabilization tool of FIG. 5A.
Figure 5D:
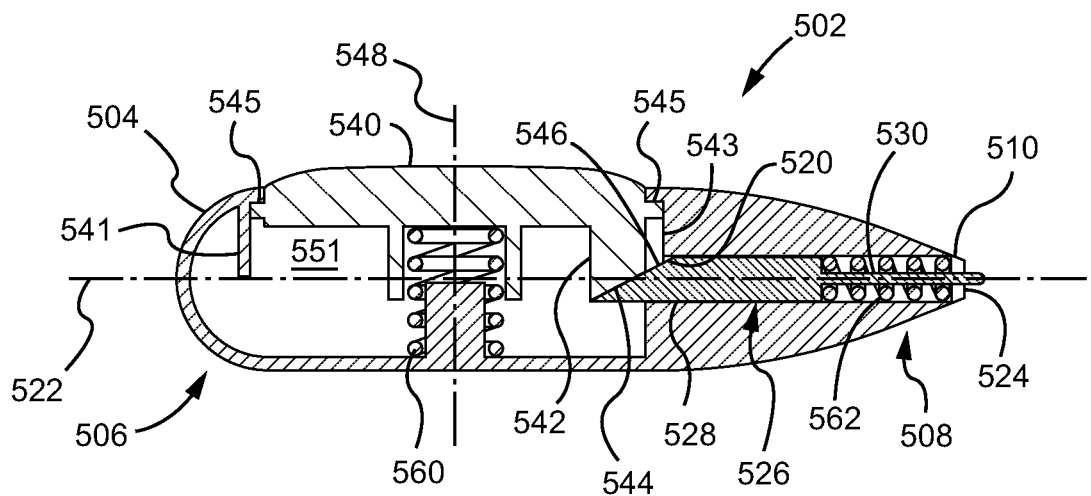
FIG. 5D is a cross section of the lead stabilization tool of FIG. 5A.
Figure 5E:
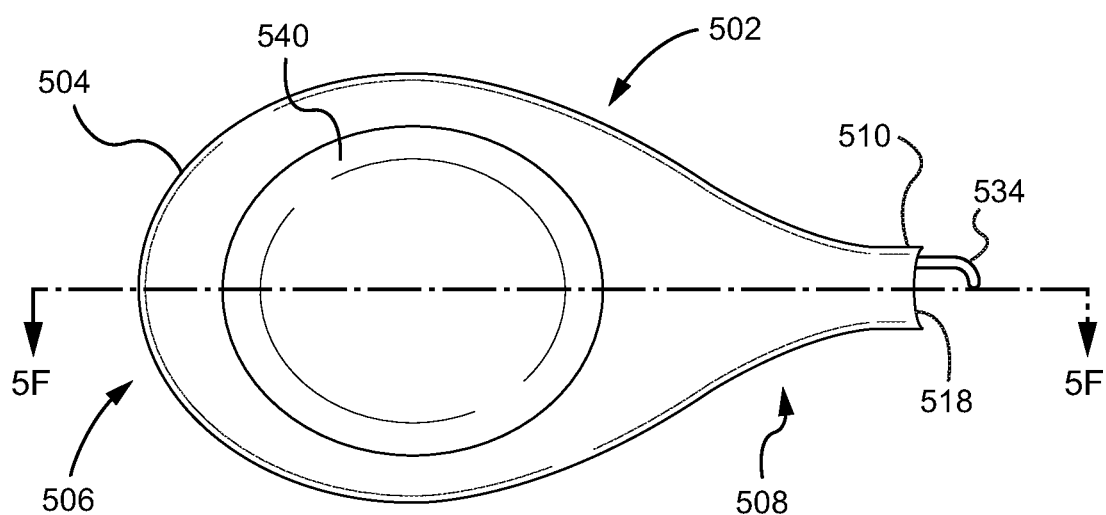
FIG. 5E is a top view of the lead stabilization tool in an extended state.
Figure 5F:
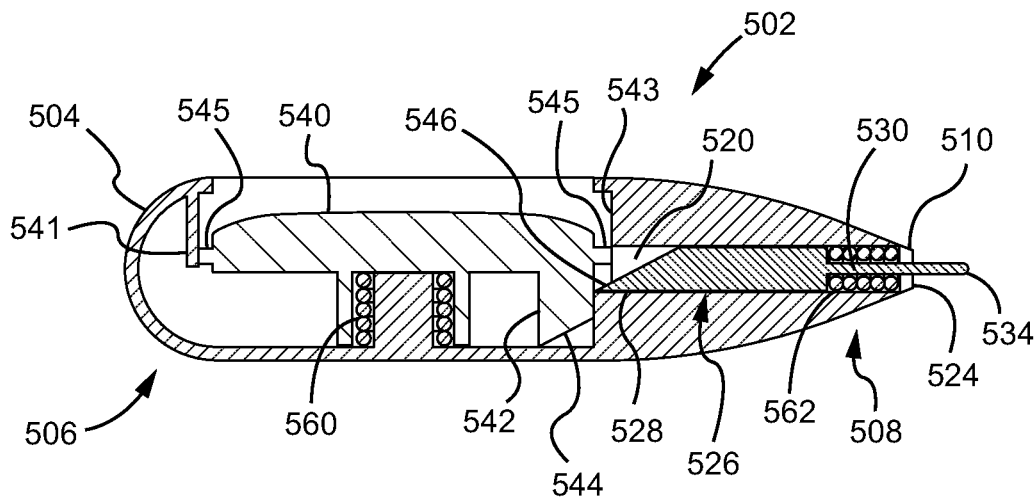
FIG. 5F is a cross section of the lead stabilization tool of FIG. 5E.
Figure 5G:
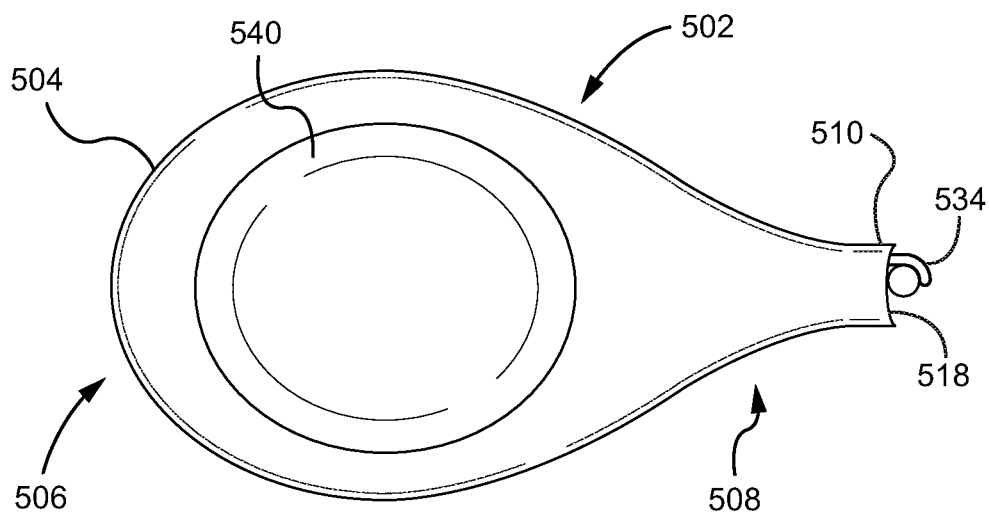
FIG. 5G is a top view of the lead stabilization tool in a partially retracted state and holding a lead.
Figure 5H:
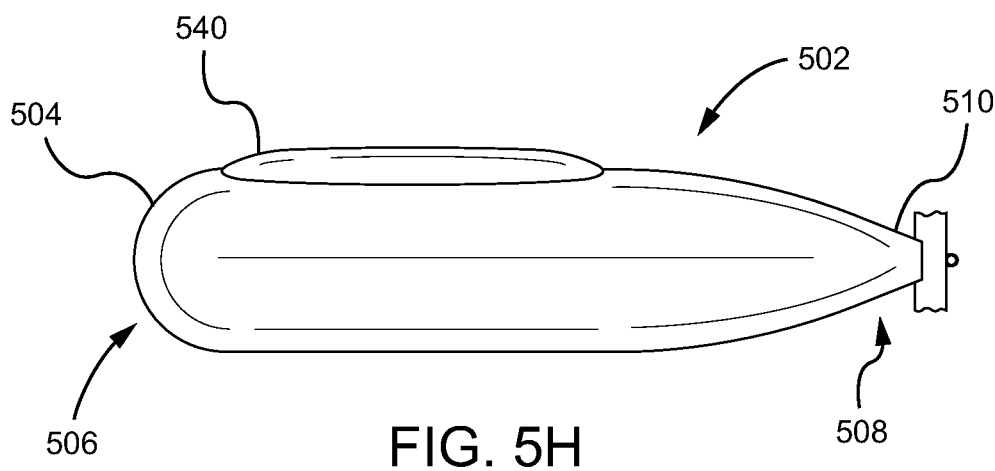
FIG. 5H is a side view of the lead stabilization tool of FIG. 5G.
Figure 5I:
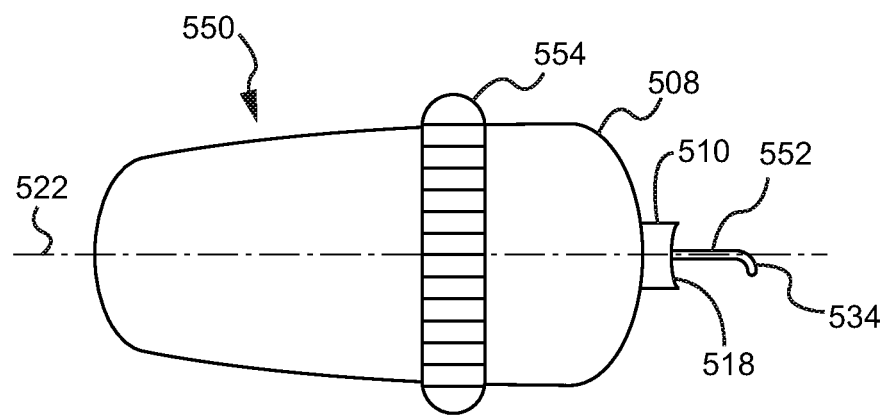
FIG. 5I is a side view illustration of a lead stabilization tool having an operating mechanism that includes a thumb wheel with a threaded coupling.
Figure 5J:
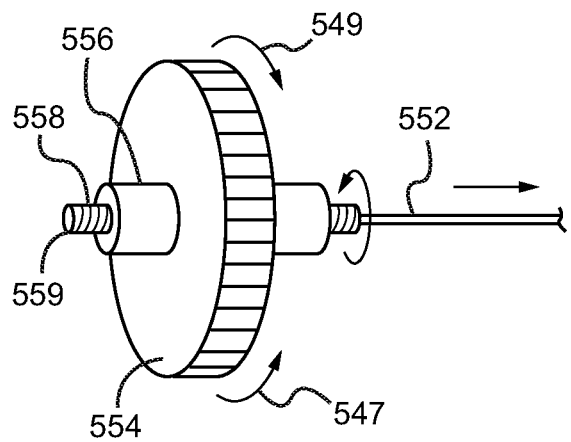
FIG. 5J a perspective view of the thumb wheel component of the lead stabilization tool of FIG. 5I.
Figure 5K:
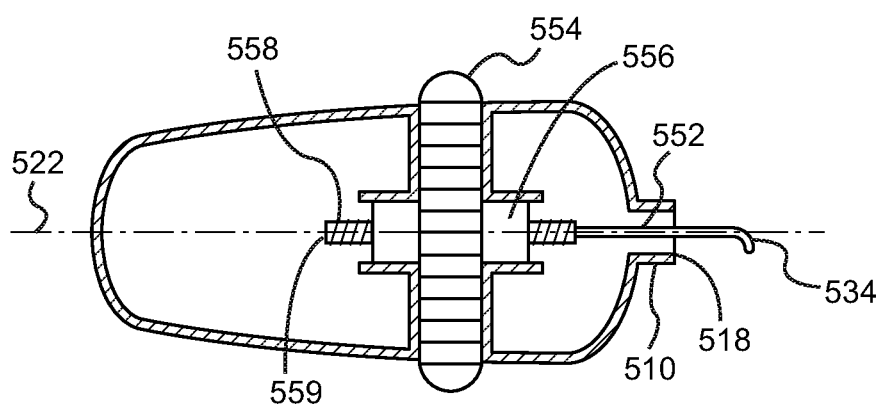
FIG. 5K is a cross section of the lead stabilization tool of FIG. 5I.
Figure 5L:
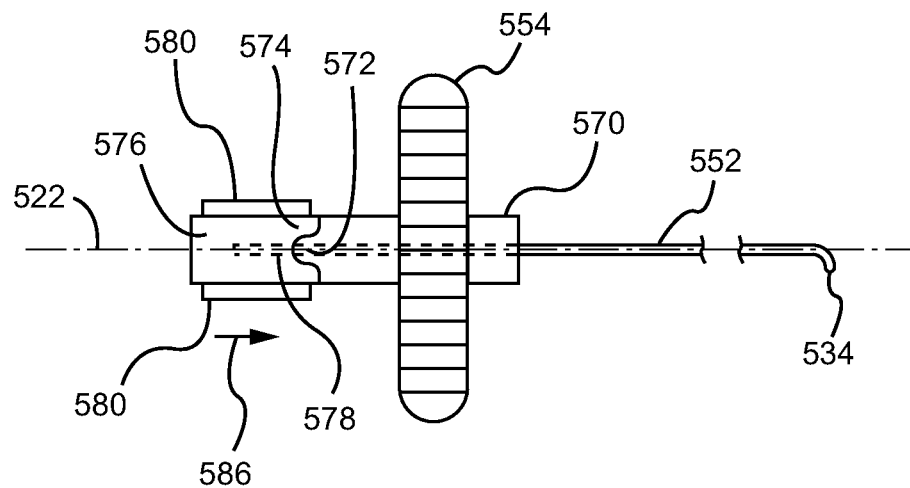
FIGS. 5L and 5M are side view illustrations of an alternate configuration of the operating mechanism of FIG. 5I that includes a thumb wheel with cam coupling.
Figure 5M:
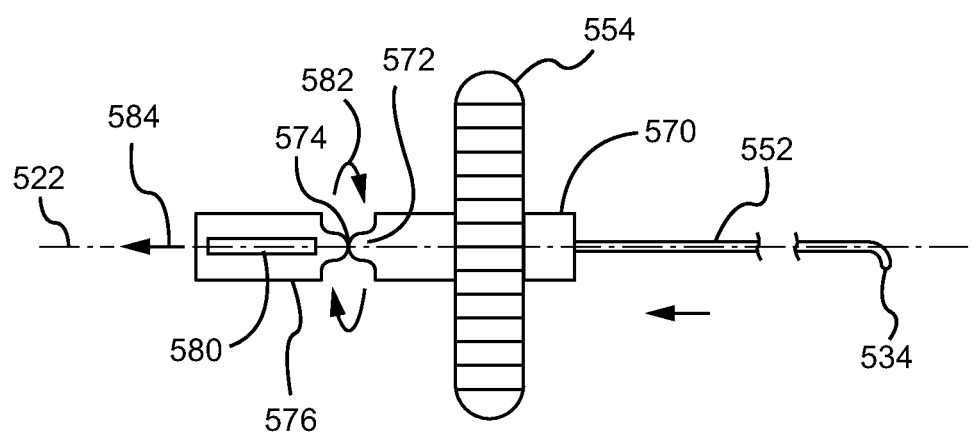
Figure 5N:
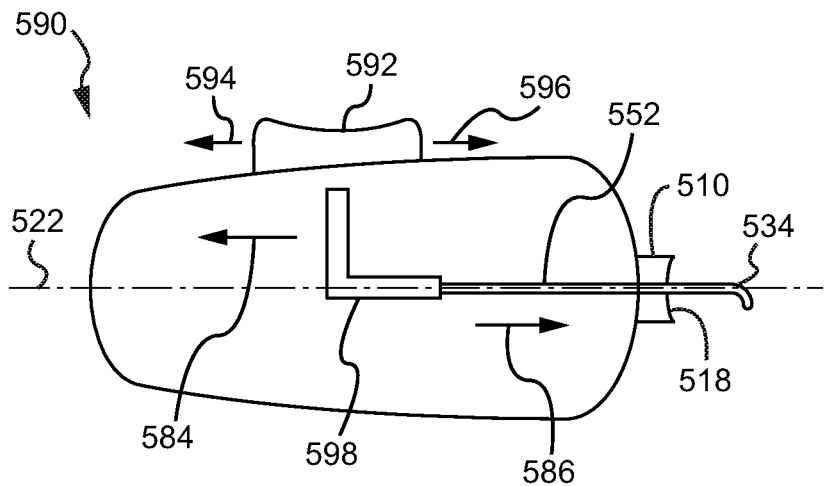
FIGS. 5N and 5O are side view illustrations of a lead stabilization tool having an operating mechanism that includes a slide button.
Figure 5O:
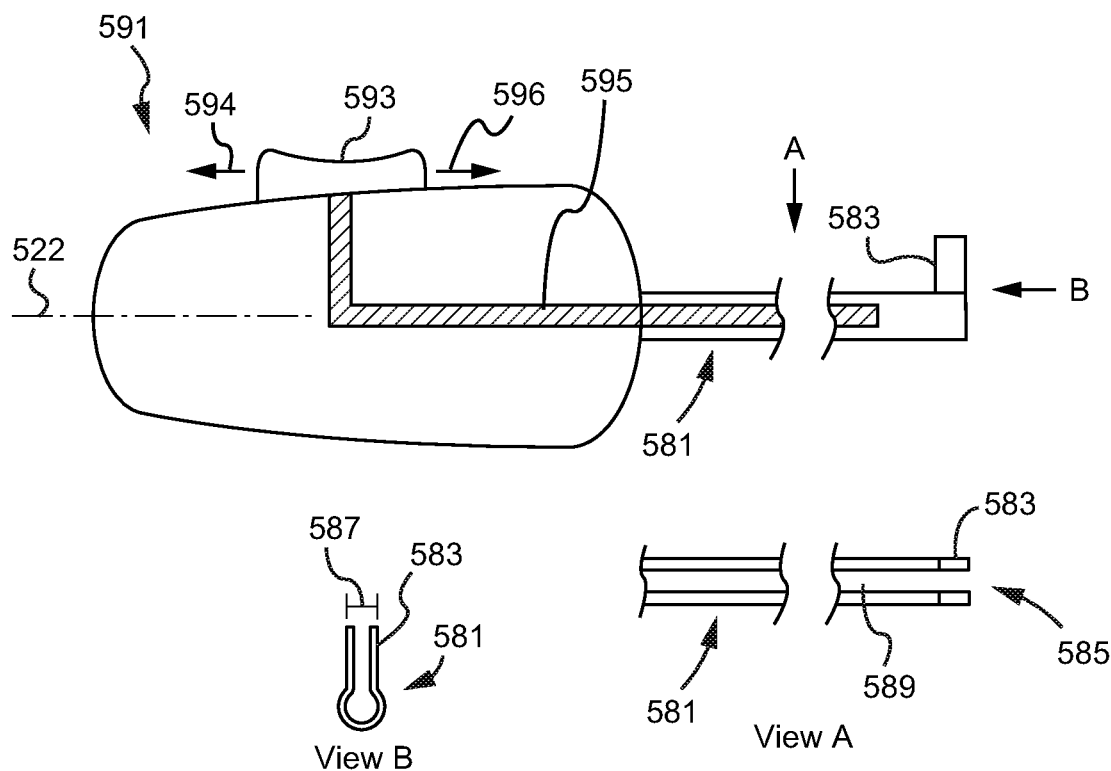
Figure 5P:
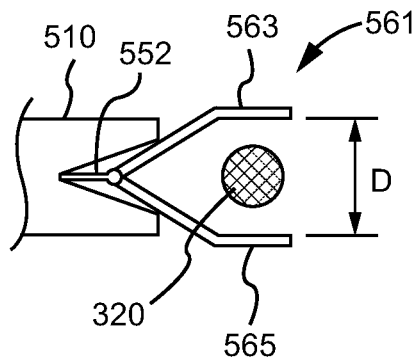
FIGS. 5P-5U are schematic illustrations of grip structures that may be incorporated into a lead stabilization tool.
Figure 5Q:
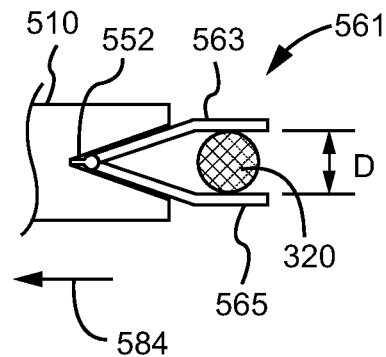
Figure 5R:
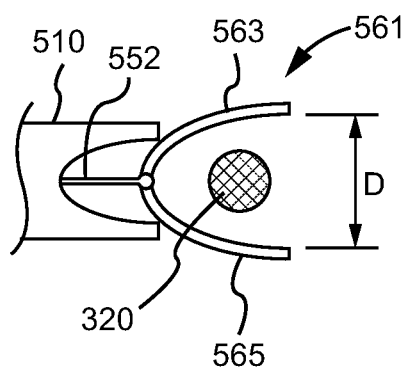
Figure 5S:
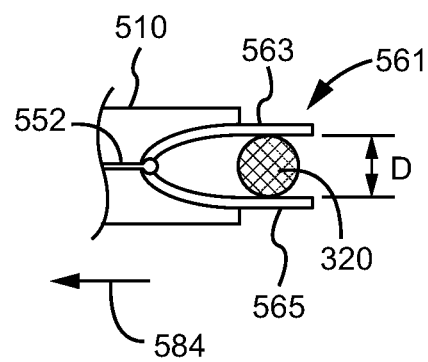
Figure 5T:
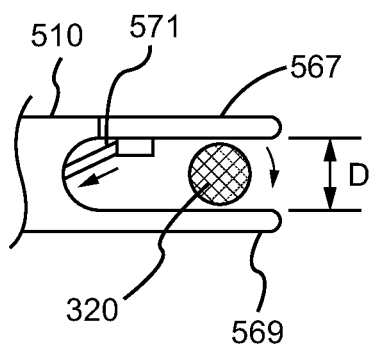
Figure 5U:
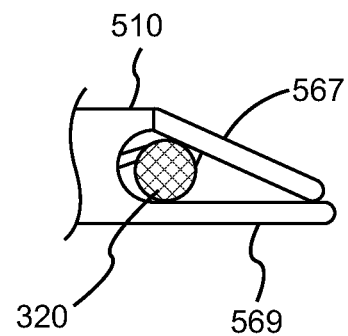
Figure 5V:
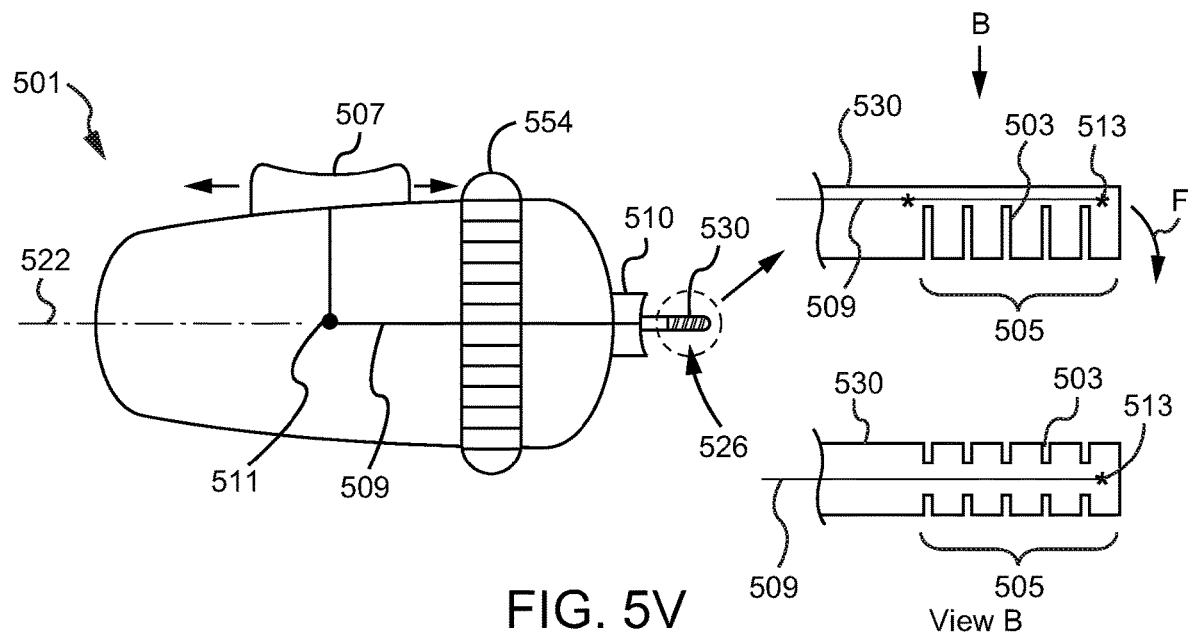
FIG. 5V is a side view illustration of lead stabilization tool in a deactivated or resting state having dual operating mechanisms, including a thumb wheel for transitioning the tool between resting, extended, and partially retracted states, and a slide button for manipulating a grip structure between linear and curved states.
Figure 5W:
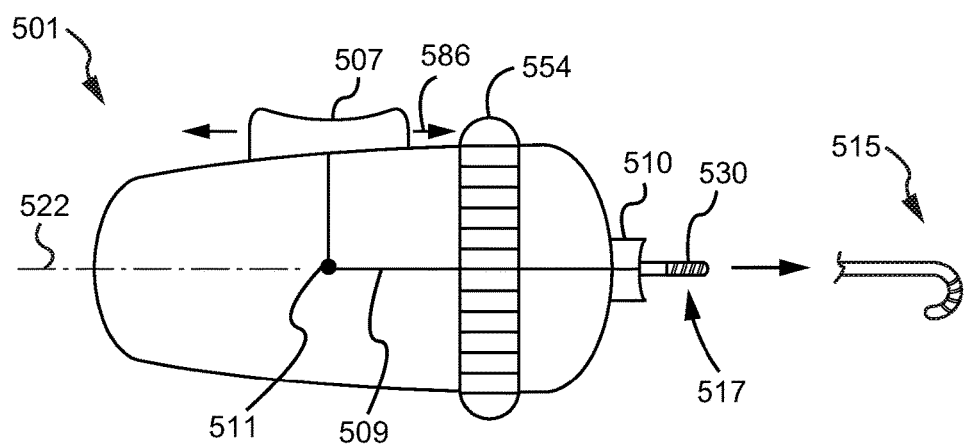
FIG. 5W is a side view illustration of the lead stabilization tool of FIG. 5V in an extended state, and showing the grip structure in a linear state and a curved state.
Figure 5X:
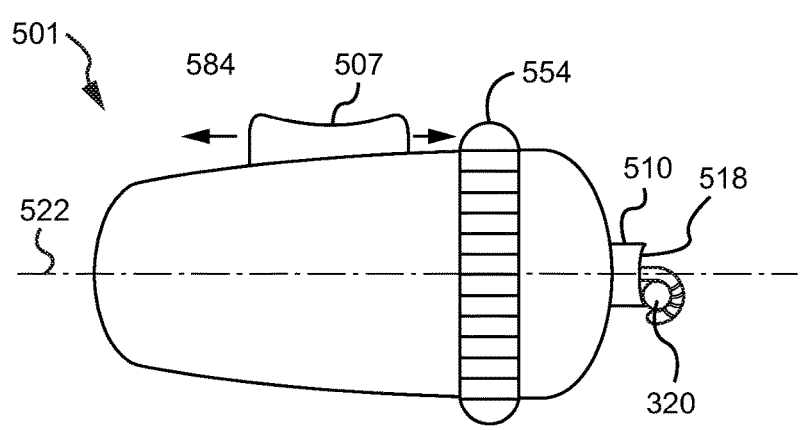
FIG. 5X is a side view illustration of the lead stabilization tool of FIG. 5V in a partially retracted state and holding a lead.

With reference to FIGS. 5A-5X, described are embodiments of a tool for stabilizing a proximal portion of a brain lead after it has been implanted at a target in a patient but before the lead has been secured at either the skull hole or the skull surface, to discourage relative movement of the lead between the target and the skull.

Figure 6:
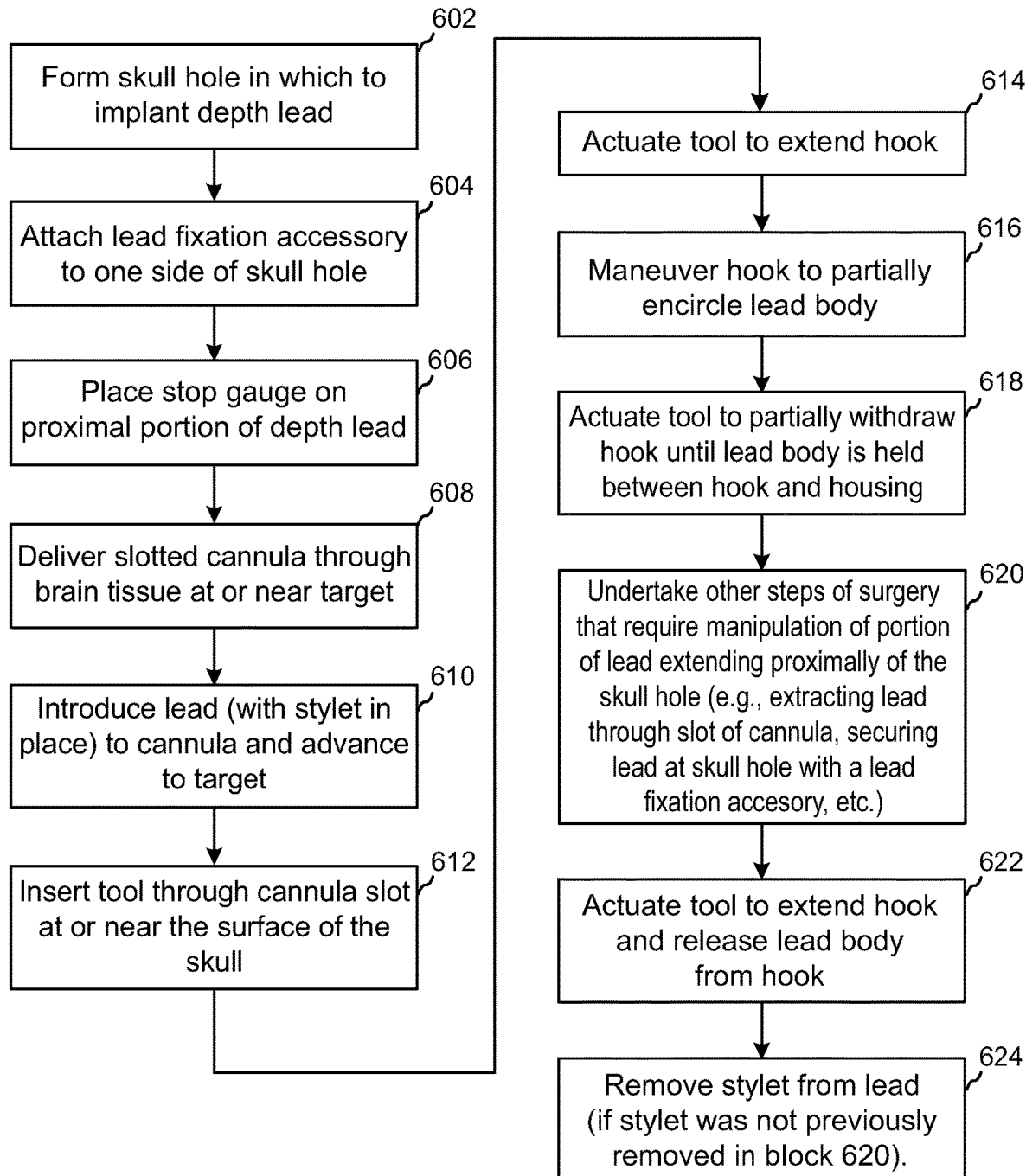
FIG. 6 is a flowchart of a method for implanting a depth lead according to embodiments.
Figure 7A:
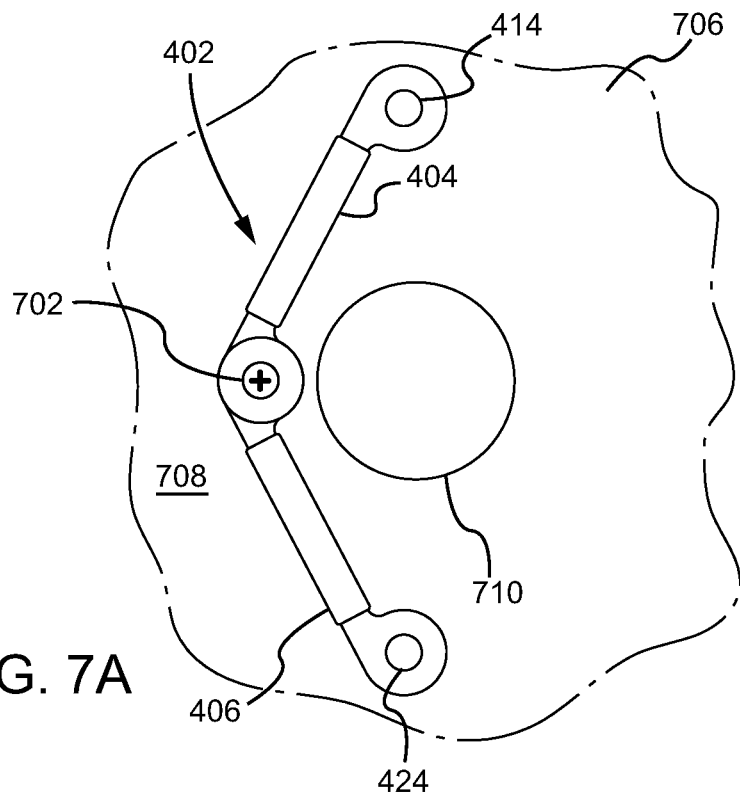
FIGS. 7A-7R are top-view and side-view schematics of various stages of the method of FIG. 6.
Figure 7B:
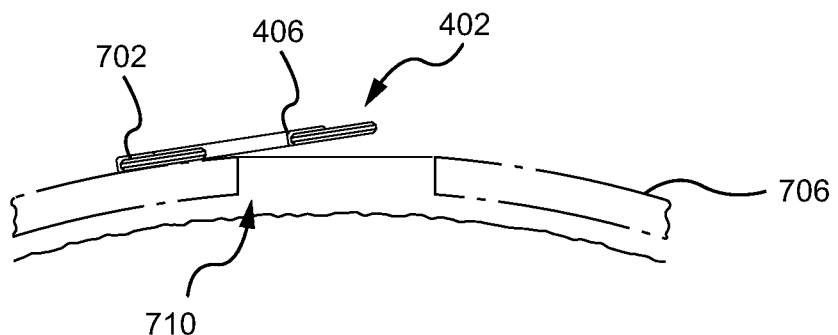
Figure 7C:
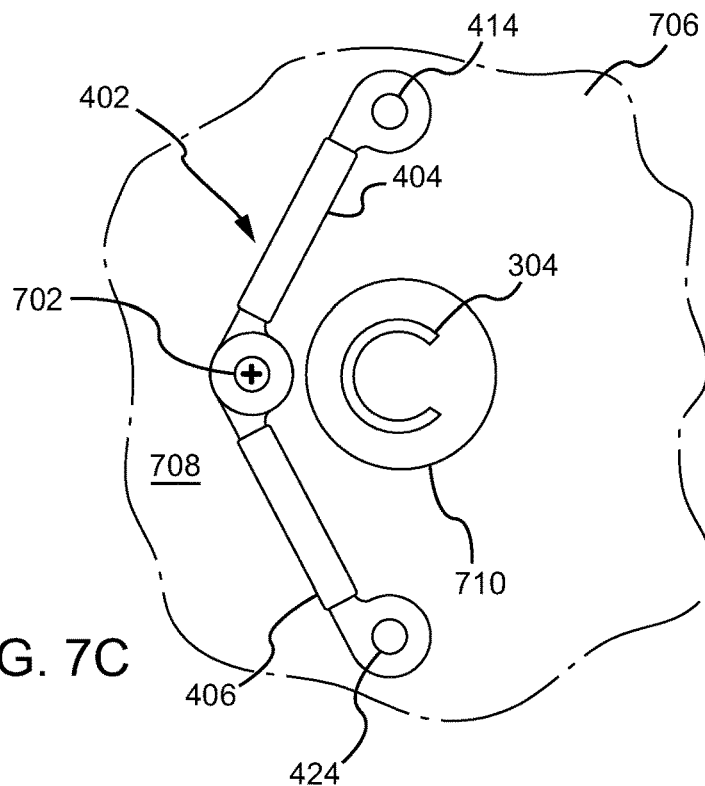
Figure 7D:
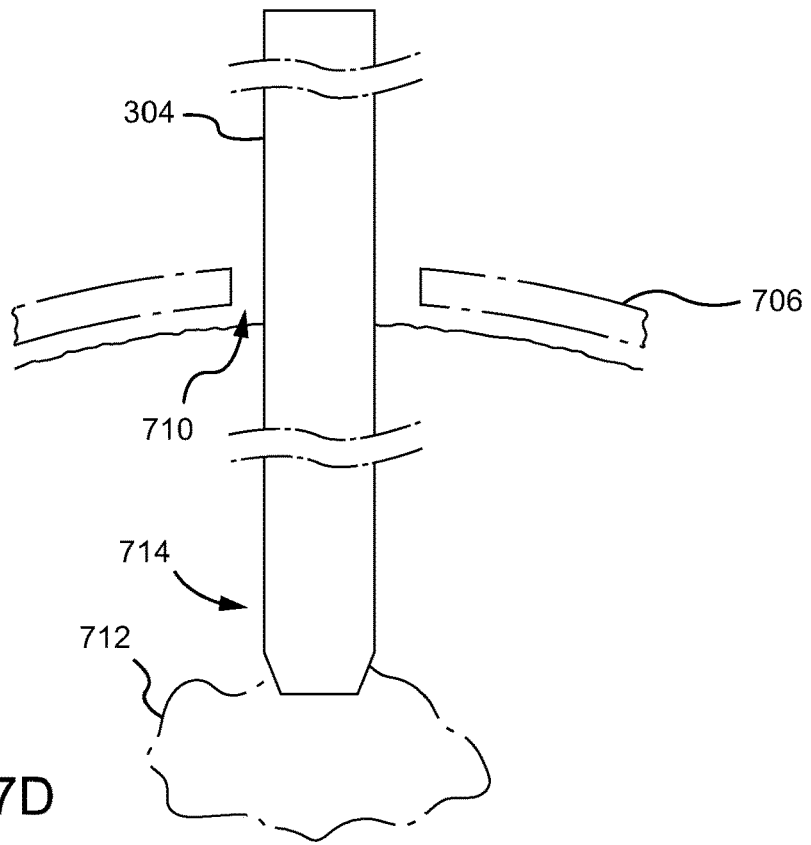
Figure 7E:
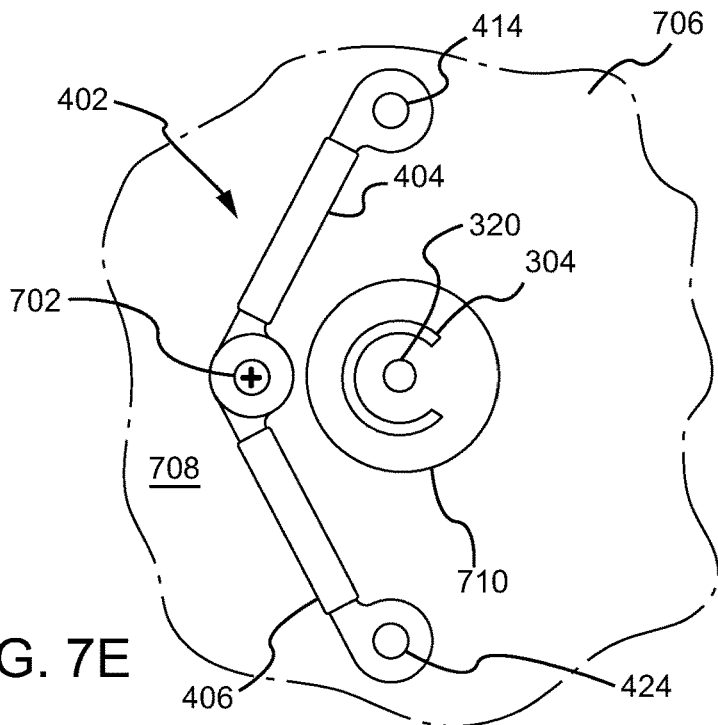
Figure 7F:
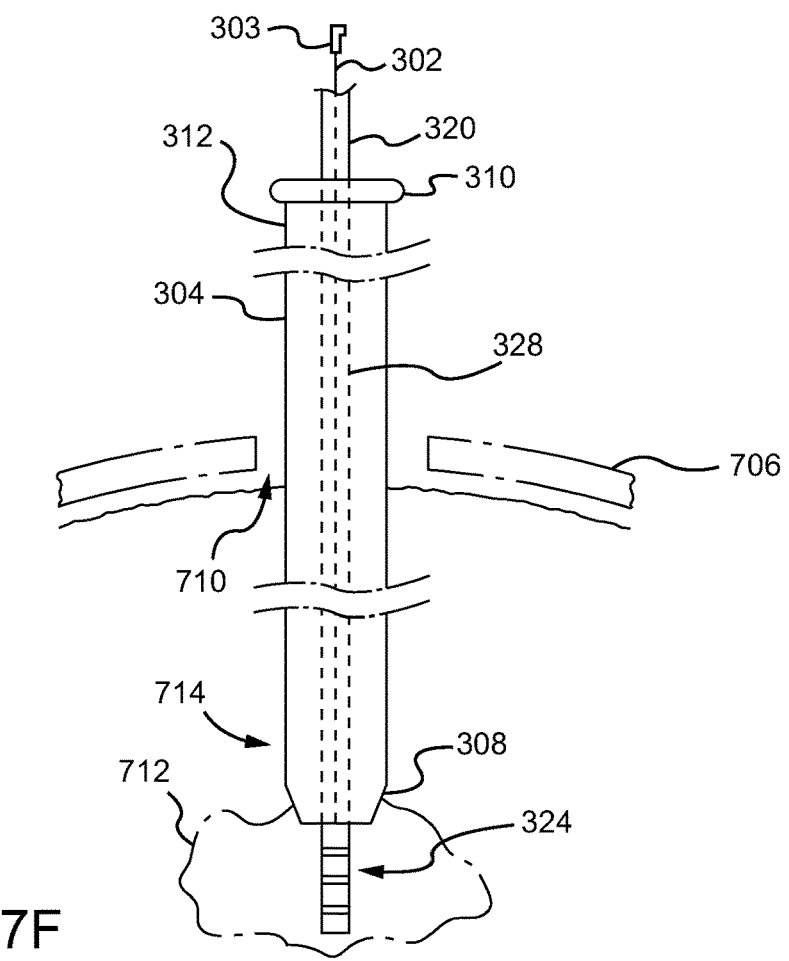
Figure 7G:
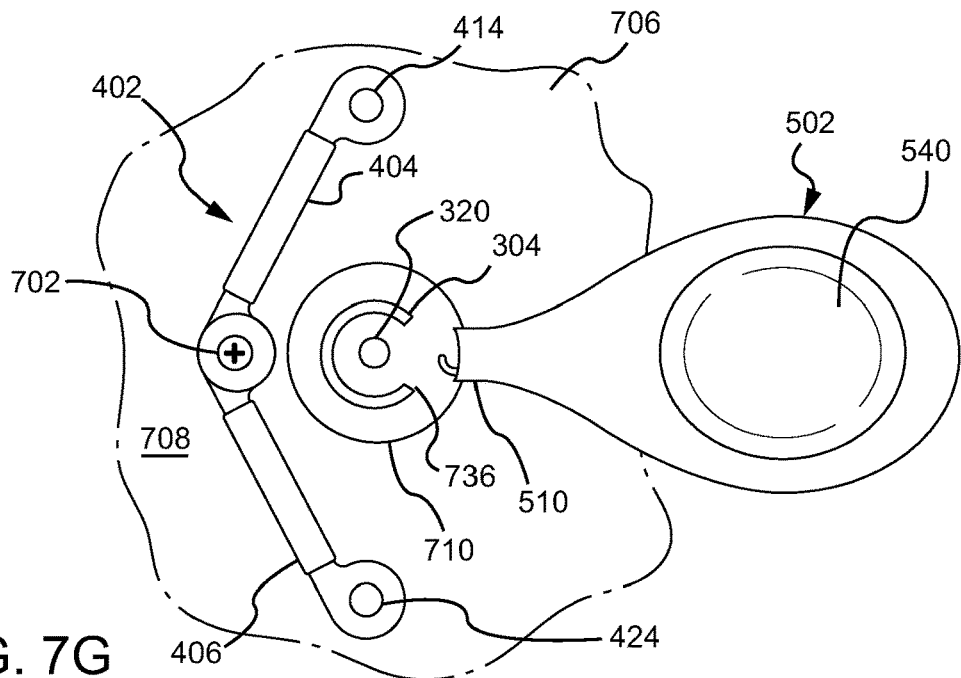
Figure 7H:
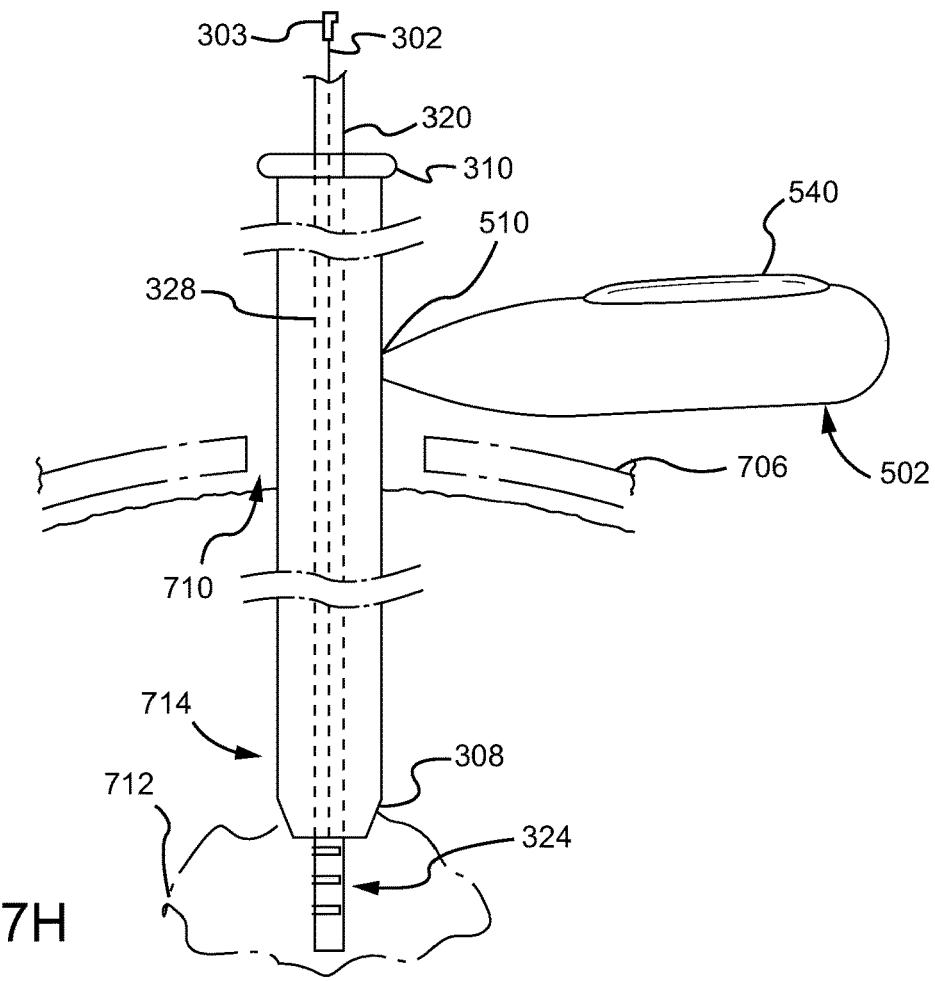
Figure 7I:
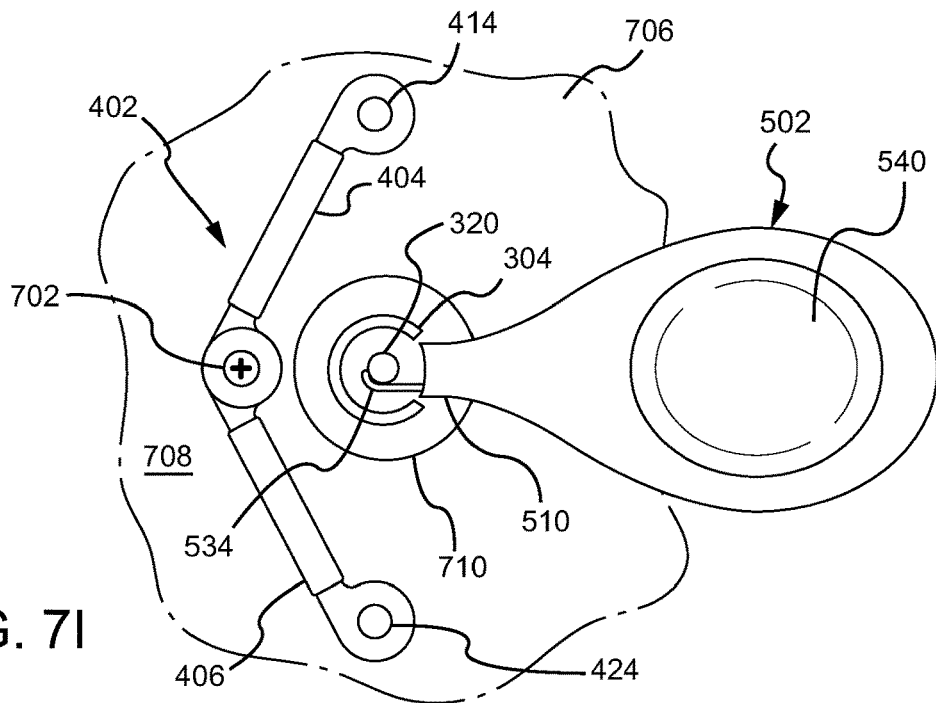
Figure 7J:
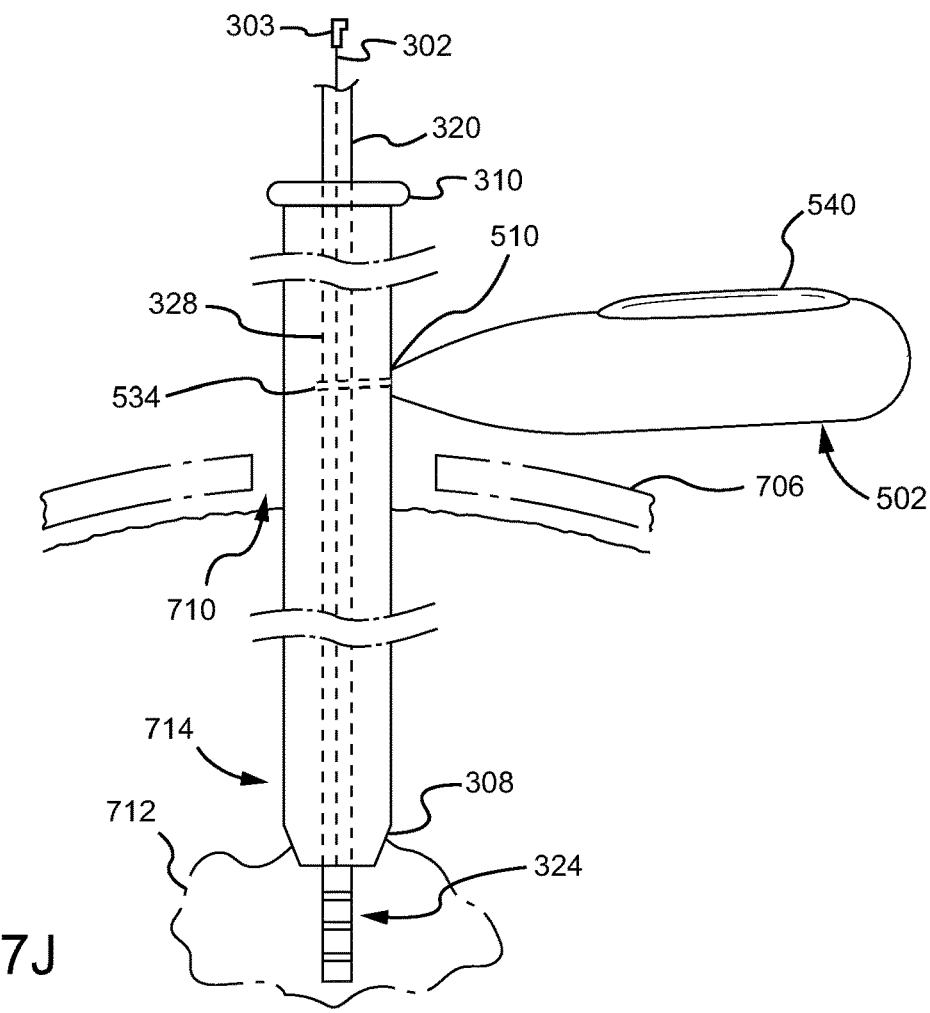
Figure 7K:
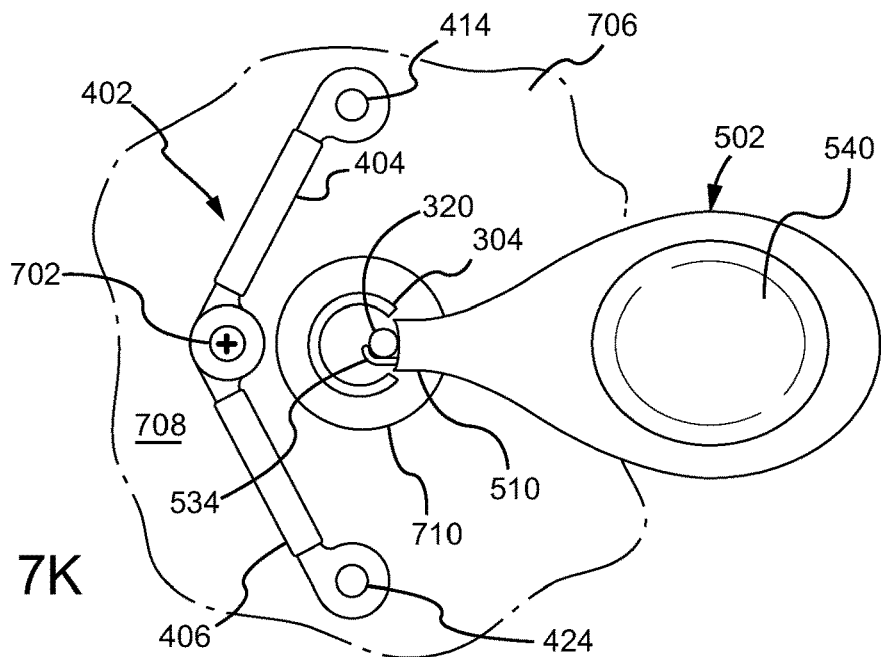
Figure 7L:
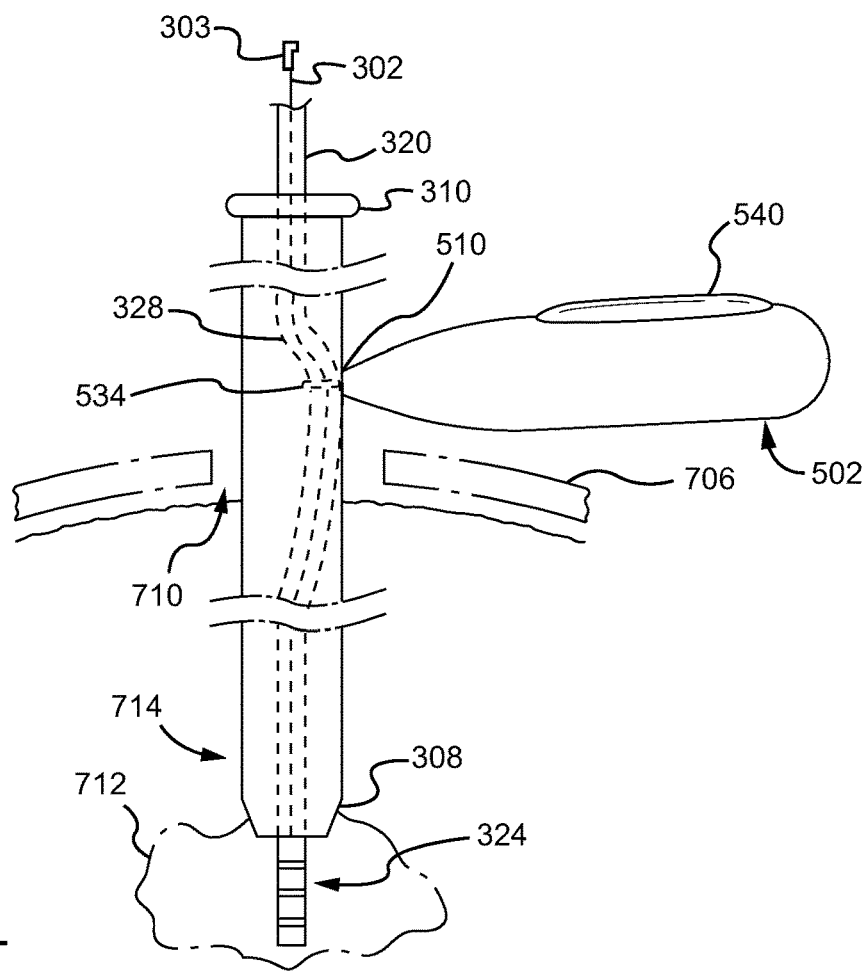
Figure 7M:
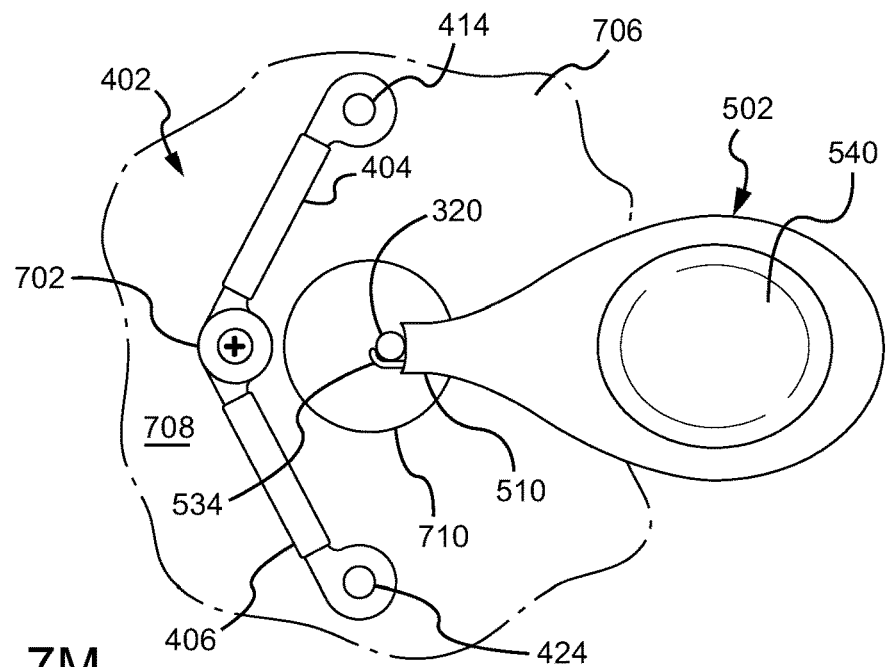
Figure 7N:
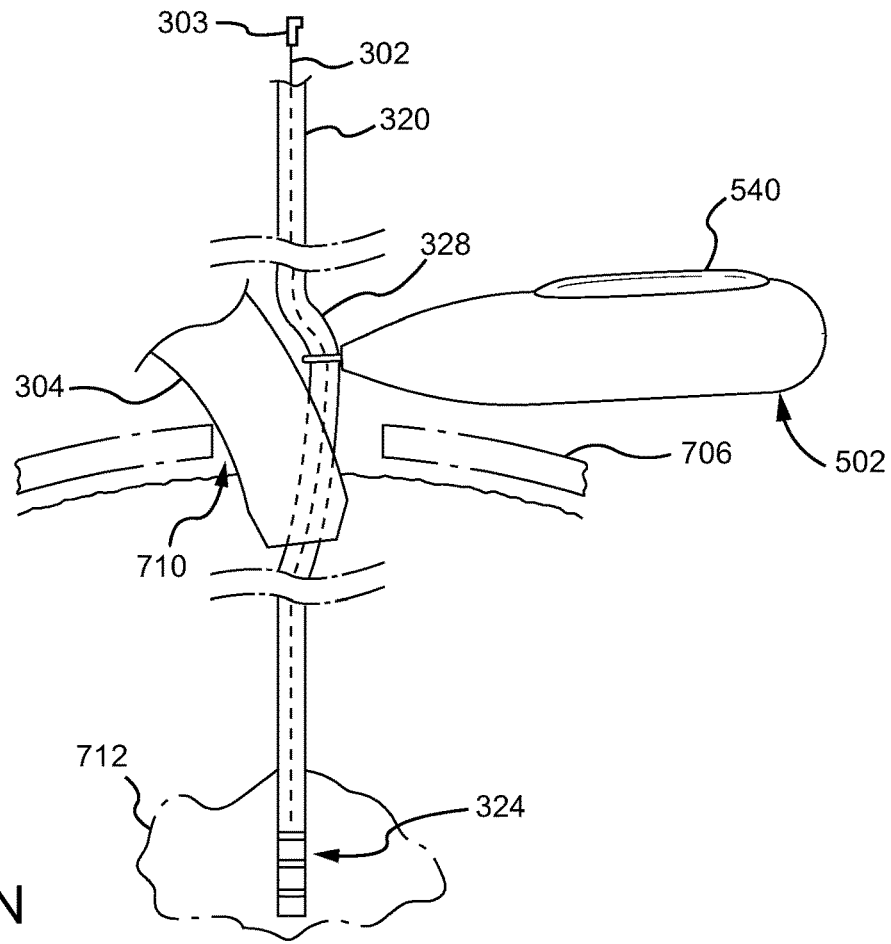
Figure 7O:
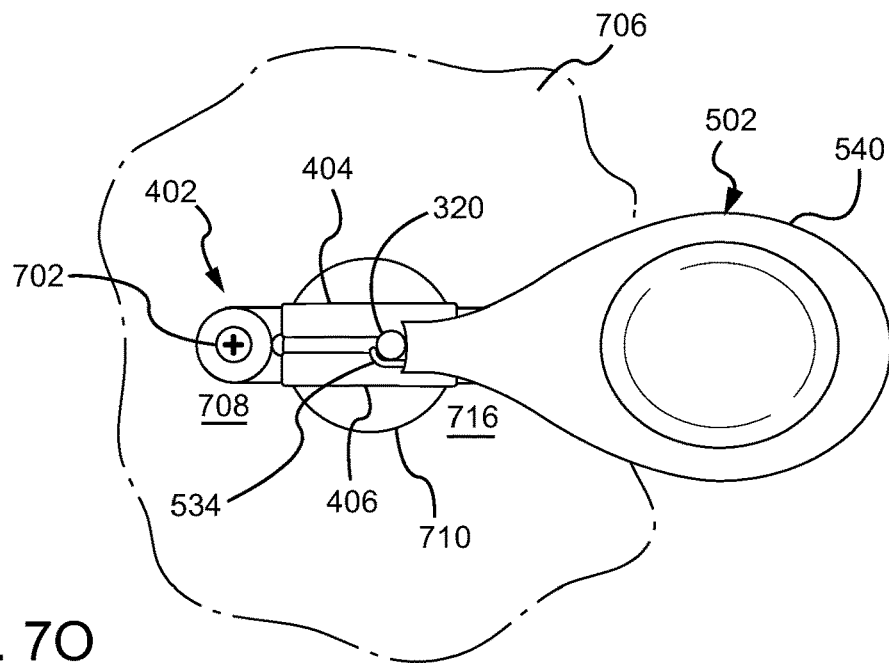
Figure 7P:
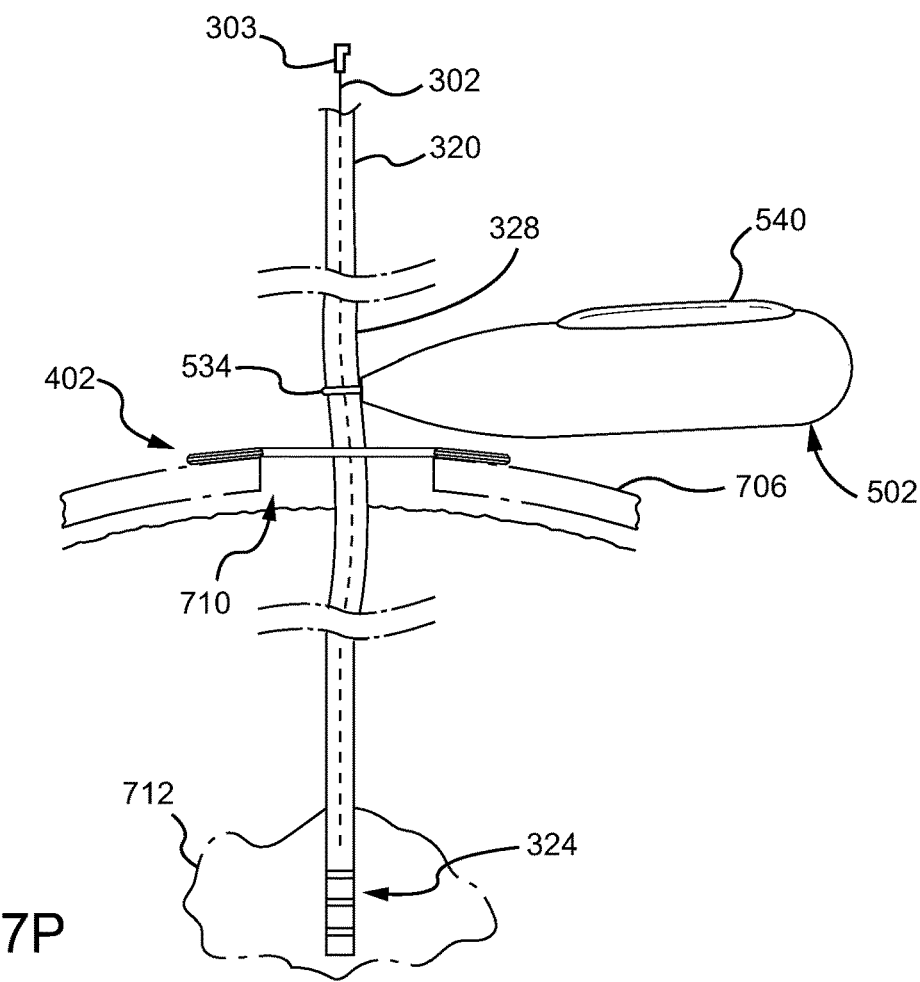
Figure 7Q:
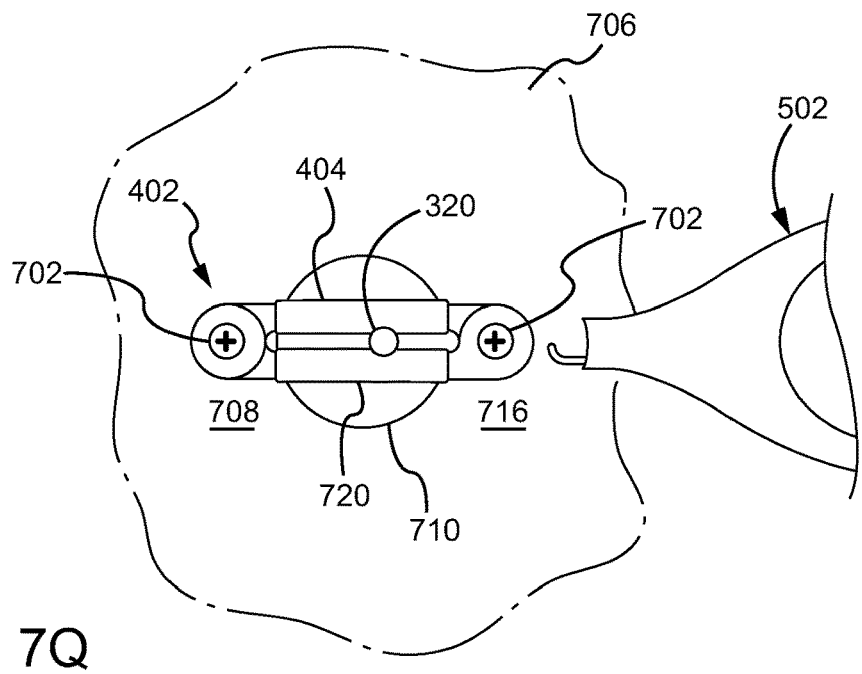
Figure 7R:
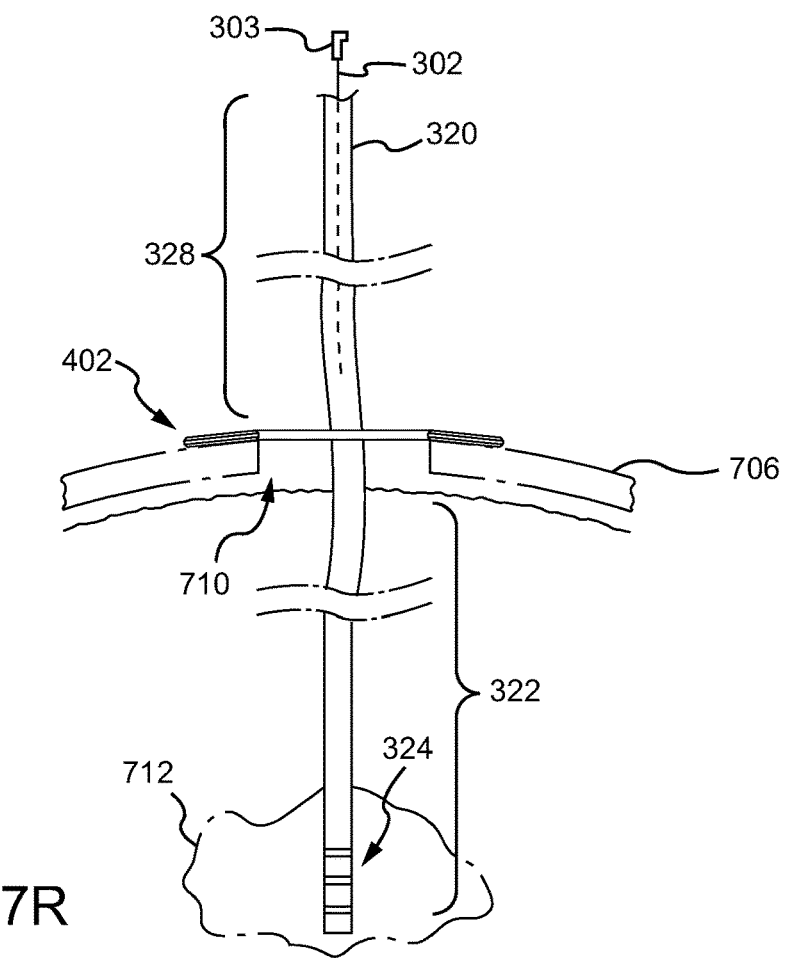

With reference to FIG. 6 and FIGS. 7A-7R, described are methods for using both the lead fixation accessory of FIGS. 4A-4E and the lead stabilization tool of FIGS. 5A-5H in a procedure to implant a brain lead.

With reference to FIG. 11 and FIGS. 12A-12D, described are methods for using the lead fixation accessory of FIGS. 9A-9G in a procedure to implant a brain lead.

Lead Fixation Accessories

A lead fixation accessory according to embodiments includes two arms that are configured to pivot around a common point, so that they can be oriented first in an open position around a skull hole to avoid obstructing access to the skull hole before a lead is implanted therethrough and second in a closed position so that the lead body can be secured relative to the skull hole once the surgeon has delivered the lead to a target. When in the closed position, respective portions, e.g., edges, of the two arms engage the lead body strongly enough to discourage relative movement of the lead between the skull hole and distally of the skull hole (i.e., the portion of the lead that is implanted in the patient), but not so strongly to impede any stiffening member disposed within an inner lumen of the lead body from moving longitudinally within the lumen, so that the stiffening member ultimately can be removed from the lead body. Described below are example configurations of lead fixation accessories that embody the foregoing design features.

With reference to FIGS. 4A-4I, a lead fixation accessory 402 includes two substantially identical arms, a first arm 404 and a second arm 406. The first arm 404 has a first end 408 with a first aperture 410, a second end 412 with a second aperture 414, and a middle region 416 that extends between the first end and the second end. Likewise, the second arm 406 has a first end 418 with a first aperture 420, a second end 422 with a second aperture 424, and a middle region 426 that extends between the first end and the second end.

Figure 4A:
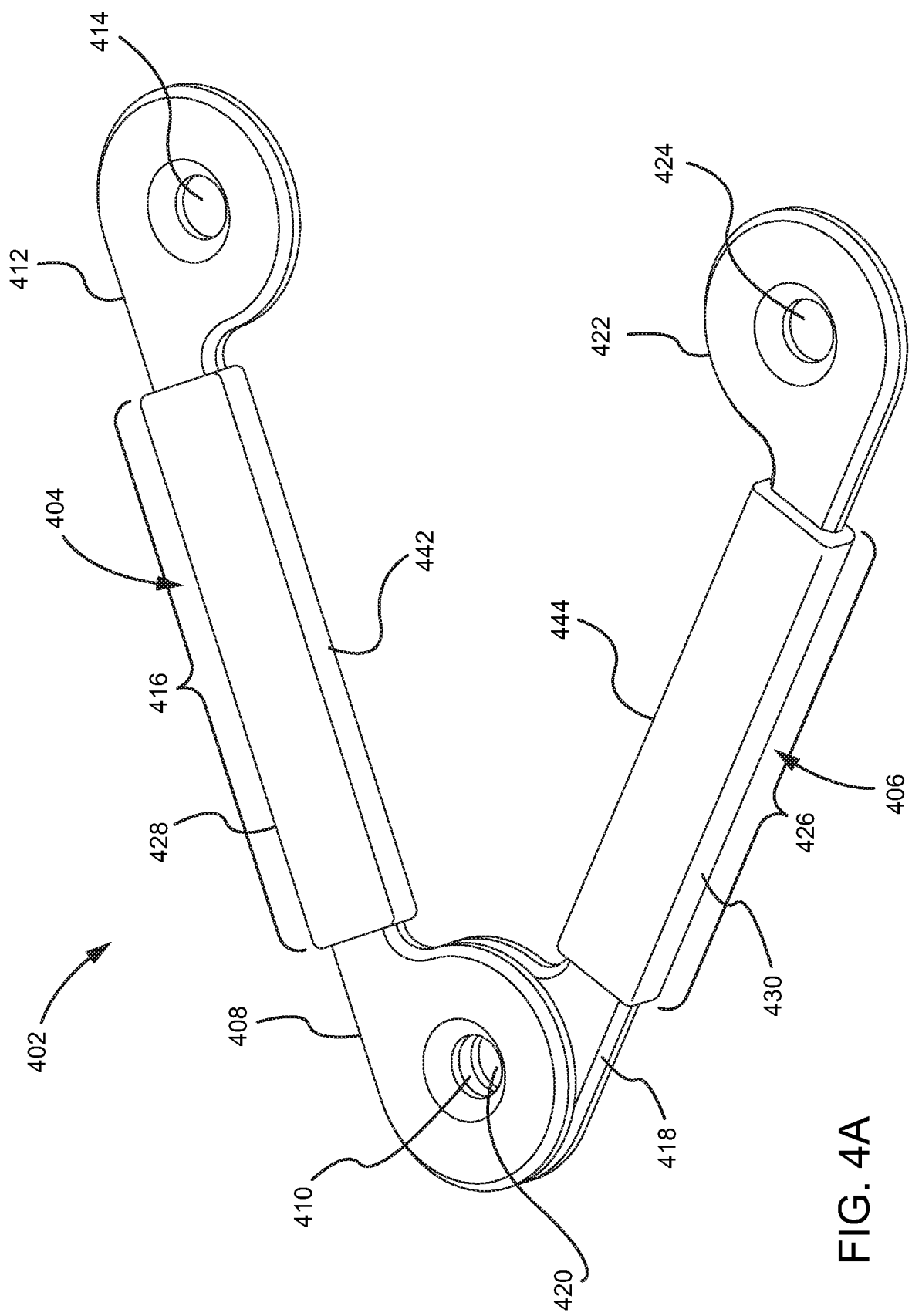
FIG. 4A is a perspective view of a lead fixation accessory according to embodiments in an open position.
Figure 4B:
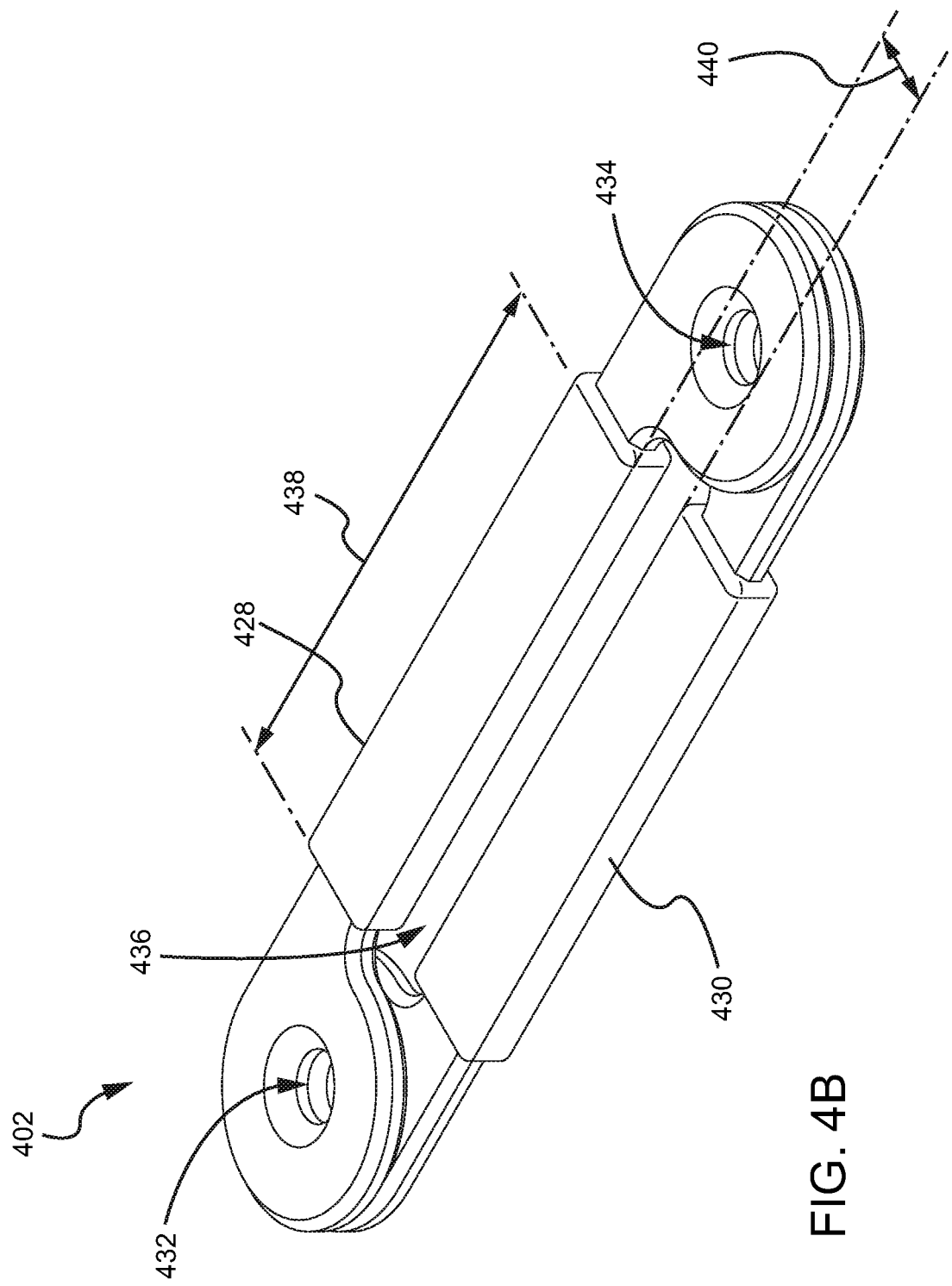
FIG. 4B is a perspective view of the lead fixation accessory of FIG. 4A in a closed position.
Figure 4C:
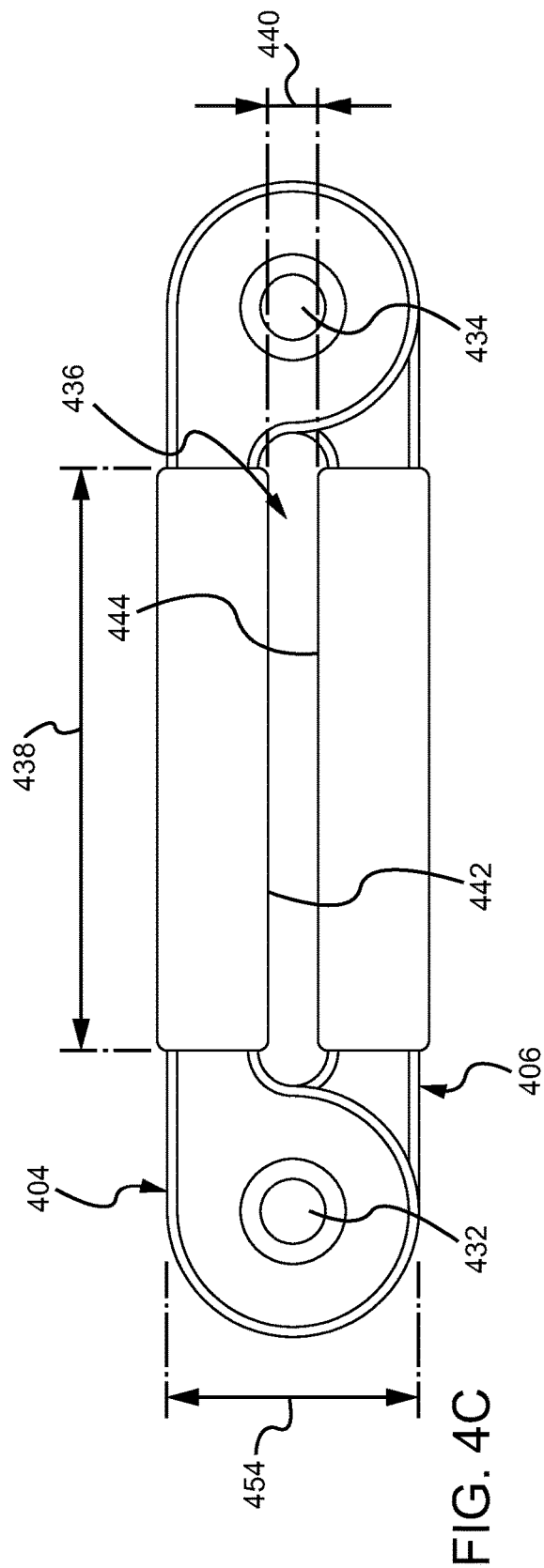
FIG. 4C is a top view of the lead fixation accessory of FIG. 4B.
Figure 4D:
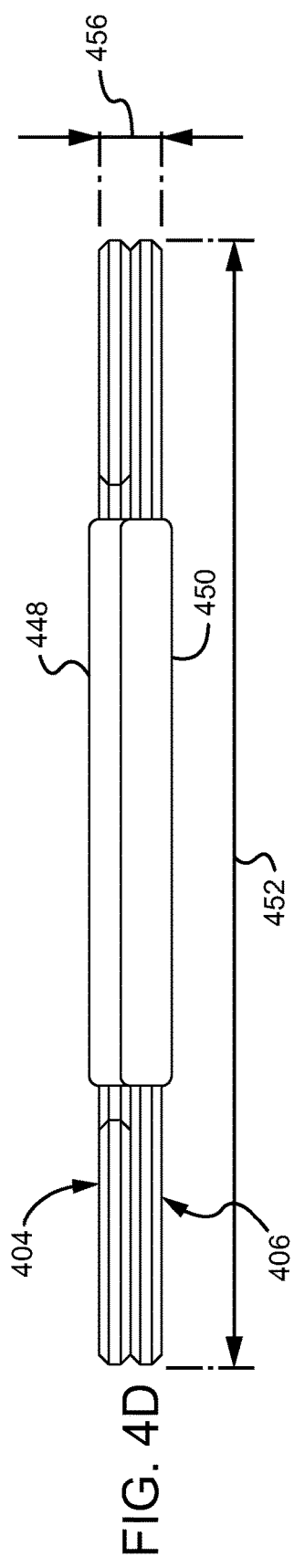
FIG. 4D is a front view of the lead fixation accessory of FIG. 4B.
Figure 4E:
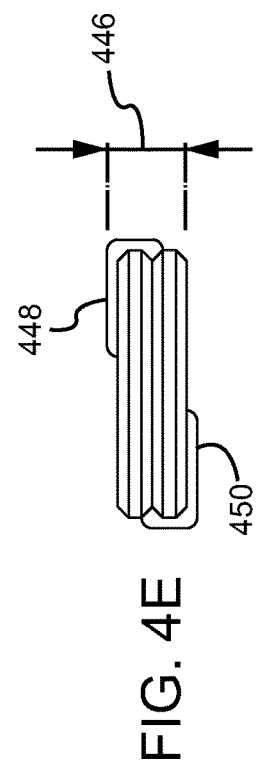
FIG. 4E is a side, end view of the lead fixation accessory of FIG. 4B.
Figure 4F:
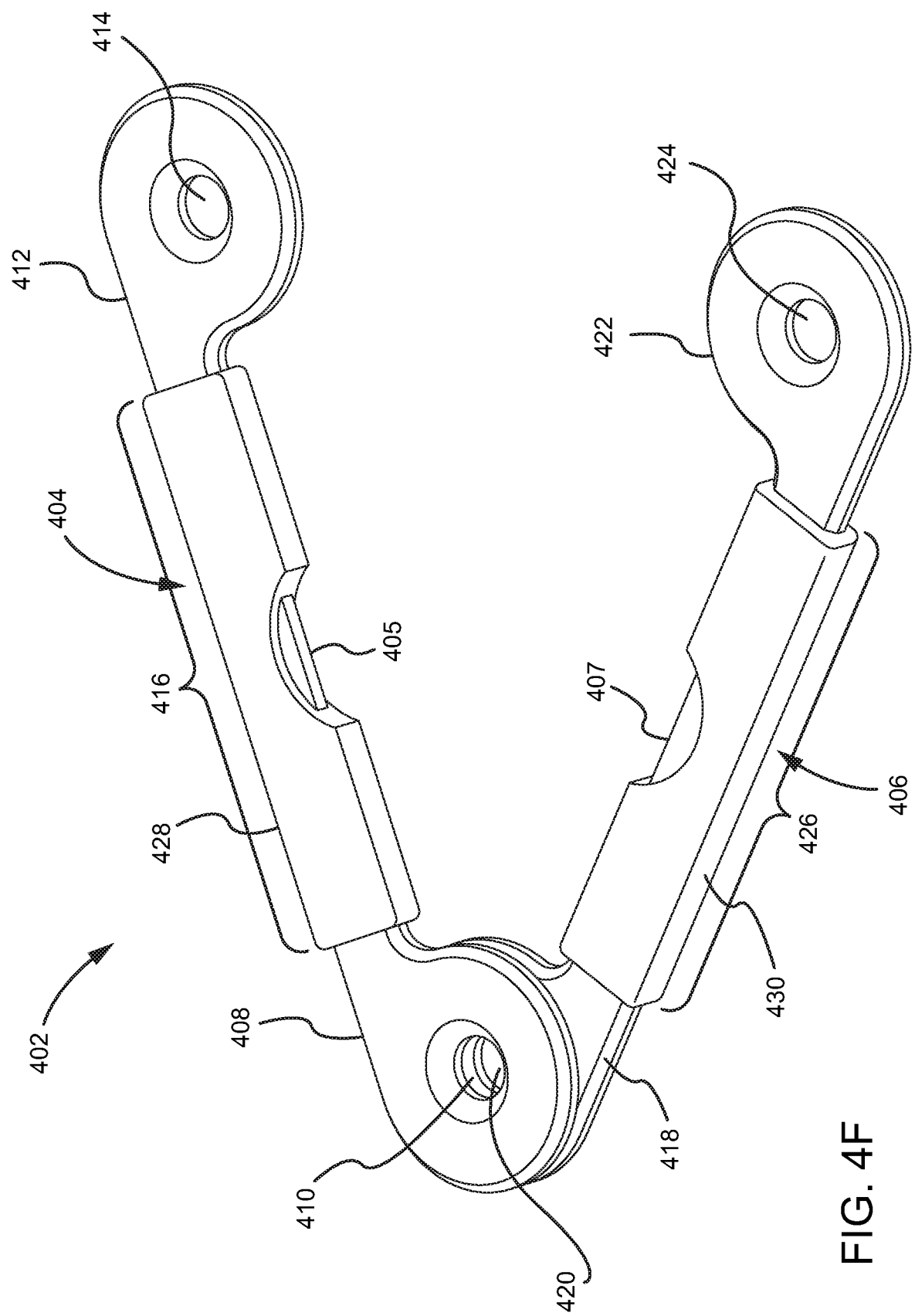
FIG. 4F is a perspective view of the lead fixation accessory of FIG. 4A with partial cutaways to expose portions of components of the accessory.

With reference to FIG. 4F, in one configuration, each of the first arm 404 and second arm 406 comprises two pieces—a core structure 405, 407 that forms the majority of the arm, and a bumper 428, 430 in the middle region 416, 426 of the arm. The bumper 428, 430 may surround, either completely or partially, the middle region 416 of the first arm and the middle region 426 of the second arm. The core structure 405, 407 may be formed of a first material having a first stiffness or hardness and the bumper 428, 430 may be formed of a second material having a second stiffness or hardness that is less than the stiffness or hardness of the first material. For example, the first material forming the core structures 405, 407 may be a biocompatible metal or alloy, such as stainless steel (e.g., 304SS), platinum, nickel-cobalt-chromium-molybdenum alloy (e.g., MP35N) or Nitinol, and the second material forming the bumpers 428, 430 may be a biocompatible polymer, e.g. 30A-80A silicone, or biocompatible plastic, e.g., polyurethane. In some embodiments, the second material forming the bumpers 428, is softer or more pliable than a silicone lead body, to provide a soft plastic/silicone-to-plastic/silicone contact interface between the accessory and the lead. This may result in a less abrasive lead-to-lead-fixation-accessory interface than is available with some other options for lead fixation accessories, such as a metal dog bone cranial plate.

Moreover, in one variation, the bumpers 428, 430 may have a specified smoothness to encourage engagement with the surface of the lead body with which they contact. For example, when silicone is very smooth, it can become tacky especially with respect to other components made of silicone, and the body of brain leads are often made of silicone. A mold for manufacturing the components of the lead fixation accessory 402 out of silicone might be specified so that the bumpers at least have a surface finish that will produce very smooth silicone for the lead-contacting surface of the bumpers, e.g., with a surface finish of either SPI.B3 or SPI.D1. Thus, the resulting smoothness of the silicone may render the lead-body contacting surface of each bumper sticky or tacky with respect to a silicone lead body, encouraging the lead body to remain between the arms while the compressive force of the arms about the lead body is varied as, for example, the attachment mechanisms are being inserted, tightened, or otherwise actuated to their final positions for the fully deployed lead fixation accessory 402.

In another configuration, each of the first arm 404 and second arm 406 comprises a single piece formed of a biocompatible polymer, e.g. 30A-80A silicone, or biocompatible plastic, e.g., polyurethane. In other words, the entirety of the arms 404, 406 is formed of the same material. In some embodiments, the material forming the arms 404, 406, is softer or more pliable than a silicone lead body, to provide a soft plastic/silicone-to-plastic/silicone contact interface between the accessory and the lead. In this variation, either the entirety of the arms 404, 406 or just the middle regions of the arms intended to engage the lead, may have a specified smoothness to encourage engagement with the surface of the lead body with which they contact.

The first arm 404 and the second arm 406 are configured to be coupled together at their respective first ends 408, 418 so that their respective first apertures 410, 420 overlap to define a first attachment hole 432 of the lead fixation accessory 402. The coupling allows for rotation of the arms 404, 406 relative to each other about an axis passing through the first attachment hole 432. When the lead fixation accessory 402 is being implanted, the major surface areas of the arms 404, 406 (as opposed to the edges of the arms) are positioned generally parallel to the surface of the skull. During rotation of an arm 404, 406, the major surface area of the arm slides over the surface of the skull, while remaining generally parallel to the skull surface.

Figure 4G:
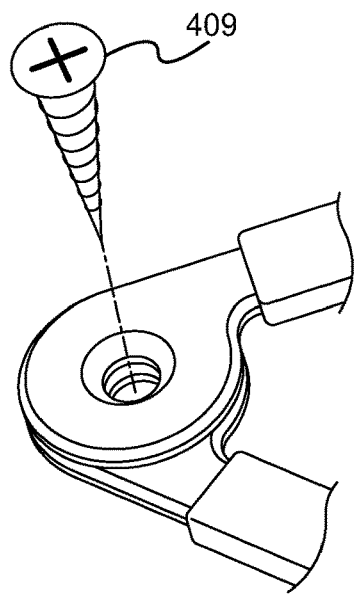
FIGS. 4G-4I are illustrations of different mechanisms for coupling components of the lead fixation accessory together to allow for rotation of the components.

With reference to FIG. 4G, in one configuration of the lead fixation accessory 402, coupling of the first arm 404 and the second arm 406 is provided by an attachment mechanism 409, e.g., a bone screw or a pin, during placement of the lead fixation accessory. The first attachment hole 432 is configured to receive the attachment mechanism 409 for attaching the lead fixation accessory 402 to the skull. During placement of the lead fixation accessory 402, the first arm 404 and the second arm 406 are positioned at a placement site, e.g., skull surface, so that their respective first apertures 410, 420 overlap to define the first attachment hole 432. Thereafter, a bone screw 409 is secured to the skull through the attachment hole 432 to thereby couple the first arm 404 and the second arm 406. To allow for rotation of the arms 404, 406, the screw 409 may be partially screwed into the skull but not screwed into the skull so tightly that the first arm 404 and the second arm 406 cannot move relative to each other.

Figure 4H:
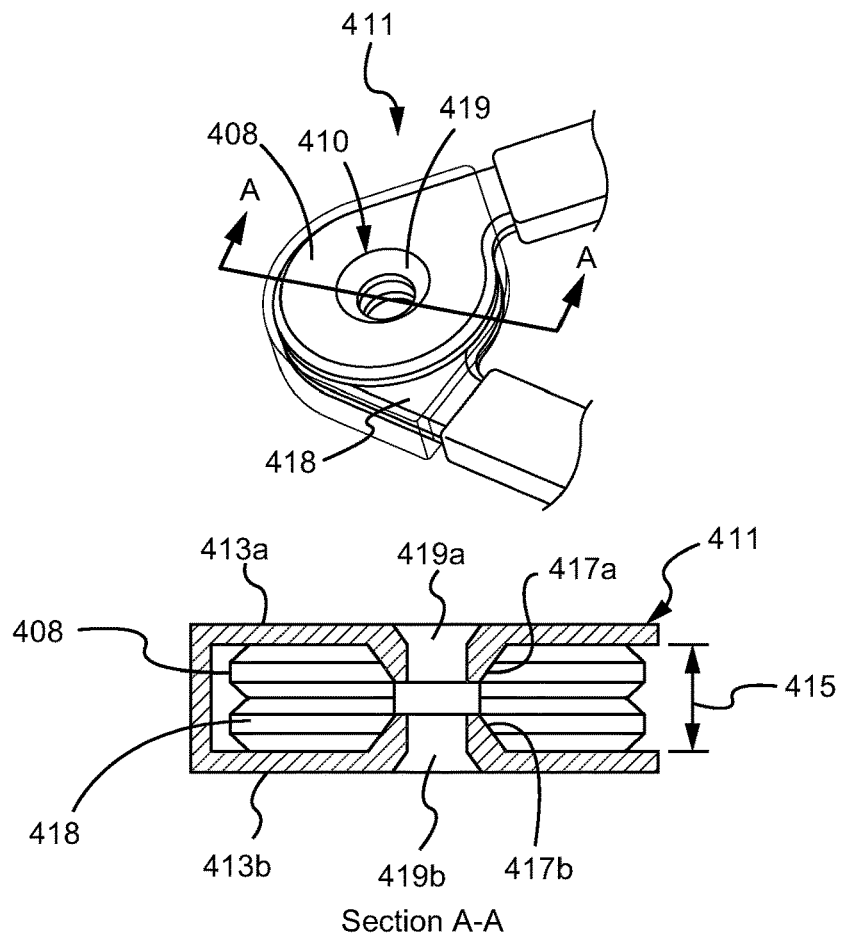
Figure 4I:
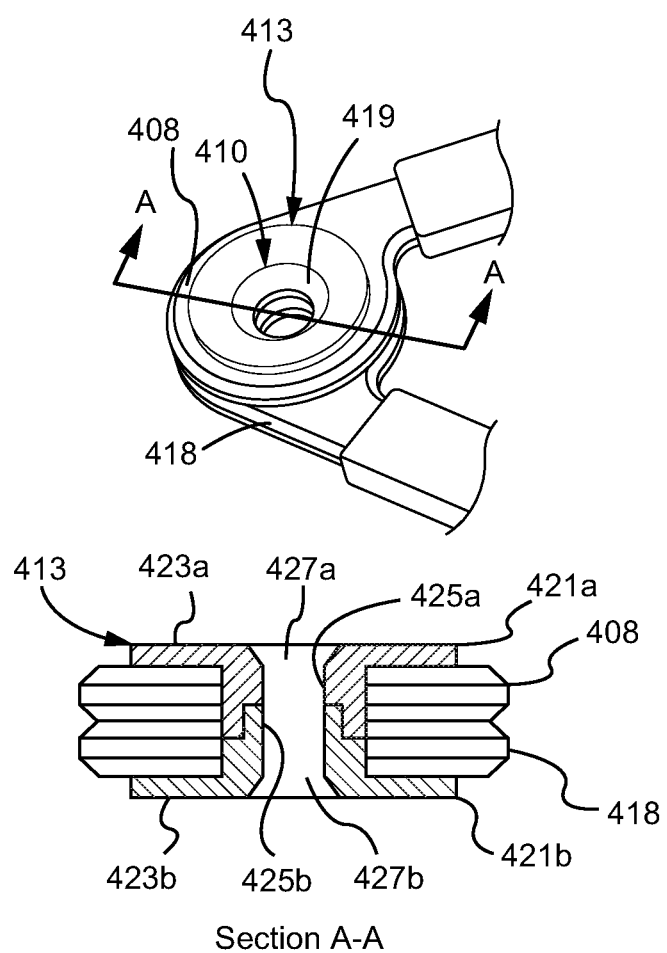

With reference to FIGS. 4H and 4I, in other configurations of the lead fixation accessory 402, coupling of the first arm 404 and the second arm 406 is provided by a hinge mechanism 411, 413 that fixedly attaches the respective first ends 408, 418 of the arms together. The hinge mechanism 411, 413 is configured to allow for rotation of the arms 404, 406 relative to each other about an axis passing through the hinge mechanism. In the configuration shown in FIG. 4H, the hinge mechanism 411 (illustrated as transparent to allow for visibility of the first ends 408, 418 of the arms) comprises a retainer having opposed faces 413a, 413b separated by a distance 415 that allows for reception of the first ends 408, 418 of the arms. Each respective face 413a, 413b includes an annular projection 417a, 417b having a size and profile that mates with the profile of annular grooves surrounding the first apertures 410, 420. The space between the opposed annular projection 417a, 417b provide a friction fit between the first ends 408, 418 of the arms thereby holding them together, while allowing for rotation of the arms relative to each other. Openings 419a, 419b extend through the respective faces 413a, 413b of the hinge mechanism 411 and are positioned to align with the first apertures 410, 420 of the arms to thereby provide a through hole for receiving a bone screw.

In the configuration shown in FIG. 4I, the hinge mechanism 413 (illustrated as transparent to allow for visibility of the first ends 408, 418 of the arms) comprises a collar having opposed annular halves 421a, 421b, each having a ring portion 423a, 423b and a cylindrical portion 425a, 425b. The cylindrical portions 425a, 425b are sized to fit through the first apertures 410, 420 of the arms 404, 406, while the ring portions 423a, 423b have a profile that mates the annular grooves surrounding the first apertures 410, 420. The thickness of the walls defining the respective cylindrical portions 425a, 425b change, for example, in a step like manner, and include features that allow for the respective cylinder portions to engage each other and snap fit together. The annular halves 421a, 421b have openings 427a, 427b that align to thereby provide a through hole for receiving a bone screw.

Returning to FIGS. 4A-4F, the lead fixation accessory 402 without an attachment mechanism in the attachment hole 432 is shown in an open position in FIG. 4A and in a closed position in FIG. 4B. One of the arms 404 is oriented on top of the other of the arms 406 such that the first end 408 of the first arm 404 overlays the first end 418 of the second arm 406. The first aperture 410 in the first arm 404 is lined up with the aperture 420 in the second arm 406 to form the attachment hole 432. Coupled as such, the respective seconds ends 412, 422 of the arms 404, 406 may be moved relative to each other to thereby provide an open state of the lead fixation accessory 402, during which the respective second ends are displaced from each other, and a closed state, during which the respective second ends and the respective second apertures 414, 424 of the first and second arms overlap to define a second attachment hole 434.

When an attachment mechanism like a bone screw is situated in the attachment hole 432 and at least partially engaged with the skull to anchor the lead fixation accessory 402 to the patient, the two arms 404, 406 of the device can pivot 360° in a plane around the attachment mechanism. Thus, before a lead is implanted in the skull hole, the two arms 404, 406 can be attached to the skull with the attachment mechanism securely enough to keep them on the patient, but loosely enough to move them out of the way of the skull hole while the lead is being delivered to the target. This feature allows (but does not require) the lead fixation accessory to be partially attached to the skull surface before a lead is introduced into the skull hole.

More particularly, early in the implant procedure, the lead fixation accessory can be secured to the skull in the vicinity of the skull hole in an open position, which does not impede access to the skull hole, or interfere with other implant equipment, e.g., the stereotactic equipment, the slotted cannula, or the lead itself. Later in the implant procedure, when only the lead (with a lead stylet inserted therein) remains at the skull hole, the lead fixation accessory is closed and affixed to the skull with the other attachment mechanism, to secure the lead in place while allowing for removal of the stylet. The lead fixation accessory is thus beneficial in that it secures the lead in place at the skull hole while the stylet is removed from the lead.

However, because the lead fixation accessory does not include a component that has to be situated in a burr hole before a lead is implanted through the burr hole, it can also be deployed to secure a lead body relative to a skull hole after the lead has been implanted. Thus, while it no doubt often will be more convenient to attach one component of the two-piece lead fixation accessory after the skull hole is formed but before the procedure to implant a lead therethrough is commenced, it will be appreciated that it also is possible to deploy the lead fixation accessory after the lead has been delivered to the target, since neither of the two pieces needs to be situated in the skull hole itself.

To allow the lead fixation accessory to be closed and secured at both ends to the skull surface, like the first attachment hole 432, the second attachment hole 434 is configured to receive an attachment mechanism (not shown), e.g., a bone screw or pin, for securing the lead fixation accessory 402 to the skull at the second ends 412, 422 of the arms 404, 406 when it is in a closed position and oriented around the body of a lead that has been implanted in a skull hole. When the surgeon has the lead body situated with the desired force between the two arms, the attachment mechanisms in both attachment holes 432, 434 can be tightened down against the skull to maintain the force and to compress the lead body strongly enough to discourage the lead from pulling away from the target but, if the lead has a stiffening member like a stylet disposed in an inner lumen, not so strongly as to prevent the stylet from being withdrawn and removed from the lead.

It will be appreciated from the foregoing that the features of a given instance of a lead fixation accessory according to embodiments may be selected in part based on the variety of diameters of skull hole the accessory is intended to be used with and in part on the characteristics of the lead (s) the lead fixation accessory will be securing (e.g., whether the lead has a removably stiffening member, the material from which the lead body is formed, how and where the electrical conduits for any electrodes are situated in the lead, etc.).

FIGS. 4B and 4C illustrate the lead fixation accessory 402 in a closed position (attachment mechanisms and lead not shown). In this position, the first arm 404 and the second arm 406 form an elongated opening 436 having a length 438 and a width 440. The length 438 generally corresponds to the length of the middle region 416 of the first arm and the middle region 426 of the second arm. The width 440 generally corresponds to a distance between an inner edge 442 of the middle region 416 of the first arm 404 and an inner edge 444 of the middle region 426 of the second arm 406. The width should be selected so that when the two arms are closed around a lead body, the lead body can be held securely within the lead fixation accessory 402 when the attachment mechanisms are inserted into the respective attachment holes 432, 434, but not so securely as to compress the lead body overmuch to (1) prevent withdrawal of any stiffening member or (2) compromise the integrity of the lead (e.g., electrical connections for electrodes).

Thus, the width defined by the inner edges 442 and 444 will depend on the nature of the lead the lead fixation accessory 402 is intended to be used with, for example, on the outer diameter of the lead, whether it has any inner lumens, and how much it can be compressed without preventing removal of a stylet or compromising the lead integrity. For example, brain leads may have a diameter of only 1.27 mm, and an inner lumen in which a stylet is slidably disposed. It would be undesirable to close the lead fixation accessory 402 around the lead with enough force to impede movement of the stylet within the inner lumen. The smallest width between the two arms when the lead fixation accessory is in a closed position may be specified to discourage that scenario.

Other brain leads provide the conductors that allow each electrode at the distal end of the lead to be in electrical communication with a connector at the proximal end of the lead in a coil that surrounds the inner lumen for the stylet. (For a lead design having a stylet inner lumen surrounded by a conducted coil, see, e.g., U.S. Pat. No. 7,146,222 to Boling et al for Reinforced Sensing and Stimulation Leads and Use in Detection Systems). If the lead fixation accessory is intended for use with this type of lead, the smallest width between the two arms in a closed position may be specified to permit even less compression of the lead body, so that the integrity of the coil surrounding the stylet lumen is not compromised. For example, for a 1.27 mm diameter lead with a stylet inner lumen surrounded by a coil, the recommendation may be to avoid chronically compressing the lead body more than 20%, such as when securing the lead at a skull hole. In this case, the lead fixation accessory 402 may be specified so that the minimum width between the two arms 404, 406 when the accessory is in a closed position is not less than 1.02 mm (or 20% of 1.27 mm).

In specifying the dimensions of the lead fixation accessory, for example, the length of the arms, the dimensions can be varied so that the accessory has a small footprint and a low profile (above the skull surface when installed), but nevertheless can be used with a wide variety of diameters of skull hole. A limiting factor may be the largest diameter skull hole with which the accessory is intended for use, such that each arm must be at least as long as the largest diameter skull hole with enough extra length to allow the arms to be affixed to the skull on either side of the skull hole. Of course, the lead fixation accessory can be manufactured in different sizes, to permit use with different maximum skull hole diameters. In one embodiment, because most depth lead implant procedures involve either of a 14-mm burr hole or a 3.2 mm twist hole, the lead fixation accessory is designed so that the length 438 of the middle regions 416, 426 of the first and second arms 404, 406 is greater than 14 mm, such as 16.5 mm. Of course, another variation may be intended for use with twist drill holes of less than 5 mm diameter, in which case, the length 438 may be more on the order of 5.7 mm.

Further, the first arm 404 and the second arm 406 of the lead fixation accessory 402 may be dimensioned so that the overall length 452 of the accessory places each of the first and second attachment holes 432, 434 a sufficient distance from the edge of the skull hole so that skull surface is beneath the attachment holes when the device is centered over the skull hole. This design ensures that any attachment mechanism used, such as bone screws, inserted through the attachment holes 432, 434, may be fully engaged with the skull and will not overlap with the skull hole. For example, in a particular configuration of the lead fixation accessory where the length 438 of the middle region 416 is approximately 16.5 mm, the overall length 452 of the lead fixation accessory 402 is approximately 29 mm.

The lead fixation accessory 402 may be designed to have a lower profile, relative to other known lead fixation devices, that renders the accessory less noticeable by touch and sight to the patient and others. As described above, after a lead is implanted through a skull hole, a portion of the lead extends proximally of the skull hole, for example, until the proximal end of the lead is connected to another implanted device, such as the neurostimulator implanted in a tray in the skull described above with reference to FIG. 1A. When a chronic connection of the proximal end of the lead is intended, the scalp is usually replaced to cover the skull hole and any portion of the lead extending proximally of the lead on the skull. The patient often can feel the lead and sometimes the skull hole with a finger even after the scalp is replaced over the skull. It is generally undesirable for the patient to fiddle with the skull hole or the proximally extending lead under the scalp, because doing so might dislodge the lead from the target or compromise the connection at the proximal end of the lead. So, generally the lower profile the lead fixation accessory can be the better.

A lead fixation accessory 402 according to embodiments will extend above the patient's skull to some degree, by the height of the stacked first ends 408, 418 and the stacked second ends 412,422, the height of any attachment mechanism (e.g., the head of a bone screw), and the height of the lead just proximal of the lead fixation accessory 402. But other known lead fixation accessories present an even higher profile when the device is installed and secured with a lead. For example, some burr hole covers are designed such that a portion of the cover extends above the surface of a skull after implant. The more the burr hole cover extends above the skull surface the more the patient is likely to be annoyed by the burr hole cover, to fiddle with it, and to be self-conscious about how it affects their appearance. The lead fixation accessory disclosed herein avoids these disadvantages of the known burr hole covers in that it is designed to have a lower profile that is less noticeable to the patient and others, and is thus more comfortable and aesthetically pleasing.

In addition, when the lead fixation accessory is used with a smaller-diameter twist drill hole, the arms 404, 406 will cover most if not all of the skull hole. When a lead fixation plate such as the cranial plate 154 shown in FIG. 1A is used, the lead is secured to the side of the skull hole, leaving the hole open except for the lead extending out of it. The patient may be able to feel the hole, and may fidget with it, perhaps moving the lead around, and pushing it further into the hole. The lead fixation accessory disclosed herein reduces the likelihood that a lead will be abused in this way insofar as the accessory at least partially covers the skull hole and thus provides a physical barrier between the scalp and the skull hole. Thus, a patient may be less likely to fiddle with the skull hole if the lead fixation accessory according to embodiments is disposed over the twist drill hole instead of to the side of it.

For a low profile, the lead fixation accessory 402 may be designed to have a maximum height 446 between a top surface 448 (of first arm 404 in FIG. 4D) and a bottom surface 450 (of second arm 406 in FIG. 4D) that is less than the distance from the top of a typical burr hole cover to the skull surface. For example, some burr hole covers are configured such that the top surface of the cover lies between approximately 0.1 mm and 0.2 mm above the skull surface. Accordingly, in one design of the lead fixation accessory 402, the maximum height 446 of the lead fixation accessory 402 is less than 0.1 mm, and in one particular configuration is 0.084 mm.

A lead fixation accessory according to embodiments that is dimensioned to traverse the diameter of a burr hole (usually ≥5 mm, typically 14 mm) will also traverse the smaller diameter of a twist drill hole (usually <5 mm, typically 3.2 mm). In addition, no component of the lead fixation accessory need be installed in or at the skull hole before the procedure to implant a lead has begun (although it may be convenient to anchor the accessory at one of the two attachment holes 432, 434 with an attachment mechanism beforehand, so it is ready to be manipulated into a closed position once the lead has been delivered to the target). Further, and although it is anticipated that most of the time, the lead fixation accessory will be used to traverse a skull hole, it may be used to the side of a skull hole, as with the cranial plate 154 shown in FIG. 1A. For example, if the lead is a cortical strip lead type and the hole through which the lead is implanted is the craniectomy in which a tray 112 and neurostimulator 110 are later situated, then the surgeon may want to anchor the proximal portion of the lead to the skull between the craniectomy and the point where the lead is connected to the connector 114 of the neurostimulator. The surgeon could adjust the lead fixation accessory 402 at an angle so that it could accommodate the lead body and attach to the skull with attachment mechanisms through the attachment holes 432, 434, even if the arms 404, 406 are not traversing a skull hole. Thus, a lead fixation accessory according to embodiments can be adapted to secure leads of different types in different positions on the skull relative to skull holes of different diameters to achieve the function of discouraging movement of the lead away from the target.

With reference to FIGS. 9A-9E, in another embodiment, a lead fixation accessory 402 for securing a lead to a skull includes a first arm 404 and a second arm 406. Each of the first arm 404 and second arm 406 may be formed of a biocompatible polymer, e.g. 30A-80A silicone, or biocompatible plastic, e.g., polyurethane or polyetheretherketone (PEEK). The first arm 404 has a first end 408, a second end 412 having an engagement feature 906, and a middle region 416 that extends between the first end and the second end. The middle region 416 includes one or more apertures 902 sized to receive an attachment mechanism, e.g., bone screw, that is configured to penetrate the surface of the skull to secure the first arm to the skull. The second arm 406 also has a first end 418, a second end 422 having an engagement feature 908, and a middle region 426 that extends between the first end and the second end. The middle region 426 of the second arm may or may not include one or more apertures 902 sized to receive an attachment mechanism to secure the second arm to the skull. Each of the first arm 404 and the second arm 406 is characterized by a thickness T and a surface area. When the lead fixation accessory 402 is implanted, the surface areas of the arms 404, 406 are positioned generally parallel to the surface of the skull. The surface area may be generally send-circular in shape, as shown in FIGS. 9A-9E, or may be any other geometric shape.

The first arm 404 and the second arm 406 are coupled together at their respective first ends 408, 418 by a coupling mechanism 904, such as a hinge pin. Coupling provided by the hinge pin 904 allows the respective second ends 412, 422 of the arms 404, 406 to be moved relative to each other to thereby provide an open position or state of the lead fixation accessory 402 (shown in FIGS. 9A and 9E) and a closed position or state of the lead fixation accessory (shown in FIGS. 9B-9D). During movement of an arm 404, 406, the surface area of the arm slides over the surface of the skull, while remaining generally parallel to the skull surface. While in an open position, the respective second ends 412, 422 are displaced from each other. In a closed position or state, the respective second ends of the first and second arms are mechanically coupled together by engagement of their respective engagement features 906, 908, and the respective middle regions 416, 426 of the arms form an opening 436 sized to secure the lead in place. In one configuration, the engagement features may include a detent 908 and a detent port 906 sized to mate with the detent.

Regarding the opening 436, each of the middle regions 416, 426 includes an inner edge 442, 444, having a contour feature that defines a geometry of the opening 436. For example, the inner edge 442 of the first arm 404 has an arcuate cutout 910, while the inner edge 444 of the second arm is linear and devoid of any cutouts. Configured as such, the inner edges 442, 444 form an opening 436 having a semicircular geometry when the lead fixation accessory 402 is in a closed position. Many other geometries are possible, for example, each of the inner edges 442, 444 may have an arcuate cutout to form an opening having a circular geometry, or a rectangular cutout to form a rectangular opening. Furthermore, an inner edge 442, 444 may have more than one cutout 910 to form more than one opening 436.

Figure 9A:
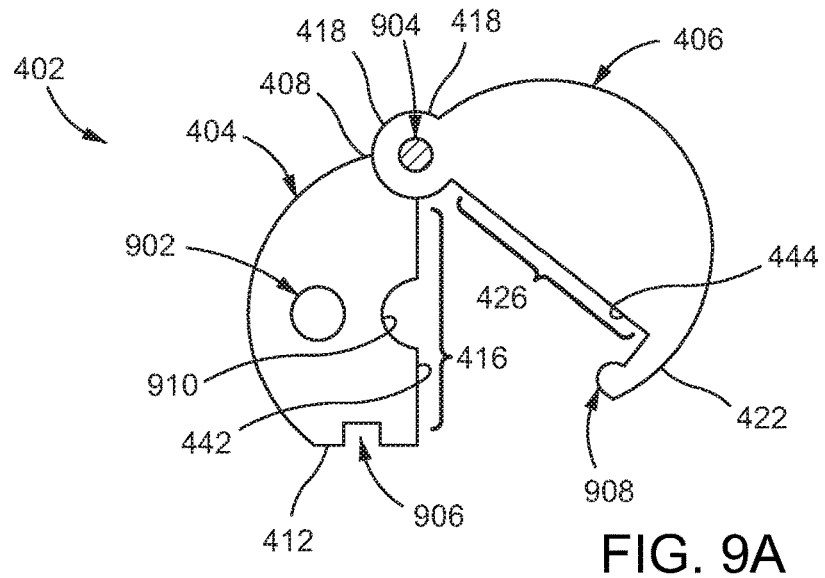
FIG. 9A is a top view of a lead fixation accessory according to embodiments in an open position.
Figure 9B:
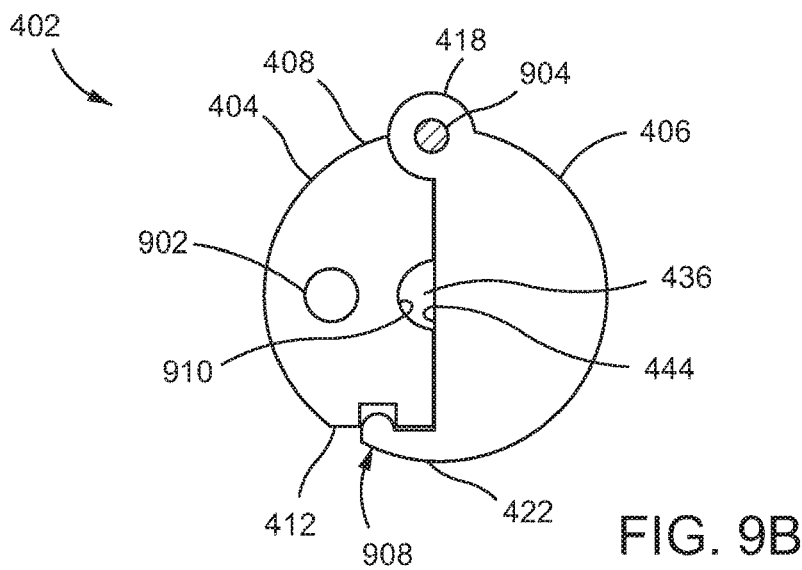
FIG. 9B is a top view of the lead fixation accessory of FIG. 9A in a closed position.

With reference to FIG. 9B, the opening 436 has a dimension D corresponding to a distance between the inner edges 442, 444 that define the opening. The dimension is designed to provide an interference fit between the inner edges 442, 444 and a lead, sufficient to secure the lead in place without damaging the lead. The dimension may be described in various ways depending on the geometry of the opening 436. For example, the dimension may be described as a radius (in case of a semicircular geometry), a diameter (in case of a circular geometry), or a width (in case of a rectangular geometry).

Figure 9C:
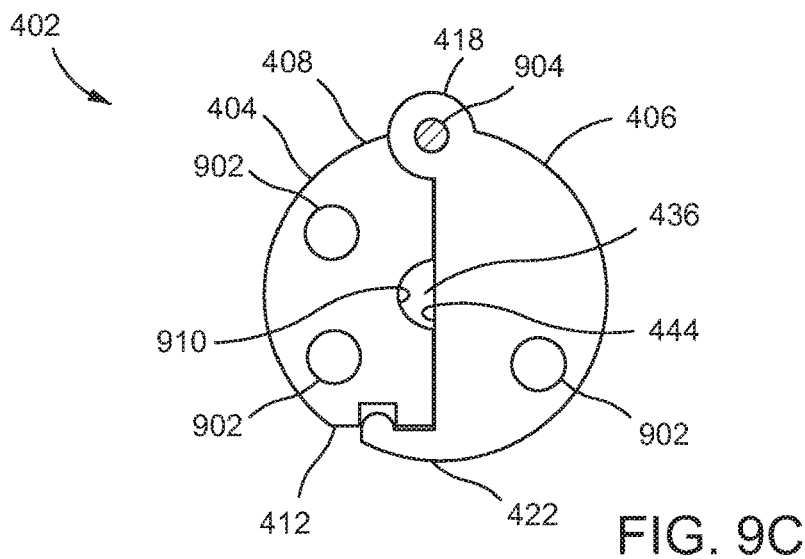
FIG. 9C-9E are top views of different configurations of the lead fixation accessory of FIGS. 9A and 9B.
Figure 9D:
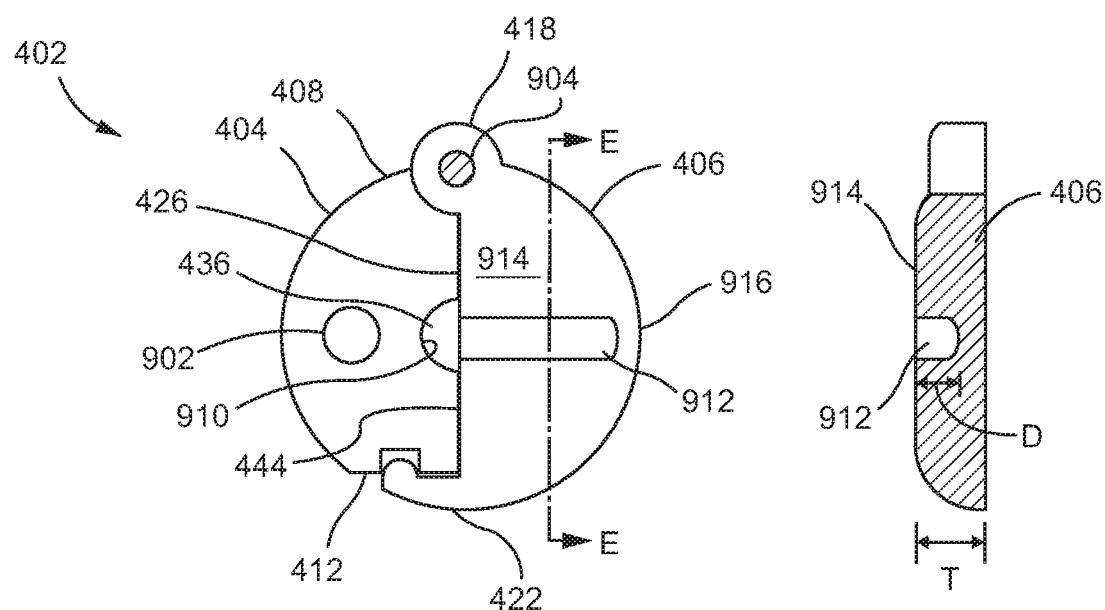

Referring to FIG. 9D, the lead fixation accessory 402 may include a channel or groove 912 sized to receive and hold in place, a portion of the lead body. The channel 912 is located relative to an upper surface 914 of the lead fixation accessory 402 and may, for example, be formed in the second arm 406 so that it extends from the inner edge 444 of the second arm to a point at or near an outer edge 916 of the second arm. Alternatively, a channel may be formed in the first arm 404. Furthermore, the lead fixation accessory may include a plurality of channels formed in one or both of the arms 404, 406.

The channel 912 provides several beneficial features, including a means to secure the lead in place as the lead body transitions over the surface of the lead fixation accessory 402 from the opening 436 to the outer edge 916. The channel 912 also reduces the combined profile of the lead fixation accessory and lead body at the placement site. More specifically, without the channel 912 the lead body would rest on the upper surface 914 of the lead fixation accessory. Thus, the combined profile of the accessory and lead body would be equal to the thickness T of the second arm 406 and the diameter (or thickness or height) of the lead body. For a lead fixation accessory 402 with a channel 912, all or a part of the diameter of the lead body would rest within the channel and the combined profile would be reduced by the depth D of the channel. This lower combined profile of the lead fixation accessory 402 and lead body provides a placement site that is less noticeable to the patient and others, and is thus more comfortable and aesthetically pleasing.

Figure 9E:
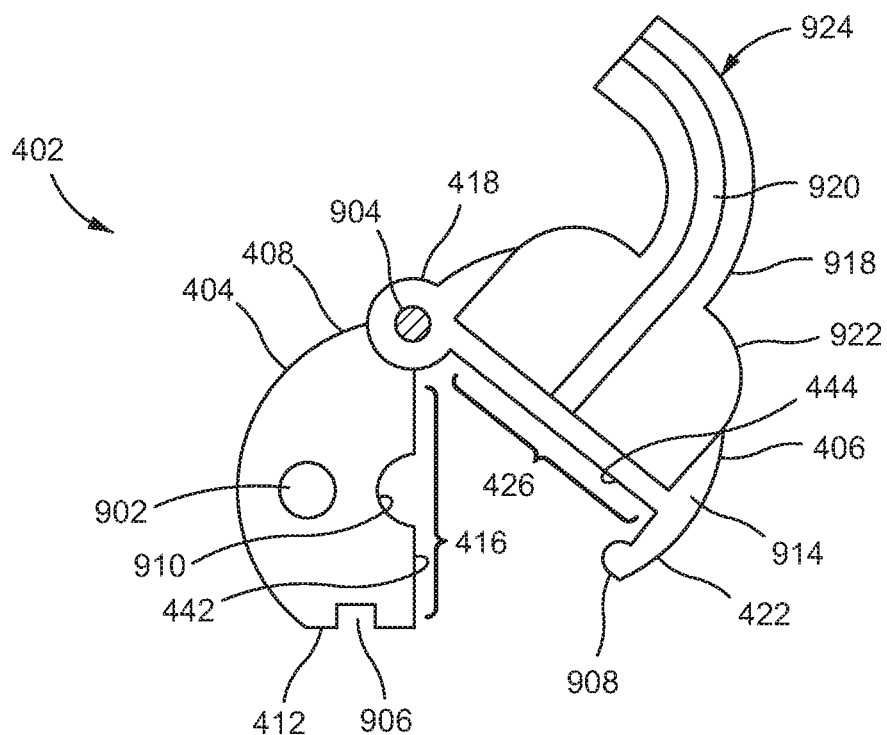
Figure 10A:
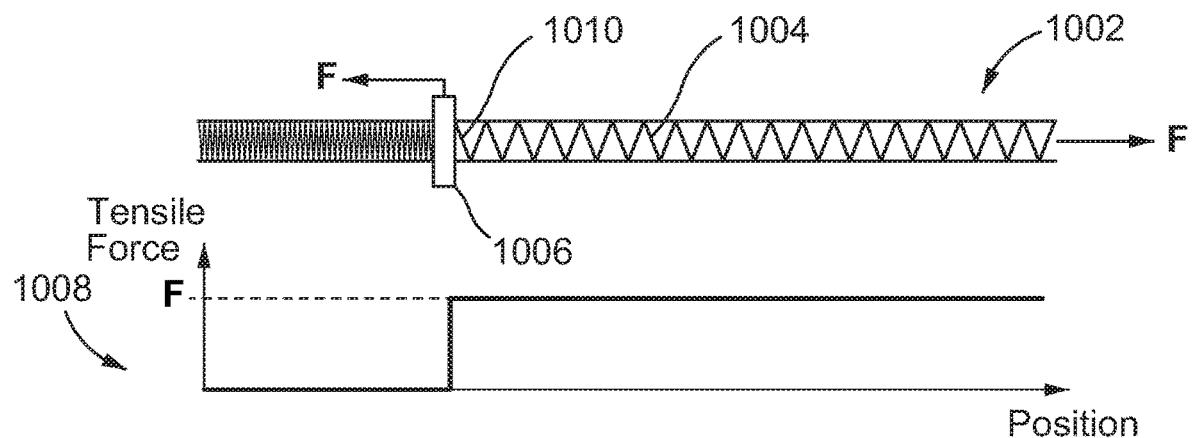
FIG. 10A is a schematic illustration of tensile force on a lead in a situation where the lead is firmly affixed at a given point—without a strain relief member.
Figure 10B:
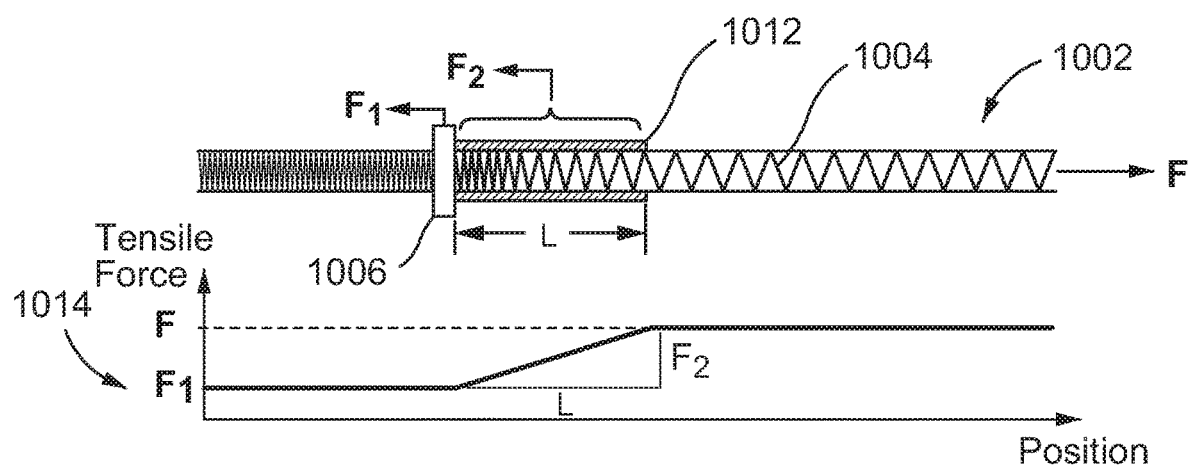
FIG. 10B is a schematic illustration of tensile force on a lead in a situation where the lead is firmly affixed at a given point—with a strain relief member.

With reference to FIG. 9E, the lead fixation accessory 402 may include strain relief member 918 having a lead recess channel 920 sized to receive and hold in place, a portion of the lead body, and to relieve stress in the lead body. The rationale for providing strain relief to a lead is illustrated in FIGS. 10A and 10B, which shows idealized scenarios for understanding the impact of strain relief. The situation where a lead is firmly affixed at a given point and without a strain relief member, is shown in FIG. 10A. When a tensile force F is applied to a lead 1002, the helical coil structure 1004 within the lead body expands uniformly except at the point of retention 1006. At the point of retention 1006, where the lead 1002 is constrained, the force diagram 1008 shows an abrupt increase in tensile force. As a result, there will be an asymmetric distortion in the ability of the helical coil structure 1004 within the lead body to flex at the last free coil 1010 that will produce a significant stress concentration factor at the point of retention 1006.

The situation where a lead is firmly affixed at a given point and with a strain relief member, is shown in FIG. 10B. When a tensile force F is applied to a lead 1002, the helical coil structure 1004 within the lead body expands uniformly up until the strain relief member 1012. Along the length of L of the strain relief member 1012, the force diagram 1014 shows a gradual change in tensile force the results in a reduced tensile force at the fixation point 1006—relative to that shown on FIG. 10A. This reduction in tensile force will lower the stress concentration factor at the fixation point 1006 and reduce the probability of lead fracture Returning to FIG. 9E, the stain relief member 918 may be formed of a flexible silicone rubber and may be associated with either of the arms 404, 406. In FIG. 9E, the strain relief member 918 is associated with the second arm 406 and may be attached, for example, by adhesion, to the upper surface 914 of the second arm. In another configuration, a strain relief member may be integrated with, e.g., formed together with and as part of, the second arm. An example of this configuration is shown in FIGS. 9F and 9G, which are described further below.

The stain relief member 918 includes a base portion 922 and an arcuate portion 924 that extends from the base portion. The arcuate portion 924 of the strain relief member 918 provides improved strain relief over strain relief members that are entirely straight. This is so because a force applied to a lead at a point proximal where the lead exits the arcuate portion 924, in any vector direction relative to the arcuate portion, will induce some bending in the arcuate portion of the strain relief member. The bending of the arcuate portion 924 reduces the force at the base portion 922 of the strain relief member 918 and thus the stress concentration at the point where the lead enters the strain relief member from the skull hole. For a strain relief member that is entirely straight strain, a force applied to a lead at a point proximal where the lead exits, in a vector direction along the length of the strain relief member, would be less effective in reducing the stress concentration at the point where the lead enters the strain relief member from the skull hole.

Figure 9F:
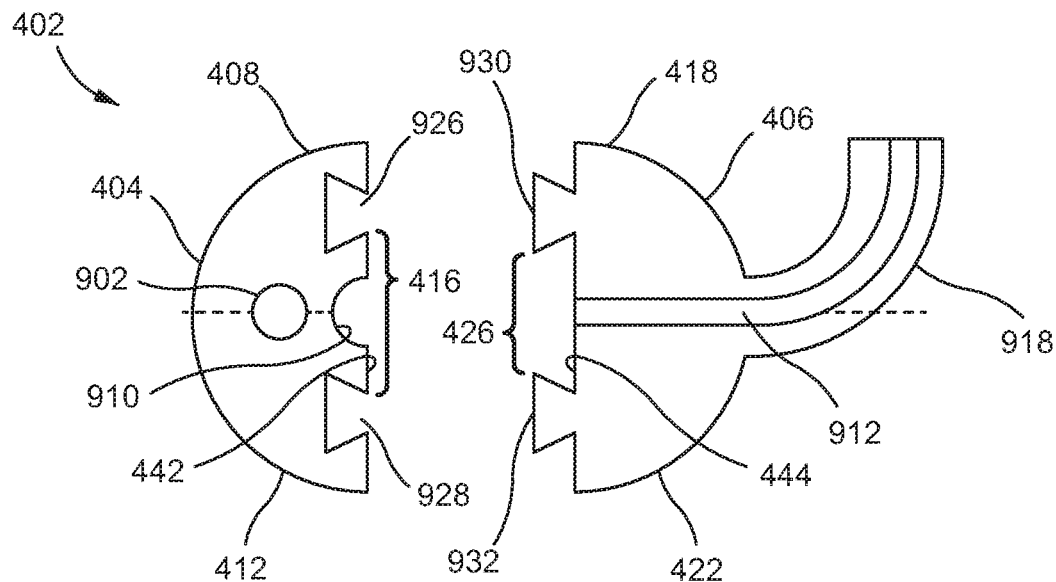
FIG. 9F is a top view of a lead fixation accessory according to embodiments in an open position.
Figure 9G:
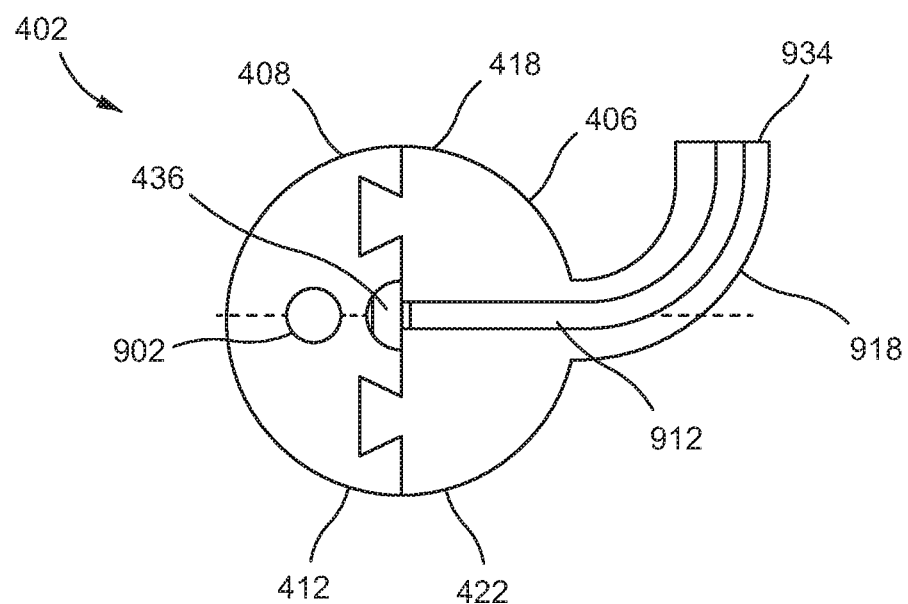
FIG. 9G is a top view of the lead fixation accessory of FIG. 9F in a closed position.

With reference to FIGS. 9F and 9G, in another embodiment, a lead fixation accessory 402 for securing a lead to a skull includes a first arm 404 and a second arm 406. Each of the first arm 404 and second arm 406 may be formed of a biocompatible polymer, e.g. 30A-80A silicone, or biocompatible plastic, e.g., polyurethane or polyetheretherketone (PEEK). The first arm 404 has a first end 408 with an engagement feature 926, a second end 412 with an engagement feature 928, and a middle region 416 that extends between the first end and the second end. The middle region 416 includes one or more apertures 902 sized to receive an attachment mechanism, e.g., bone screw, that is configured to penetrate the surface of the skull to secure the first arm to the skull. The second arm 406 also has a first end 418 with an attachment feature 930, a second end 422 with an engagement feature 932, and a middle region 426 that extends between the first end and the second end. The middle region 426 of the second arm may or may not include one or more apertures sized to receive an attachment mechanism to secure the second arm to the skull. The second arm 406 further includes a strain relief member 918 having a curved configuration that provides the same benefits of lead coil strain relief described above with reference to FIG. 9E.

The respective engagement features 926, 928 of the first arm 404 and the engagement features 930, 932 of the second arm 406 combine to form a coupling mechanism by which the first and second arms connect. In the configuration shown in FIGS. 9F and 9G, the engagement features 926, 928 of the first arm 404 are voids and the engagement features 930, 932 of the second arm 406 are tabs configured to mate with the voids to thereby interlock the first and second arms.

When interlocked, the respective middle regions 416, 426 of the arms form an opening 436 sized to secure the lead in place. Like the configurations shown in FIGS. 9A-9E, each of the middle regions 416, 426 includes an inner edge 442, 444, having a contour feature that defines a geometry of the opening 436. For example, the inner edge 442 of the first arm 404 has an arcuate cutout 910, while the inner edge 444 of the second arm is linear and devoid of any cutouts. Configured as such, the inner edges 442, 444 form an opening 436 having a semicircular geometry when the lead fixation accessory 402 is in a closed position. Many other geometries are possible, for example, each of the inner edges 442, 444 may have an arcuate cutout to form an opening having a circular geometry, or a rectangular cutout to form a rectangular opening. Furthermore, an inner edge 442, 444 may have more than one cutout 910 to form more than one opening 436.

The lead fixation accessory 402 includes a channel or groove 912 sized to receive and hold in place, a portion of the lead body. The channel 912 is located relative to an upper surface 914 of the lead fixation accessory 402 and may, for example, be formed in the second arm 406 so that it extends from the inner edge 444 of the second arm to a point at or near the end 934 of the strain relief member 918. As previously described, the channel 912 provides several beneficial features, including a means to secure the lead in place as the lead body transitions over the surface of the lead fixation accessory 402. The channel 912 also reduces the combined profile of the lead fixation accessory and lead body at the placement site.

Lead Stabilization Tools

FIGS. 5A-5H illustrate an embodiment of a lead stabilization tool 502 for use when implanting a depth lead through a skull hole. The lead stabilization tool 502 is configured to allow the user to grasp the lead body at or about the level of the skull hole once the distal end of the lead has been delivered to the target, to discourage dislodging the lead distal end from the target while any remaining steps of the procedure are attended to that require handling the portion of the lead extending proximally of the skull hole. A curved portion or hook of the tool is dimensioned to be small enough so that it can be manipulated in the space between the inner lumen of a slotted cannula and the lead body occupying the cannula to partially encircle the lead body, and then the tool applies tension to the hook so that it holds the lead stable relative to the tool. The surgeon can then extract the lead from the cannula and/or secure the lead with a lead fixation accessory at the level of the skull, with less concern that these actions will pull the distal end of the lead away from the target. Once the surgeon deems the risk that the lead will become dislodged from the target to be low, he or she can release the lead body from the tool.

To accomplish its intended functions, the lead stabilization tool 502 is configured to transition between three states: 1) a deactivated or resting state, 2) an extended state in which a curved, lead-gripping member is extended, and 3) a partially retracted state in which the curved, lead-gripping member (partially encircling the lead body) is partially retracted into the tool housing to apply tension to the lead to hold the lead in place. An embodiment of the lead stabilization tool is shown in the deactivated or resting state in FIGS. 5A-5D, in the extended state in FIGS. 5E and 5F, and in the partially retracted state relative to a lead body in FIGS. 5G and 5H.

As described further below in a description of an implant procedure, the tool is oriented relatively perpendicularly to a longitudinally-extended slot in the cannula and the lead disposed therein. The tool is actuated to the extended state to advance a member with a hook portion to a position between the lead body and the cannula inner wall to engage the lead body. The surgeon can adjust the angle of the tool relative to the lead until confident that the hook is partially encircling the lead body. When satisfied with the orientation of the hook relative to the lead body, the surgeon can operate the tool to partially retract the member with the hook, thus maintaining some tension between the hook and the lead to stabilize the two elements relative to each other. The surgeon can maintain the tension by keeping the tool in the partially retracted state until other steps requiring manipulation of the lead portion extending proximally of the skull hole have been completed (e.g., separating the lead from the cannula, withdrawing the stylet from the lead, securing the lead in or near the skull hole with a lead fixation accessory, etc.) When those steps are completed, the surgeon can re-extend the hook to disengage it from the lead body. The embodiment of the lead stabilization tool 502 shown in FIGS. 5A-5H is sized and configured for single-handed- and single-finger-operation. In one configuration, the lead stabilization tool 502 is about the size of an automobile key fob, e.g., approximately 50 mm long and 40 mm at its widest point, and can be operated using a single button.

The lead stabilization tool 502 includes a housing 504 having a proximal end 506 and a distal end 508. The housing may be formed of a material such as polycarbonate, a thermoplastic polymer such as ABS (acrylonitrile butadiene styrene) or an ABS blend, polyester, aluminum, or stainless steel. The housing 504 narrows to a nose 510 at the distal end 508. The embodiment shown in FIGS. 5A-5H is intended to be maneuverable within the cannula relative to the lead so that a hook 534 can partially encircle the lead body. Thus, the nose 510 is dimensioned so that it is not too large in any orientation relative to the slot in the cannula to clear the edges of the slot. For example, in a particular design of the lead stabilization tool 502 for use with a slotted cannula having a slot with a width of 1.57 mm, the width 512 of the nose 510 is less than 1.57 mm. More particularly, the nose width 512 is about 1 mm less than the cannula slot width. The nose 510 may be further configured to have a contoured or curved surface 518 having a radius of curvature that generally corresponds to a radius of curvature of a cylindrical lead to be implanted using the cannula. As shown and described further below, this curved surface 518 provides for greater surface area contact between a cylindrical lead and the nose 510 during particular stages of operation of tool, including, for example, when a hook portion of the tool is partially retracted and pulls the lead against the nose.

Referring now to FIGS. 5D, 5E, 5G, and 5H, the housing 504 also includes a lumen 520 that extends through a portion of the housing 504 along a longitudinal axis 522. The lumen 520 terminates at an opening 524 at the distal end 508 of the housing 504. The lead stabilization tool 502 further includes an extension member 526 that is at least partially located in the lumen 520. The extension member 526 is configured to be displaced along the longitudinal axis 522 of the housing 504. The extension member 526 has a proximal portion or base 528 and a distal portion or grip structure 530. The grip structure 530 terminates in a tip or hook 534 that is provided with a radius of curvature that approximates that of the brain lead types with which the tool is intended to be used. While the extension member 526 moves along the longitudinal axis 522 when the tool is actuated between the extended and partially withdrawn states (i.e., by pressing and releasing a push button 540), the hook is always disposed outside of the housing 504.

The grip structure 530 may be formed of a metal and formed to include the hook 534 having a radius of curvature 532. The grip structure 530 may be sized to fit between the inner wall of the cannula and the lead so that the user can manipulate the hook 534 between the cannula inner wall and the lead body. For example, in a design of a lead stabilization tool 502 for use with a cannula having an inner diameter of 1.72 mm, and a lead having a diameter of 1.27 mm, the grip structure 530 may be formed as cylinder having a diameter 536 (FIG. 5C) of approximately 0.381 mm. As such, the hook 534 is able to fit easily in the space between the inner wall of the cannula and the outer surface of the lead. It will be appreciated that a hook 534 with a diameter greater than the difference in the diameters between the inner diameter of the cannula and the outer diameter of the lead could be used, for example, to lend strength or stiffness to the hook, since the tool can be used to push the lead around by the hook within the cannula. However, since an objective is to avoid manipulating the lead so much as to dislodge the lead distal end from the target, the preferred design will be it easy for the hook to be maneuvered into position and then maintained there, to reliably grasp the lead body.

The lead stabilization tool 502 is toggled between the deactivated or resting state, the extended state, and the partially retracted state with an operating mechanism that is coupled to the housing 504 and to the extension member 526. The operating mechanism includes a push button 540 and a biasing mechanism. Once the tool is positioned so that the nose 510 is at or in the slot of the cannula, the user pushes the push button 540, which is configured for slideable engagement with the base 528 of the extension member 526. More specifically, when the tool 502 is deactivated, the extension member 526 is fully retracted in the housing 504, except for the hook 534, which remains outside the housing. As shown in FIG. 5D, the base 528 of the extension member 526 is provided with an angled edge 546. The push button 540 has a downward protection 542 that terminates in an angled edge 544 that complements the angle of the angled edge 546 of the extension member. In the deactivated state, the angled edge 544 of the push button 540 rests on and matches up with the angled edge 546 of the extension member 526. In this design, movement of the push button 540 is constrained along the vertical axis 548 (FIG. 5D), i.e., up and down, using tabs 545 on the button that contain it in a well 551 defined proximally by a well projection 541 and distally by wall 543 of the housing 504.

As shown in FIG. 5F, when the push button 540 is pushed, the downward force applied causes the angled edge 544 of the push button 540 to slide down the angled edge 546 of the extension member 526, urging the extension member along the longitudinal axis 522 towards the nose 510. As shown in FIGS. 5E and 5F, when the push button 540 is fully engaged (i.e., pressed as far as it can be pressed), the extension member 526 extends as far as the design permits outside of the housing proximal end 506. In some variations, the user can apply varying pressure to the button to vary the degree to which the extension member extends outside of the housing.

Transition of the lead stabilization tool 502 between the deactivated state (FIGS. 5A-5D) and the extended state (FIGS. 5E and 5F) is aided by a biasing mechanism coupled to the push button 540 and the extension member 526. In the variation shown in FIGS. 5A-5H, the biasing mechanism includes a pair of springs, one disposed at the push button 540 and the other disposed around the grip structure 530 of the extension member 526. More particularly, as shown in FIGS. 5D and 5E, one of the springs 560 is aligned with the push button 540 along the vertical axis 548, which is generally perpendicular to the longitudinal axis 522 along which the lumen in the housing extends, and the other of the springs 562 surrounds and is axially aligned with the grip structure 530 of the extension member 526 along the longitudinal axis 522.

The biasing mechanism 560, 562 has an associated biasing force that corresponds to an amount of force applied by the biasing mechanisms 560, 562 against particular structures of the lead stabilization tool 502. The first biasing mechanism 560 applies a biasing force against the push button 540, which force is sufficient to maintain the push button in the deactivated state (FIG. 5D) when the button is not being pressed. Likewise, the second biasing mechanism 562 applies a biasing force against the base 528 of the extension member 526, which force is sufficient to maintain the extension member in the deactivated state (FIG. 5D) when the push button 540 is not being pressed. However, when the push button 540 is pressed, applying a force greater than the biasing forces of the spring 560 at the button and the spring 562 at the grip structure 530, the lead stabilization tool transitions to an extended state (FIG. 5E, 5F) during which the extension member 526 is displaced within the lumen 520 along the longitudinal axis 522 and a portion of the grip structure 530 extends out beyond the nose 510 of the tool housing 504.

FIGS. 5G and 5H are a top view and a side view of the lead stabilization tool 502 in the third of its possible states, namely, the partially retracted state. Here, the hook 534 has engaged the lead body, and the user has released the push button 540, and the biasing mechanism has caused the extension member 526 to partially retract into the housing 504. The force pulls the encircled lead up against the curved surface 518 of the nose 510 and maintains the lead there, unless and until the tool is actuated again to the extended state so the lead body can be disengaged from the hook 534.

FIGS. 5I-5M illustrate another embodiment of a lead stabilization tool 550 for use when implanting a depth lead through a skull hole. In this embodiment, the operating mechanism configured to transition the lead stabilization tool 550 between an extended state and an at least partially retracted state for holding a lead includes a thumb wheel 554. The thumb wheel 554 is oriented in a plan approximately perpendicular to the plane of the extension member 552, and is configured to engage a feature of the extension member 552 when the wheel is rotated, as by an operator's thumb or finger, to thereby move the extension member 552 along the longitudinal axis 522 of the lead stabilization tool 550.

In one configuration (shown in FIGS. 5J and 5K), the thumb wheel 554 is characterized by a threaded portion (not visible) on an inner diameter of a thumb wheel cylinder 556 having threads which are configured to mate with a threaded portion 558 on an outer diameter of a base portion 559 of the extension member 552. When the thumb wheel 554 is rotated in the direction of the arrow 547, the threaded engagement between the thumb wheel cylinder 556 and the base portion 559 of the extension member 552 cause the hook 534 to extend distally. In this extended state, the hook 534 may be maneuvered through the slot 306 in the cannula 304 and between an inner wall of the cannula and the lead 320, to partially encircle a lead body, in the same manner as described above with reference to the lead stabilization tool of FIGS. 5A-5H. When the thumb wheel 554 is rotated in the direction of the arrow 549 the threaded engagement between the thumb wheel cylinder 556 and the base portion 559 of the extension member 552 cause the hook 534 to withdraw distally. In this partially retracted state, the hook 534 may pull the lead body captured by the hook against the curved surface 518 of the housing nose 510, in the same manner as described above with reference to the lead stabilization tool of FIGS. 5A-5H.

In another configuration, (shown in FIGS. 5L and 5M), the thumb wheel 554 is characterized by a shaft 570 having a cam-coupling 572 at its distal end that is configured to couple with a cam-coupling 574 of the extension member 552. The cam-coupling 574 is formed as part of a base portion 576 of the extension member 552. The shaft 570 and cam-coupling 572 are fixed to the thumb wheel 554 so that rotation of the thumb wheel results is corresponding rotation of the cam-coupling. The thumb wheel 554 is coupled to the lead stabilization tool 550 housing in a way that allows rotation of the thumb wheel about the longitudinal axis 522 of the tool while preventing movement of the wheel along the longitudinal axis. A wire like portion 578 of the extension member 552 extends from the base portion 576 through a lumen of the shaft 570. The base portion 576 includes anti-rotation features 580 that mate with corresponding features (not shown) of the lead stabilization tool 550 housing in a way that prevents rotation of the base portion 576 and cam-coupling 574 about the longitudinal axis 522 of the tool while allowing movement of it along the longitudinal axis.

When the thumb wheel 554 is rotated in the direction opposite of the arrow 582, the coupling between the cam-coupling 572 of the thumb wheel and the cam-coupling 574 of the extension member 552 assume the closed arrangement shown in FIG. 5L. This causes the base portion 576, together with the rest of the extension member 552, to move in the distal direction 586 to cause the hook 534 to extend distally. In this extended state, the hook 534 may be maneuvered through the slot 306 in the cannula 304 and between an inner wall of the cannula and the lead 320, to partially encircle a lead body, in the same manner as described above with reference to the lead stabilization tool of FIGS. 5A-5H. When the thumb wheel 554 is rotated in the direction of the arrow 582, the coupling between the cam-coupling 572 of the thumb wheel and the cam-coupling 574 of the extension member 552 assume the open arrangement shown in FIG. M. This causes the base portion 576, together with the rest of the extension member 552, to move in the proximal direction 584 to cause the hook 534 to withdraw distally. In this partially retracted state, the hook 534 may pull the lead body captured by the hook against the curved surface 518 of the housing nose 510, in the same manner as described above with reference to the lead stabilization tool of FIGS. 5A-5H.

FIG. 5N illustrates another embodiment of a lead stabilization tool 590 for use when implanting a depth lead through a skull hole. In this embodiment, the operating mechanism configured to transition the lead stabilization tool 590 between an extended state and an at least partially retracted state for holding a lead includes a slide button 592. The slide button 592 is oriented for movement back 594 and forth 596 along the longitudinal axis 522 of the lead stabilization tool 590, and is coupled to a base portion 598 of the extension member 552. When the slide button 592 is operated, as by an operator's thumb or finger, the extension member 552 moves along the longitudinal axis 522 of the lead stabilization tool 590.

When the slide button 592 is moved in the direction of the arrow 596, the coupling between the slide button and the extension member 552 causes the extension member 552, to move in the distal direction 586 to cause the hook 534 to extend distally. In this extended state, the hook 534 may be maneuvered through the slot 306 in the cannula 304 and between an inner wall of the cannula and the lead 320, to partially encircle a lead body, in the same manner as described above with reference to the lead stabilization tool of FIGS. 5A-5H. When the slide button 592 is moved in the direction of the arrow 594, the coupling between the slide button and the extension member 552 causes the extension member to move in the proximal direction 584 to cause the hook 534 to extend withdraw proximally. In this partially retracted state, the hook 534 may pull the lead body captured by the hook against the curved surface 518 of the housing nose 510, in the same manner as described above with reference to the lead stabilization tool of FIGS. 5A-5H.

FIG. 5O illustrates another embodiment of a lead stabilization tool 591 for use when implanting a depth lead through a skull hole. In this embodiment, the grip structure is in the form of a slotted tube 581 that extends from the distal end of the housing of the lead stabilization tool 591. The slotted tube 581 includes a pair of pinchers 583 at or near the distal end 585 of the tube that are separated by a separation distance 587. The extension member comprises a mandrel 595 configured to slide back and forth within the slotted tube 581. The operating mechanism configured to transition the lead stabilization tool 591 between an extended state and an at least partially retracted state for holding a lead includes a slide button 593 coupled to the mandrel 595. The slide button 593 is oriented for movement back 594 and forth 596 along the longitudinal axis 522 of the lead stabilization tool 591. When the slide button 593 is operated, as by an operator's thumb or finger, the mandrel 595 moves along the longitudinal axis 522 of the lead stabilization tool 590.

When the slide button 593 is in a neutral position, the mandrel 595 positioned away from the distal end 585 of the slotted tube 581 and the separation distance 587 between the pinchers 583 allows for the pinchers to be maneuvered through the slot 306 in the cannula 304.

When the slide button 593 is moved in the direction of the arrow 596, the coupling between the slide button and the mandrel 595 causes the mandrel to move in the distal direction 586 through the slotted tube 581. The inner diameter of the slotted tube 581 reduces in size along the length of the tube from a proximal-end diameter to a distal-end diameter that is smaller than the proximal-end diameter. The outer diameter of the mandrel 595 is sized so that the mandrel slides relatively freely, with little interference from the slotted tube 581, as it moves through the proximal end of the tube. As the mandrel 595 slides through the distal region of the slotted tube 581, there is increased interference with the slotted tube. As a result, the mandrel 595 applies radially outward force to the inside of the slotted tube 581 that causes the slot 589 to expand and the separation distance 587 between the pinchers 583 to increase to a size so that allows the lead body to be positioned between the pinchers.

After the lead body is positioned between the pinchers 583, the slide button 593 is moved in the direction of arrow 594 to move the mandrel 595 away from the distal end 585 of the slotted tube 581. Doing so causes the slot 589 to narrow and the separation distance between the pinchers 583 to decrease to a size so that lead body is held in place between the pinchers.

FIGS. 5P-5S illustrates alternate structures for gripping a lead that may be used in placed of the hook shown in FIGS. 5A-5N. These alternate structures 561, referred to as "pincher" structures, include a pair of arms 563, 565 coupled together at respective first ends and spaced apart at respective second ends by a distance D less than the width of the slot 306 of a cannula 304. The pincher structure 561 is attached to the distal end of an extension member 552 and may be moved in the distal direction and proximal direction using any of the operating mechanisms described above with reference to FIGS. 5A-5N.

The distal portion of the pincher structure 561, including the coupled end of the arms 563, 565, is configured to be moved to different positions relative to a feature of the nose 510 of the lead stabilization tool so that the separation distance D between the arms may be changed. The nose feature may be in the form of a cutout at the distal end of the nose 510. In a first position of the pincher structure 561 (shown in FIGS. 5P and 5R), which corresponds to an extended state of the tool, the separation distance D between the arms 563, 565 allows for the arms to be maneuvered to be on either side of a lead 320. In a second position of the pincher structure 561 (shown in FIGS. 5Q and 5S), which corresponds to a partially retracted state of the tool, the pincher structure 561 is moved in the distal direction 586 such that a portion of the structure is pulled within the nose 510. This causes the arms 563, 565 to mechanically engage with the cutout feature of the nose 510 and bend toward each other, which in turn, causes the separation distance D between the arms to decrease to a size so that the lead 320 is held or compressed in place between the arms.

FIGS. 5T and 5U illustrate an alternate configuration of a pincher structure that may be used in conjunction with a pull wire. This alternate structure includes a pair of arms 567, 569 extending from the nose 510 of the lead stabilization tool. One of the arms 567 is coupled to a pull wire 571 which may be configured to be moved in the distal direction and proximal direction using any of the operating mechanisms described above with reference to FIGS. 5A-5N. The arm 567 is configured to bend upon application of a pulling force through the pull wire 571.

As shown in FIG. 5T, when the pull wire 571 is in a resting state or un-pulled state, the arm 567 coupled to the pull arm assumes an unbent configuration and the respective arms 567, 569 are spaced apart at respective ends by a distance D that allows for the arms to be maneuvered to be on either side of a lead 320. As shown in FIG. 5S, when the pull wire 571 is in a pulled state, the arm 567 coupled to the pull arm assumes a bent configuration and the respective arms 567, 569 held or compressed the lead 320 in place.

FIGS. 5V-5X illustrate another embodiment of a lead stabilization tool 501 for use when implanting a depth lead through a skull hole. In this embodiment, the grip structure 530 may be a distal region of the extension member 526 that is configured to transition between a linear shape and a curved shape. For example, the grip structure 530 may be formed by cutting a number of spaced apart, partial-circumference slots 503 into a tubular distal region 505 of the extension member.

The operating mechanism configured to transition the lead stabilization tool 501 between an extended state and an at least partially retracted state for holding a lead includes two activation mechanisms, one for controlling the extension and retraction of the extension member 526 relative to the nose 510 of the tool, and the other for controlling the shape of the grip structure 530. In the example configuration of FIGS. 5V-5X, a thumb wheel 554 may be coupled to the extension member 526 to control extension and retraction of the extension member, as described above with reference to FIG. 5I-5K. Alternatively, the extension member 526 may be controlled by a push button (as shown in FIG. 5A-5H) or a slide button (as shown in FIGS. 5N and 5O) instead of a thumb wheel.

Continuing with the example of FIGS. 5V-5X, a slide button 507 controls the state of the grip structure 530. To this end, the operating mechanism further includes a core wire 509 coupled to the slide button 507 that extends through a lumen of the extension member 526. Alternatively, the core wire 509 may be coupled to a push button (as shown in FIG. 5A-5H) or a thumb wheel (as shown in FIG. 5I-5K) instead of a slide button. The core wire 509 is mechanically coupled at its proximal end 511 to the slide button 507, and at its distal end 513 to the distal end of the grip structure 530, and s configured to slide within the lumen in the extension member 526.

In this embodiment of the lead stabilization tool 501, there are two stages of an extended state. In the first stage, the thumb wheel 554 is activated to extend the extension member 526 through the nose 510 of the lead stabilization tool 501, as shown in FIG. 5W. Next, the slide button 507 is moved in the distal direction 586 to move the core wire 509 in the distal direction. Movement of the core wire 509 in the distal direction 586 results in the application of a bending force F at the distal end of the slotted grip structure 530, which causes the grip structure to bend and assume the curved shape 515 shown in FIG. 5W. The grip structure 530 may then be maneuvered to at least partially encircle a lead.

Next, the thumb wheel 554 is operated to move the extension member 526 in the proximal direction 584 to thereby retract part of the extension member into the nose 510 and place the lead stabilization tool 501 in a partially retracted state. Retraction of the extension member 526 pulls the encircled lead up against the curved surface 518 of the nose 510 and maintains the lead there, unless and until the grip structure 530 assumes its linear shape 517 through movement of the slide button 507 in the proximal direction 584, or until the tool is placed in the extended state (as shown in FIG. 5W) through operation of the thumb wheel 554 that moves the extension member 526 in the proximal direction so the lead is no longer compressed between the nose 510 and the grip structure 530.

Depth Lead implant Procedures

Figure 8:
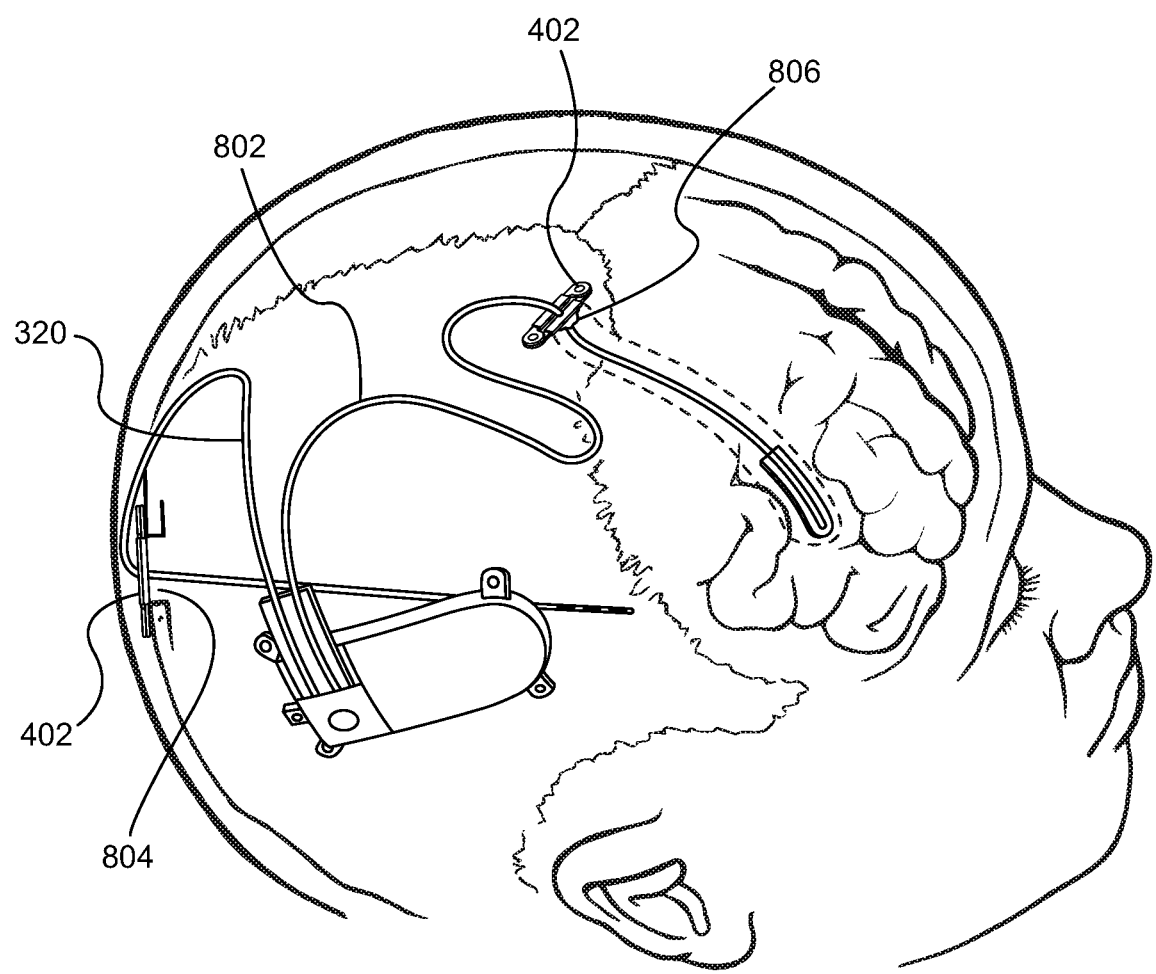
FIG. 8 is a schematic view of a patient's cranium showing an implanted depth lead and an implanted cortical lead, each of which is secured at a respective skull hole by two different lead fixation accessories according to the embodiments of FIGS. 4A-4F.

FIG. 6 is a flowchart of a method of implanting a depth lead through a skull hole using both the lead stabilization tool of FIGS. 5A-5H and the lead fixation accessory of FIGS. 4A-4I. FIGS. 7A-7R are corresponding top-view/side-view schematics of various stages of the method of FIG. 6. For example, FIG. 7A and FIG. 7B represent a top view (FIG. 7A) and a side view (FIG. 7B) of a particular stage of the implant procedure, while FIG. 7C and FIG. 7D represent a top view (FIG. 7C) and a side view (FIG. 7D) of another stage of the implant procedure. For clarity of illustration, some items shown in a particular top view may not be shown in the corresponding side view. For example, the lead fixation accessory 402 shown in the top view of FIG. 7C is not shown in the corresponding side view of FIG. 7D. FIG. 8 is a schematic illustration of a patient's cranium showing an implanted depth lead 320 and an implanted cortical lead 802, each of which is secured at a respective skull hole 804, 806 by two different lead fixation accessories 402. While the implant procedure to be described involves the use of standard stereotactic equipment (such as shown in FIG. 2), for clarity of illustration only the cannula is shown in any of FIGS. 7A-7R.

In a method according to embodiments, a patient is readied for surgery to implant a depth lead. If a stereotactic frame will be used to guide the lead to a target 712, the frame is attached to the patient, any necessary imaging for co-registration is undertaken, the surgeon identifies and marks the location of a skull hole through which the lead will be implanted, swings any stereotactic equipment obstructing access to the patient out of the way, and incises the scalp and then forms the skull hole 710 using an air-powered drill for a standard burr hole (such as with a 14 mm diameter) or a twist drill (such as with a 3.2 mm diameter). (FIG. 6 at block 602 and. FIGS. 7A-7B)

While there is no stereotactic equipment in the way, and/or before any instruments or devices are introduced into the skull hole 710, the surgeon may elect to attach off to one side of the skull hole one end of a lead fixation accessory 402 such as by orienting a first arm 404 on top of a second arm 406 of the accessory so that the respective first apertures 410, 420 align to form a first attachment hole 432, and then inserting a bone screw or pin 702 into the hole to secure to the skull surface 706. (FIG. 6 at block 604, FIGS. 4A-4F, and FIGS. 7A-7B). In configurations of the lead fixation accessory 402 where the first arm 404 and the second arm 406 are coupled together by a hinge mechanism 411, 413, the end of the accessory having the hinge mechanism is secured to the skull surface 706 by inserting a bone screw into the hole 419a/419b, 427a/427b extending through the hinge mechanism. (FIG. 6 at block 604, FIGS. 4H-4I, and FIGS. 7A-7B).

After the lead is implanted, all that will be left to do to secure the lead in the lead fixation accessory 402 will be to close the two arms 404, 406 around the lead extending proximally of the skull hole 710, line up the two arms so that the respective second apertures 414, 424 form a second attachment hole 434, insert another bone screw or pin into the hole, and tighten down both attachment mechanisms until the lead fixation assembly is secure against the lead body and the skull surface. Alternatively, the surgeon can wait until after the lead has been delivered to the target to use the lead fixation accessory, since no part of the lead fixation accessory must be secured in or near the skull hole before the lead is introduced into the skull hole 710.

Before the depth lead is introduced to the patient, it can be measured to mark a point on a proximal portion of the lead that corresponds to the distance from the skull to the target plus the distance from the skull to the top of the cannula, so that when the lead has been advanced through the cannula far enough for the marked point to reach the top of the cannula, the surgeon will know the lead has been implanted far enough. A stop gauge 310 may be placed around the diameter of the depth lead on a proximal portion of the depth lead at a point calculated to provide feedback to the surgeon that the distal lead end has reached the target when the point coincides with the proximal end of the cannula during implantation of the lead (i.e., a cue as to when to stop advancing the lead) (FIG. 6 at block 606).

Next, the stereotactic equipment is readied for use with the lead. If a frame is being used, a slotted cannula 304 is inserted into a guide tube (see the guide tube 204 in FIG. 2) at a trajectory relative to the skull hole 710 that is designed to reach the target 712. The cannula 304 may have an inner rod (not shown) slidably disposed therein to discourage tissue from backing up into the interior of the cannula as it is used to create a path for the depth lead. The surgeon advances the cannula 304 so that the distal end 308 of the cannula 304 is at or near the target 712 (FIG. 6 at block 608 and FIGS. 7C-7D).

Next, the surgeon introduces the distal end 324 of the depth lead 320 into the cannula lumen at the top of the cannula the proximal end 312 of the cannula 304). The surgeon advances the depth lead 320 through the cannula until the distal end 324 of the depth lead is at the target 712 (FIG. 6 at 610). If a stop gauge 310 has been placed on the proximal portion 328 of the depth lead, then the surgeon will be cued that the distal end 324 has reached the target 712 when the stop gauge reaches the proximal end 312. (FIG. 6, block 610 and FIGS. 7E-7F).

Once the surgeon is satisfied that the distal end 324 of the lead 320 is at the target 712, he or she wants to stabilize the lead near the skull hole 710 while subsequent steps that require manipulation of the portion of the lead 328 extending proximally of the skull hole are attended to. Thus, in FIG. 6 at blocks 612, 614, 616, 618, and 620, and FIGS. 7G-7P), a lead stabilization tool 502 is used to secure the lead while the proximal portion 328 of the lead 320 is still within the cannula 304, since extracting the lead from the cannula is a step that requires manipulation of the proximal portion 328 of the lead 320.

Next, with the tool 502 in the deactivated or resting state, the surgeon brings the nose 510 of the housing with the hook 534 extending slightly therefrom adjacent the cannula slot 736 or inside the slot. (FIG. 6 at block 612 and FIGS. 7G-7H). Then the surgeon presses the push button 540 to extend the hook 534, and maneuvers the extended hook within the space between the cannula 304 inner wall and the lead 320 to partially encircle the lead body with the hook. (FIG. 6 at blocks 616, and FIGS. 7I-7J). When the surgeon is confident that the hook 534 will engage the lead 320, he or she releases the push button 540, which exerts a force that pulls the hook back towards the tool housing 504, and partially withdraws the extended hook until the lead body is secured between the hook and the nose 510 of the housing. (FIG. 6 at block 618, and FIGS. 7K-7L).

Next, the surgeon withdraws the slotted cannula 304 from the skull hole 710. Then, the proximal lead portion 328 is extracted through the cannula slot 736 until it is entirely free of the cannula 304. While the lead 320 and the cannula 304 are being separated, the lead stabilization tool 502 is maintained in the partially retracted state to hold the lead securely against the tool to stabilize it and minimize movement of the distal portion 322 of the lead 320. (FIG. 6 at block 620, and FIGS. 7M-7N).

Next, while the lead stabilization tool 502 is still maintained in the partially retracted state to hold the lead 320 in place, the surgeon undertakes steps to secure the lead to the skull surface 706 by, moving the first arm 404 and the second arm 406 of the lead fixation accessory 402 relative to each other to place the lead fixation accessory 402 in a closed position around the lead 320, with a second end of the lead fixation accessory 402 at a second side 716 of the skull hole 710 opposite the first side 708 of the skull hole. The second end of the lead fixation accessory 402 is then secured to the skull surface 706 by slightly rotating the tool 502 as necessary to gain access to the second attachment hole 434 formed at the second end of the lead fixation accessory, and inserting a screw (not visible) through the hole to thereby maintain the lead fixation accessory 402 in a locked position and secure the portion of the lead 320 adjacent the skull hole 710 in place while the stylet 302 is still in the lead. (FIG. 6 at block 620, and FIGS. 7O-7P).

Next, once the lead fixation accessory 402 is secured around the lead 320 in the closed position, the portion of the lead being gripped by the lead stabilization tool 502 can be released from the lead stabilization tool. To accomplish this, the surgeon presses the push button 540 to extend the hook away from the nose 510, so that the lead body is no longer captured between the hook and the housing and can be freed from the lead stabilization tool 502. (FIG. 6 at block 622, and FIGS. 7Q-7R).

Next, the stylet 302 is removed from the lead 320. (FIG. 6 at block 624, and FIGS. 7Q-7R). As previously described with reference to FIGS. 4A-4F, the lead fixation accessory 402 is configured to secure the lead 320 in place through a compressive force. While the compressive force is sufficient to secure the lead in place, the force is great enough to impede removal of the stylet 302 from the lead 320. Accordingly, if the surgeon prefers, the stylet 302 may be removed prior to releasing the lead 320 from the lead stabilization tool 502. For example, stylet removal may occur along with other steps in block 620.

Upon securing the lead fixation accessory 402 in the closed position, the distal end 324 of the lead 320 is discouraged from moving appreciably relative to the proximal portion 328 of the lead that extends from the lead fixation accessory 402, even when the proximal portion is manipulated, for example, when the surgeon attaches a proximal end to another device internally or externally of the patient or when the patient fiddles or fusses with the proximal portion after implant.

Figure 11:
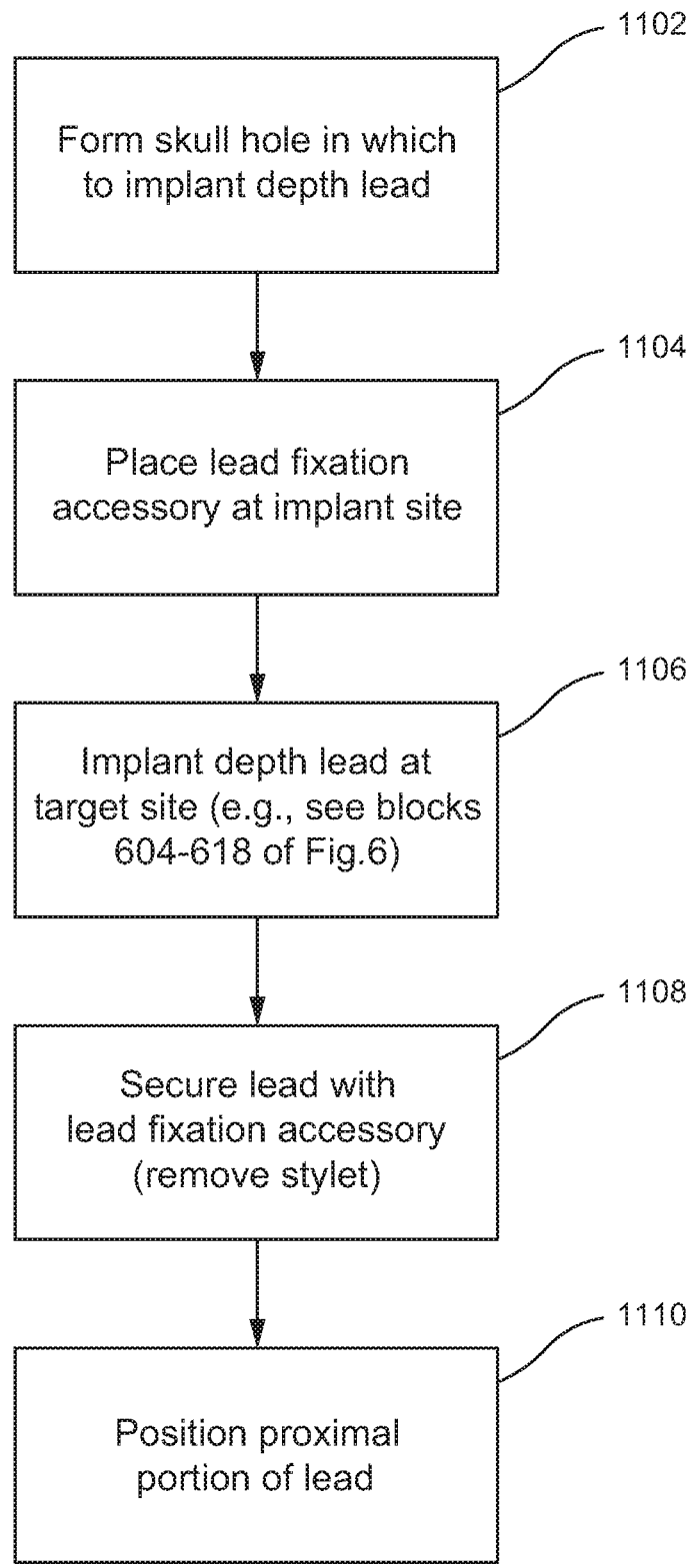
FIG. 11 is a flowchart of a method for implanting a depth lead according to embodiments.

FIG. 11 is a flowchart of a method of implanting a depth lead through a skull hole using a lead fixation accessory of FIGS. 9A-9G. FIGS. 12A-12D are corresponding schematics of various stages of the method of FIG. 11. The method of FIG. 11 may also employ the lead stabilization tool of FIGS. 5A-5H.

Figure 12A:
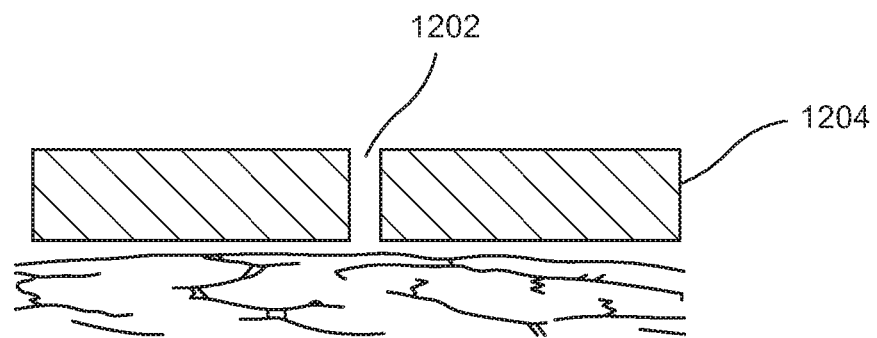
FIG. 12A-12D are top-view and side-view schematics of various stages of the method of FIG. 11.

In a method according to embodiments, a patient is readied for surgery to implant a depth lead. If a stereotactic frame will be used to guide the lead to a target site, the frame is attached to the patient, any necessary imaging for co-registration is undertaken, the surgeon identifies and marks the location of a skull hole 1202 through which the depth lead will be implanted, swings any stereotactic equipment obstructing access to the patient out of the way, and incises the scalp and then forms the skull hole 1202 through the skull 1204 using a twist drill (such as with a 3.2 mm diameter). (FIG. 11 at block 1102 and FIG. 12A).

Figure 12B:
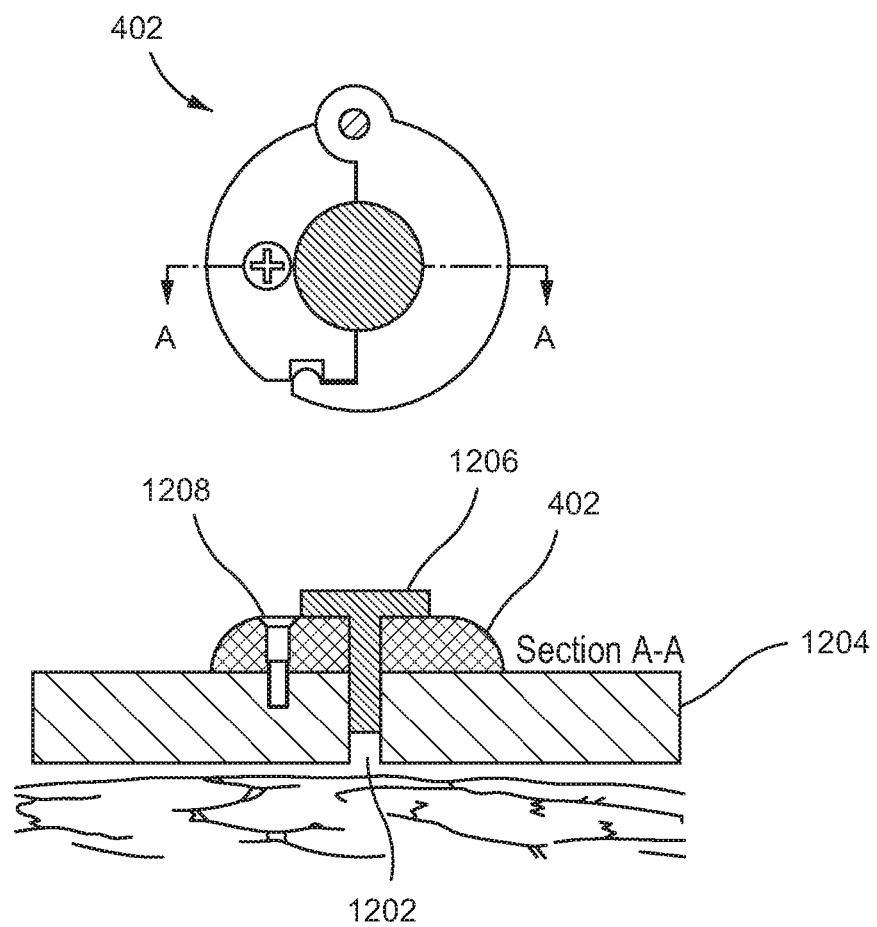

Next, while there is no stereotactic equipment in the way, and/or before any instruments or devices are introduced into the skull hole 1202, the surgeon places a lead fixation accessory 402 at the implant site. To this end, the lead fixation accessory 402 is placed in a closed position, such as shown in FIG. 9B, and positioned over the skull hole 1202. The surgeon visually aligns the opening 436 of the lead fixation accessory 402 with the skull hole 1202 and inserts an alignment pin 1206 through the opening and into the skull hole to establish proper alignment of the opening and skull hole. An attachment mechanism 1208, e.g., bone screw, is secured to the skull 1204 through an aperture 902. (FIG. 11 at block 1104, FIG. 9B, and FIG. 12B).

Next, the alignment pin 1206 is removed from the lead fixation accessory 402. The lead fixation accessory 402 is then placed in an open position, such as shown in FIG. 9A, to allow access to the skull hole 1202 for purposes of implanting a depth lead at the target site. Procedures similar to those described above with respect to blocks 604-618 of FIG. 6 may be performed to implant the lead at the target. (FIG. 11 at block 1106)

Figure 12C:
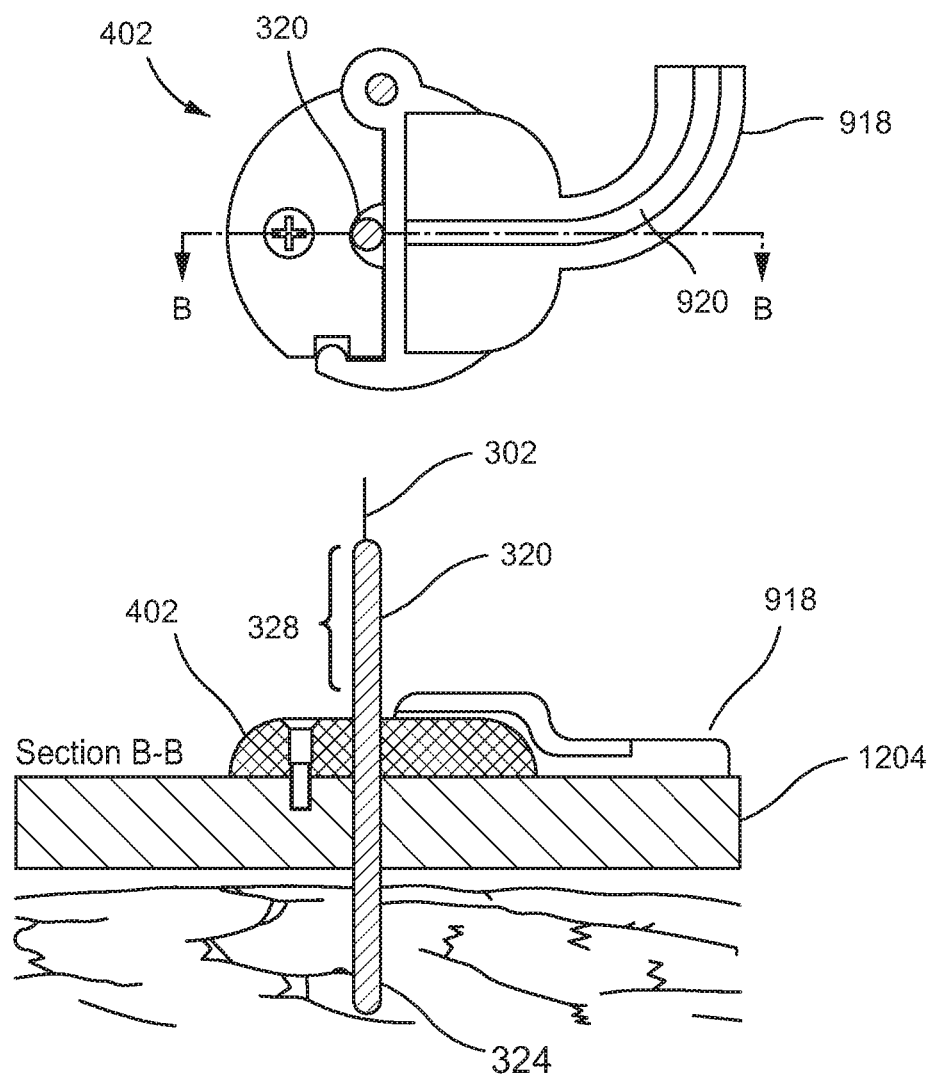
Figure 12D:
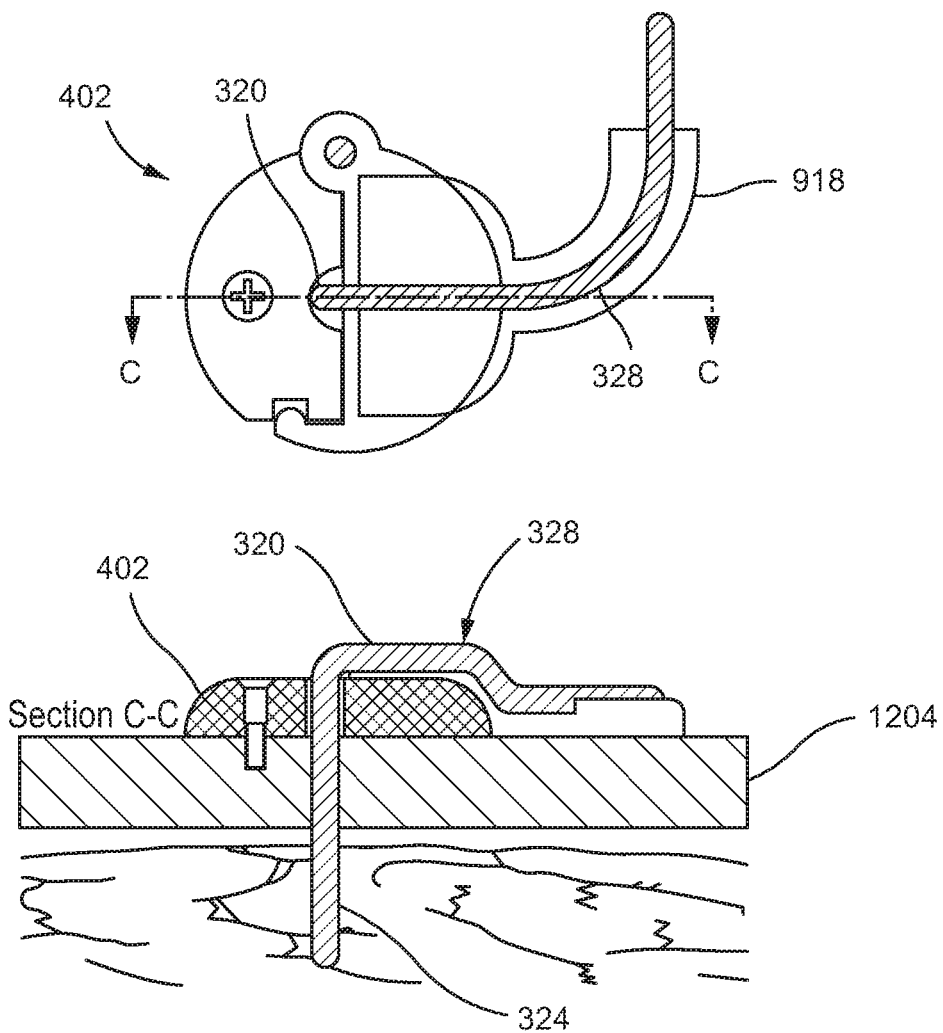

Next, after the distal end 324 of the depth lead 320 is placed at the target site, the lead fixation accessory 402 is placed in a closed position, as shown in FIGS. 12C and 12D, to secure the lead in place. If the configuration of the lead fixation accessory 402 has additional apertures 902, such as shown in FIG. 9C, one or more bones screws may be used to further secure the accessory to the skull. If a stylet 302 is used to place the lead 320 and is still installed within the lead, the stylet is then removed. (FIG. 11 at block 1108 and FIG. 12C). Next, the proximal portion 328 of the lead is positioned. For example, if the configuration of the lead fixation accessory 402 includes a channel 912 (as shown in FIG. 9D) or a strain relief 918 with a channel 920 (as shown in FIG. 9E), the proximal portion 328 of the lead 320 may be placed in the channel. (FIG. 11 at block 1110 and FIG. 12D).

The various aspects of this disclosure are provided to enable one of ordinary skill in the art to practice the present invention. Various modifications to exemplary embodiments presented throughout this disclosure will be readily apparent to those skilled in the art. Thus, the claims are not intended to be limited to the various aspects of this disclosure, but are to be accorded the full scope consistent with the language of the claims. All structural and functional equivalents to the various components of the exemplary embodiments described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed under the provisions of 35 U.S.C. § 112, sixth paragraph, unless the element is expressly recited using the phrase "means for" or, in the case of a method claim, the element is recited using the phrase "step for."

What is claimed is:

1. A lead stabilization tool for holding a lead in place near a hole in a skull, while the lead is positioned in a cannula passing through the hole, the cannula having a slotted wall having a width, the lead stabilization tool comprising:
    a housing having a proximal end, a nose at a distal end, and a lumen extending at least partially through the housing along a longitudinal axis of the housing, the lumen defining an opening through the nose of the housing;
    an extension member at least partially located in the housing and configured for displacement along the longitudinal axis;
    a grip structure configured to fit through the slotted wall of the cannula; and
    an operating mechanism coupled to the housing and at least one of the extension member and the grip structure, and configured to transition the lead stabilization tool between: 1) an extended state during which the grip structure is located distal the nose and can be positioned through the slotted wall and manipulated to at least partially encircle the lead, and 2) an at least partially retracted state during which the grip structure is located relative to the nose so as to apply a force to the lead to thereby hold the lead in place,
    wherein the extension member comprises a distal region, the grip structure is associated with the distal region, the grip structure comprises a hook formed at the distal end of the extension member, the lead has a cylindrical lead body having a radius of curvature, and the hook has a radius of curvature generally corresponding to the radius of curvature of the cylindrical lead body.

2. The lead stabilization tool of claim 1, wherein the nose at the distal end of the housing is configured to fit through the slotted wall of the cannula.

3. A lead stabilization tool for holding a lead in place near a hole in a skull, while the lead is positioned in a cannula passing through the hole, the cannula having a slotted wall having a width, the lead stabilization tool comprising:
- a housing having a proximal end, a nose at a distal end, and a lumen extending at least partially through the housing along a longitudinal axis of the housing, the lumen defining an opening through the nose of the housing;
- an extension member at least partially located in the housing and configured for displacement along the longitudinal axis;
- a grip structure configured to fit through the slotted wall of the cannula; and
- an operating mechanism coupled to the housing and at least one of the extension member and the grip structure, and configured to transition the lead stabilization tool between: 1) an extended state during which the grip structure is located distal the nose and can be positioned through the slotted wall and manipulated to at least partially encircle the lead, and 2) an at least partially retracted state during which the grip structure is located relative to the nose so as to apply a force to the lead to thereby hold the lead in place,
- wherein the extension member comprises a distal region, the grip structure is associated with the distal region, and the grip structure comprises a pincher at the distal end of the extension member, comprising at least two arms coupled together at respective first ends and spaced apart at respective second ends by a distance less than the width of the slotted wall.

4. A lead stabilization tool for holding a lead in place near a hole in a skull, while the lead is positioned in a cannula passing through the hole, the cannula having a slotted wall having a width, the lead stabilization tool comprising:
- a housing having a proximal end, a nose at a distal end, and a lumen extending at least partially through the housing along a longitudinal axis of the housing, the lumen defining an opening through the nose of the housing;
- an extension member at least partially located in the housing and configured for displacement along the longitudinal axis;
- a grip structure configured to fit through the slotted wall of the cannula; and
- an operating mechanism coupled to the housing and at least one of the extension member and the grip structure, and configured to transition the lead stabilization tool between: 1) an extended state during which the grip structure is located distal the nose and can be positioned through the slotted wall and manipulated to at least partially encircle the lead, and 2) an at least partially retracted state during which the grip structure is located relative to the nose so as to apply a force to the lead to thereby hold the lead in place,
- wherein the extension member comprises a distal region, the grip structure is associated with the distal region, and the grip structure comprises a distal region of the extension member configured to transition from a substantially linear shape to a curved shape through an application of force by a core wire extending from the operating mechanism to an end of the distal region of the extension member.

5. A lead stabilization tool for holding a lead in place near a hole in a skull, while the lead is positioned in a cannula passing through the hole, the cannula having a slotted wall having a width, the lead stabilization tool comprising:
- a housing having a proximal end, a nose at a distal end, and a lumen extending at least partially through the housing along a longitudinal axis of the housing, the lumen defining an opening through the nose of the housing;
- an extension member at least partially located in the housing and configured for displacement along the longitudinal axis;
- a grip structure configured to fit through the slotted wall of the cannula; and
- an operating mechanism coupled to the housing and at least one of the extension member and the grip structure, and configured to transition the lead stabilization tool between: 1) an extended state during which the grip structure is located distal the nose and can be positioned through the slotted wall and manipulated to at least partially encircle the lead, and 2) an at least partially retracted state during which the grip structure is located relative to the nose so as to apply a force to the lead to thereby hold the lead in place,
- wherein the operating mechanism comprises:
  - a push button configured for slideable engagement with a base of the extension member, and
  - a biasing mechanism coupled to the push button and the extension member, the biasing mechanism configured to, in an absence of an application of a force greater than a biasing force of the biasing mechanism, maintain the lead stabilization tool in the at least partially retracted, and
- wherein the push button is configured to receive a force and, upon receiving a force greater than the biasing force of the biasing mechanism, to transition the lead stabilization tool to the extended state.

6. The lead stabilization tool of claim 5, wherein the biasing mechanism comprises:
- a first biasing member associated with the push button; and
- a second biasing member associated with the extension member.

7. The lead stabilization tool of claim 6, wherein the second biasing member is axially aligned with the longitudinal axis of the housing, and the first biasing member is axially aligned with an axis generally perpendicular to the longitudinal axis.

8. A lead stabilization tool for holding a lead in place near a hole in a skull, while the lead is positioned in a cannula passing through the hole, the cannula having a slotted wall having a width, the lead stabilization tool comprising:
- a housing having a proximal end, a nose at a distal end, and a lumen extending at least partially through the housing along a longitudinal axis of the housing, the lumen defining an opening through the nose of the housing;
- an extension member at least partially located in the housing and configured for displacement along the longitudinal axis;
- a grip structure configured to fit through the slotted wall of the cannula; and
- an operating mechanism coupled to the housing and at least one of the extension member and the grip structure, and configured to transition the lead stabilization tool between: 1) an extended state during which the grip structure is located distal the nose and can be positioned through the slotted wall and manipulated to at least partially encircle the lead, and 2) an at least partially retracted state during which the grip structure is located relative to the nose so as to apply a force to the lead to thereby hold the lead in place, wherein the operating mechanism comprises:
a thumb wheel configured for rotational engagement with a base of the extension member,
a threaded portion of the thumb wheel; and
a threaded portion of the base of the extension member engaged with the threaded portion of the thumb wheel,
wherein the thumb wheel is configured to receive a rotational force in a first direction which transfers to the base of the extension member and causes the lead stabilization tool to transition to the extended state, and to receive a rotational force in a second direction which transfers to the base of the extension member and causes the lead stabilization tool to transition to the at least partially retracted state.

9. A lead stabilization tool for holding a lead in place near a hole in a skull, while the lead is positioned in a cannula passing through the hole, the cannula having a slotted wall having a width, the lead stabilization tool comprising:
a housing having a proximal end, a nose at a distal end, and a lumen extending at least partially through the housing along a longitudinal axis of the housing, the lumen defining an opening through the nose of the housing;
an extension member at least partially located in the housing and configured for displacement along the longitudinal axis;
a grip structure configured to fit through the slotted wall of the cannula; and
an operating mechanism coupled to the housing and at least one of the extension member and the grip structure, and configured to transition the lead stabilization tool between: 1) an extended state during which the grip structure is located distal the nose and can be positioned through the slotted wall and manipulated to at least partially encircle the lead, and 2) an at least partially retracted state during which the grip structure is located relative to the nose so as to apply a force to the lead to thereby hold the lead in place,
wherein the operating mechanism comprises a slide button fixedly coupled to a base of the extension member, and
wherein the slide button is configured to receive a force in a first direction along the longitudinal axis which transfers to the base of the extension member and causes the lead stabilization tool to transition to the extended state, and to receive a force in a second direction along the longitudinal axis which transfers to the base of the extension member and causes the lead stabilization tool to transition to the at least partially retracted state.

10. A lead stabilization tool for holding a lead in place near a hole in a skull, while the lead is positioned in a cannula passing through the hole, the cannula having a slotted wall having a width, the lead stabilization tool comprising:
a housing having a proximal end, a nose at a distal end, and a lumen extending at least partially through the housing along a longitudinal axis of the housing, the lumen defining an opening through the nose of the housing;
an extension member at least partially located in the housing and configured for displacement along the longitudinal axis;
a grip structure configured to fit through the slotted wall of the cannula; and
an operating mechanism coupled to the housing and at least one of the extension member and the grip structure, and configured to transition the lead stabilization tool between: 1) an extended state during which the grip structure is located distal the nose and can be positioned through the slotted wall and manipulated to at least partially encircle the lead, and 2) an at least partially retracted state during which the grip structure is located relative to the nose so as to apply a force to the lead to thereby hold the lead in place,
wherein:
the grip structure comprises a slotted tube extending from the nose and a pair of pinchers at or near a distal end of the slotted tube, and
the extension member comprises a mandrel configured to slide back and forth within the slotted tube to thereby decrease and increase a separation distance between the pair of pinchers.

* * * * *